(12) United States Patent
Soliman et al.

(10) Patent No.: US 9,289,507 B2
(45) Date of Patent: *Mar. 22, 2016

(54) CARRIERS FOR IMPROVED DRUG DELIVERY

(71) Applicant: Extend Biosciences, Inc., Cambridge, MA (US)

(72) Inventors: Tarik Soliman, Cambridge, MA (US); Laura M. Hales, Cambridge, MA (US); Howard P. Sard, Arlington, MA (US); Mukkanti Amere, Woburn, MA (US)

(73) Assignee: Extend Biosciences, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/401,519

(22) PCT Filed: Mar. 14, 2013

(86) PCT No.: PCT/US2013/031788
§ 371 (c)(1),
(2) Date: Nov. 15, 2014

(87) PCT Pub. No.: WO2013/172967
PCT Pub. Date: Nov. 21, 2013

(65) Prior Publication Data
US 2015/0104469 A1    Apr. 16, 2015

Related U.S. Application Data

(60) Provisional application No. 61/648,516, filed on May 17, 2012, provisional application No. 61/673,874, filed on Jul. 20, 2012, provisional application No. 61/780,346, filed on Mar. 13, 2013.

(51) Int. Cl.
*A61K 47/48* (2006.01)
*A61K 38/22* (2006.01)

(52) U.S. Cl.
CPC ......... *A61K 47/48215* (2013.01); *A61K 38/22* (2013.01); *A61K 47/4813* (2013.01); *A61K 47/48107* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,292,250 A | 9/1981 | DeLuca et al. |
| 4,410,515 A | 10/1983 | Holick et al. |
| 4,456,553 A | 6/1984 | Oshida et al. |
| 4,675,189 A | 6/1987 | Kent et al. |
| 4,816,567 A | 3/1989 | Cabilly et al. |
| 5,108,921 A | 4/1992 | Low et al. |
| 5,116,964 A | 5/1992 | Capon et al. |
| 5,122,614 A | 6/1992 | Zalipsky |
| 5,214,170 A | 5/1993 | Tanabe et al. |
| 5,232,836 A | 8/1993 | Bouillon et al. |
| 5,416,016 A | 5/1995 | Low et al. |
| 5,428,023 A | 6/1995 | Russell-Jones et al. |
| 5,447,851 A | 9/1995 | Beutler et al. |
| 5,545,806 A | 8/1996 | Lonberg et al. |
| 5,545,807 A | 8/1996 | Surani et al. |
| 5,550,111 A | 8/1996 | Suhadolnik et al. |
| 5,569,825 A | 10/1996 | Lonberg et al. |
| 5,574,018 A | 11/1996 | Habberfield et al. |
| 5,605,690 A | 2/1997 | Jacobs et al. |
| 5,625,126 A | 4/1997 | Lonberg et al. |
| 5,629,384 A | 5/1997 | Veronese et al. |
| 5,633,425 A | 5/1997 | Lonberg et al. |
| 5,661,016 A | 8/1997 | Lonberg et al. |
| 5,688,488 A | 11/1997 | Low et al. |
| 5,691,328 A | 11/1997 | Peterson et al. |
| 5,714,142 A | 2/1998 | Blaney et al. |
| 5,739,277 A | 4/1998 | Presta et al. |
| 5,767,254 A | 6/1998 | Polt |
| 5,869,466 A | 2/1999 | Russell-Jones et al. |
| 5,876,969 A | 3/1999 | Fleer et al. |
| 5,919,452 A | 7/1999 | Le et al. |
| 5,932,462 A | 8/1999 | Harris et al. |
| 6,093,701 A | 7/2000 | Wolff et al. |
| 6,342,225 B1 | 1/2002 | Jones et al. |
| 6,395,492 B1 | 5/2002 | Manoharan et al. |
| 6,455,714 B1 | 9/2002 | Holick et al. |
| 6,660,843 B1 | 12/2003 | Feige et al. |
| 6,713,280 B1 | 3/2004 | Huang et al. |
| 6,787,660 B1 | 9/2004 | Armbruster et al. |
| 6,858,227 B1 | 2/2005 | Lal et al. |

(Continued)

FOREIGN PATENT DOCUMENTS

| | | |
|---|---|---|
| EP | 0312360 B1 | 6/1992 |
| EP | 0486525 B1 | 6/1994 |

(Continued)

OTHER PUBLICATIONS

American Peptide Company, "The case for PEG conjugation", 2008.
Drug Lib.com, "Vitamin D2", copyright, 2006-2015.
Kojima et al. "Ghrelin: From Gene to Physiological Function", 2010, p. 185-205.
Kozbor, "A Human Hybrid Myeloma for Production of Human Monoclonal Antibodies," J. Immunol, 133: 3001 (1984).

(Continued)

*Primary Examiner* — James H Alstrum Acevedo
*Assistant Examiner* — Tara Martinez
(74) *Attorney, Agent, or Firm* — Kaplan IP Law, P.C.; Jonathan M. Kaplan

(57) ABSTRACT

The invention provides carriers that enhance the absorption, half-life or bioavailability of therapeutic compounds. The carriers comprise targeting groups that bind the Vitamin D Binding protein (DBP), conjugation groups for coupling the targeting groups to the therapeutic compounds, and optionally scaffolding moieties.

25 Claims, 6 Drawing Sheets

(56) References Cited

U.S. PATENT DOCUMENTS

| | | |
|---|---|---|
| 6,887,470 B1 | 5/2005 | Bridon et al. |
| 6,929,797 B2 | 8/2005 | Mazess et al. |
| 7,045,318 B2 | 5/2006 | Ballance |
| 7,141,547 B2 | 11/2006 | Rosen et al. |
| 7,176,278 B2 | 2/2007 | Prior |
| 7,186,797 B2 | 3/2007 | West et al. |
| 7,217,689 B1 | 5/2007 | Elliott et al. |
| 7,256,253 B2 | 8/2007 | Bridon et al. |
| 7,579,324 B2 | 8/2009 | Burnet et al. |
| 7,601,332 B2 | 10/2009 | Vlahov et al. |
| 7,608,681 B2 | 10/2009 | Dennis et al. |
| 7,741,286 B2 | 6/2010 | Bridon et al. |
| 7,741,453 B2 | 6/2010 | Erickson et al. |
| 7,803,777 B2 | 9/2010 | DeFrees |
| 7,982,018 B2 | 7/2011 | Ulich et al. |
| 8,076,476 B2 | 12/2011 | Reeves et al. |
| 8,129,348 B2 | 3/2012 | Besman et al. |
| 8,178,495 B2 | 5/2012 | Chilkoti |
| 8,188,223 B2 | 5/2012 | Beirnaert et al. |
| 8,252,755 B2 | 8/2012 | Yamada et al. |
| 8,551,937 B2 | 10/2013 | Wakabayashi et al. |
| 8,779,109 B2 | 7/2014 | Behrens et al. |
| 8,785,603 B2 | 7/2014 | Sahakian et al. |
| 2002/0136731 A1 | 9/2002 | Mazess et al. |
| 2002/0141996 A1 | 10/2002 | Le et al. |
| 2003/0129194 A1 | 7/2003 | Mazess et al. |
| 2003/0203359 A1 | 10/2003 | Uhlmann et al. |
| 2004/0132104 A1 | 7/2004 | Sackrison et al. |
| 2004/0186063 A1 | 9/2004 | Gutke et al. |
| 2005/0260237 A1 | 11/2005 | Byun et al. |
| 2006/0153839 A1 | 7/2006 | Mohamed et al. |
| 2007/0249571 A1 | 10/2007 | Tamarkin |
| 2008/0199960 A1 | 8/2008 | Juliano et al. |
| 2008/0242595 A1 | 10/2008 | Doyle |
| 2009/0131360 A1 | 5/2009 | Woolf et al. |
| 2009/0176253 A1 | 7/2009 | Bieniarz et al. |
| 2009/0305986 A1 | 12/2009 | Belouski et al. |
| 2010/0015046 A1 | 1/2010 | Govindan et al. |
| 2010/0074885 A1 | 3/2010 | Schiff et al. |
| 2010/0104626 A1 | 4/2010 | Leamon et al. |
| 2010/0168033 A1 | 7/2010 | Ghigo et al. |
| 2010/0234303 A1 | 9/2010 | Millar et al. |
| 2010/0323973 A1 | 12/2010 | Leamon et al. |
| 2011/0166063 A1 | 7/2011 | Bossard et al. |
| 2011/0293579 A1 | 12/2011 | Nielsen et al. |
| 2011/0312027 A1 | 12/2011 | Young et al. |
| 2012/0028887 A1 | 2/2012 | Shai et al. |
| 2012/0129766 A1 | 5/2012 | Boettcher et al. |
| 2012/0129767 A1 | 5/2012 | Tulipano et al. |
| 2012/0165377 A1 | 6/2012 | Takizawa et al. |
| 2012/0177646 A1 | 7/2012 | Belouski et al. |
| 2013/0129724 A1 | 5/2013 | Boettcher et al. |
| 2013/0164310 A1 | 6/2013 | Annathur et al. |
| 2013/0172251 A1 | 7/2013 | Kangawa et al. |
| 2013/0231277 A1 | 9/2013 | Mohammadi et al. |
| 2013/0261013 A1 | 10/2013 | Baltzer et al. |
| 2013/0331316 A1 | 12/2013 | Mohammadi et al. |
| 2014/0058063 A1 | 2/2014 | Vlahov et al. |
| 2014/0135260 A1 | 5/2014 | Dong et al. |
| 2014/0179560 A1 | 6/2014 | Olson et al. |
| 2014/0194352 A1 | 7/2014 | Ling et al. |
| 2014/0200261 A1 | 7/2014 | Hoge et al. |
| 2014/0213512 A1 | 7/2014 | Ellison et al. |
| 2014/0323396 A1 | 10/2014 | Belouski et al. |

FOREIGN PATENT DOCUMENTS

| | | |
|---|---|---|
| EP | 0804456 B1 | 8/2002 |
| EP | 1151102 B1 | 4/2006 |
| EP | 1931711 B1 | 4/2009 |
| EP | 2085406 A1 | 8/2009 |
| EP | 2423233 A2 | 2/2012 |
| EP | 2481427 A1 | 8/2012 |
| EP | 2316854 B1 | 12/2013 |
| EP | 2695617 A2 | 2/2014 |
| WO | 9110741 A1 | 7/1991 |
| WO | 9214493 A1 | 9/1992 |
| WO | 9216221 A1 | 10/1992 |
| WO | 9307883 A1 | 4/1993 |
| WO | 9312145 A1 | 6/1993 |
| WO | 9510302 A1 | 4/1995 |
| WO | 9633735 A1 | 10/1996 |
| WO | 9634096 A1 | 10/1996 |
| WO | 9734637 A2 | 9/1997 |
| WO | 9824893 A2 | 6/1998 |
| WO | 9961055 A1 | 12/1999 |
| WO | 0066090 A1 | 11/2000 |
| WO | 0074721 A1 | 12/2000 |
| WO | 0069900 A3 | 2/2001 |
| WO | 0145746 A3 | 10/2001 |
| WO | 02062844 A2 | 8/2002 |
| WO | 02066511 A2 | 8/2002 |
| WO | 02076489 A1 | 10/2002 |
| WO | 03011213 A2 | 2/2003 |
| WO | 02046227 A3 | 4/2003 |
| WO | 03025139 A3 | 8/2003 |
| WO | 2004009124 A2 | 1/2004 |
| WO | 2004011498 A3 | 6/2004 |
| WO | 2004041865 A3 | 7/2004 |
| WO | 2005097158 A1 | 10/2005 |
| WO | 2005105071 A1 | 11/2005 |
| WO | 2007012188 A1 | 2/2007 |
| WO | 2007035922 A2 | 3/2007 |
| WO | 2007049941 A1 | 5/2007 |
| WO | 2006116156 A3 | 10/2007 |
| WO | 2007097934 A3 | 11/2007 |
| WO | 2007103455 A3 | 11/2007 |
| WO | 2008036841 A3 | 10/2008 |
| WO | 2008118013 A2 | 10/2008 |
| WO | 2009121884 A1 | 10/2009 |
| WO | 2011146902 A1 | 11/2011 |
| WO | 2011123813 A3 | 12/2011 |
| WO | 2012041451 A1 | 4/2012 |
| WO | 2012158962 A2 | 11/2012 |
| WO | 2013033230 A1 | 3/2013 |
| WO | 2013163162 A1 | 10/2013 |
| WO | 2014041024 A1 | 3/2014 |
| WO | 2013040093 A3 | 5/2014 |
| WO | 2014081864 A1 | 5/2014 |
| WO | 2014083427 A2 | 6/2014 |

OTHER PUBLICATIONS

Kutner A, et al., 1986, "Photoactivable Analogues for Labeling 25-Hydroxyvitamin D3 Serum Binding Protein and for 1,25-Dihydroxyvitamin D3 Intenstinal Receptor Protein," Bioorganic Chemistry 14: 134-147.

Langenheim JF and Chen WY, 2009, "Improving the Pharmacokinetics/Pharmacodynamics of Prolactin, GH, and Their Antagonists by Fusion to a Synthetic Albumin-Binding Peptide," Journal of Endocrinology 203:375-387.

Leamon CP and Low PS, 2001, "Folate-Mediated Targeting: From Diagnostics to Drug and Gene Delivery," Drug Discovery Today 6(1): 44-51.

Leamon CP and Reddy JA, 2004, "Folate-Targeted Chemotherapy," Advanced Drug Delivery Reviews 56: 1127-1141.

Lee et al., "Bivalent antibody phage display mimics natural immunoglobulin," J. Immunol. Methods 284(1-2): 119-132(2004).

Lee et al., "High-affinity Human Antibodies from Phage-displayed Synthetic Fab Libraries with a Single," J. Mol. Biol. 340(5): 1073-1093 (2004).

Leyssens C, et al., 2014, "The Future of Vitamin D Analogues," Frontiers in Physiology 5: Article 122.

Liang S, et al., 2013, "Structural Basis for Treating Tumor Necrosis Factor alpha (TNFalpha)-associated Diseases with the Therapeutic Antibody Infliximab," Journal of Biological Chemistry 288: 13799-13807.

Liebner R, et al., 2014, "Protein HESylation for Half-Life Extension: Synthesis, Characterization and Pharmacokinetics of HESylated Anakinra," European Journal of Pharmaceutics and Biopharmaceutics 87: 378-385.

(56) References Cited

OTHER PUBLICATIONS

Link RP, et al., 1987, "Photoaffinity Labeling of Serum Vitamin D Binding Protein by 3-Deoxy-3-azido-25-hydroxyvitamin D3," Biochemistry 26: 3957-3964.
Lips P, 2006, "Vitamin D Physiology," Progress in Biophysics and Molecular Biology 92: 4-8.
Lonberg 2008, "Fully human antibodies from transgenic mouse and phage display platforms" Curr Opin Immunol. Aug. 2008;20(4):450-9.
Lonberg and Huszar, Intern. Rev. Immunol. 13: 65-93 (1995).
Lonberg et al.,"Antigen-specific human antibodies from mice comprising four distinct genetic modifications," Nature 368: 856-859 (1994).
Lu Y, et al., 2004, "Folate Receptor-Targeted Immunotherapy of Cancer: Mechanism and Therapeutic Potential," Advanced Drug Delivery Reviews 56: 1161-1176.
Makrides SC, et al., 1996, "Extended in Vivo Half-Life of Human Soluble Complement Receptor Type 1 Fused to a Serum Albumin-Binding Receptor," Journal of Pharmacology and Experimental Therapeutics 277(1): 534-542.
Marks et al., "By-passing Immunization Human Antibodies from V-gene Libraries Displayed on Phage," J. Mol. Biol, 222: 581-597 (1991).
Marks et al., "By-Passing Immunization: Building High Affinity Human Antibodies by Chain Shuffling," Bio. Technology 10: 779-783 (1992).
McIntyre et al., "Effects of new analogues of vitamin D on bone cells: Implications for treatment of uremic bone disease," Kidney Int. 55: 500 (1999).
McLeod et al, "The Vitamin D-binding Protein, &-Fetoprotein, Albumin Multigene Family: Detection of Transcripts in Multiple Tissues," J Biol Chem. 264(2):1260-7 (1989).
Mero A, et al., 2013, "Conjugation of Hyaluronan to Proteins," Carbohydrate Polymers 92: 2163-2170.
Misbah S, et al., 2009, "Subcutaneous immunoglobulin: opportunities and outlook," Clinical and Experimental Immunology 158(Suppl 1): 51-59.
Morrison, "Success in Specification," Nature 368: 812-813 (1994).
Mu J, et al, 2012, "FGF21 Analogs of Sustained Action Enabled by Orthogonal Biosynthesis Demonstrate Enhanced Antidiabetic Pharmacology in Rodents," Diabetes 61:505-512.
Mëller DN, et al., 2011, "Vitamin D Review," Journal of the Renin-Angiotensin-Aldosterone System 12: 125-8.
Nanocs PEG Products located at: http://www.nanocs.com/PEG/VTPEG.htm.
Neary NM, et al., 2004, "Ghrelin Increases Energy Intake in Cancer Patients with Impaired Appetite: Acute, Randomized, Placebo-Controlled Trial," The Journal of Clinical Endocrinology & Metabolism 89(6): 2832-2836.
Nestor, J.J., Jr. (2007) Comprehensive Medicinal Chemistry II 2: 573-601.
Neuberger, "Generating high-avidity human Mabs in mice," Nature Biotechnol. 14: 826 (1996).
Norman AW, et al., 2001, "Ligands for the Vitamin D Endocrine System: Different Shapes Function as Agonists and Antagonists for Genomic and Rapid Response Receptors or as a Ligand for the Plasma Vitamin D Binding Protein," Journal of Steroid Biochemistry and Molecular Biology 76: 49-59.
Notice of Allowance dated Jun. 23, 2009, for U.S. Appl. No. 10/765,336.
Ono Y, 2014, "Multifunctional and Potent Roles of the 3-Hydroxypropoxy Group Provide Eldecalcitol's Benefit in Osteoporosis Treatment," Journal of Steroid Biochemistry & Molecular Biology 139: 88-97.
Park S, et al., 2014, "A Novel Delivery Platform for Therapeutic Peptides," Biochemical and Biophysical Research Communications 450(1): 13-18.
Payne RJ, et al., 2004, "Synthesis and Protein Conjugation Studies of Vitamin K Analogues," Bioorganic & Medicinal Chemistry 12: 5785-5791.
Peleg S and Posner GH, 2003, "Vitamin D Analogs as Modulators of Vitamin D Receptor Action," Current Topics in Medicinal Chemistry 3(14): 1555-72.
Petrus AK, et al., 2009, "Exploring the Implications of Vitamin B12 Conjugation to Insulin on Insulin Receptor Binding," ChemMedChem 4: 421-426.
Pfutzner, A and Forst, T, 2005, "Pulmonary insulin delivery by means of the Technosphere™ drug carrier mechanism," Expert Opin Drug Deliv 2:1097-1106.
Presta, "Antibody Engineering," Current Opinion in Biotechnology, 3:394-398 (1992).
Punj V, et al., 2004, "Effect of Vitamin D Analogue (1alpha Hydroxy D5) Immunoconjugated to Her-2 Antibody on Breast Cancer," International Journal of Cancer 108: 922-929.
Rattan, S.I., et al. (1992), "Protein Synthesis, Post translational Modifications, and Aging," Ann N Y Acad Sci 663:48-62.
Ray R, et al., 1986, "Photoaffinity Labeling of the Rat Plasma Vitamin D Binding Protein with [26,27-3H]-25- Hydroxyvitamin D3 3beta-[N-(4-azido-2-nitrophenyl)glycinate]," Biochemistry 25(17): 4729-4733.
Reddy JA, et al., 2007, "Folate Receptor-Specific Antitumor Activity of EC131, a Folate-Maytansinoid Conjugate," Cancer Research 67: 6376-6382.
Revelle et al., "Synthesis and Biological Activity of 3beta-Fluorovitamin D3,: Comparison of the Biological Activity of 3beta-Fluorovitamin D3, and 3-Deoxyvitamin D3," J. Steroid Biochem. 22:469-474 (1985).
Riechmann et al., "Reshaping human antibodies for therapy," Nature 332:323-329 (1988).
Rosenstock J, et al., 2009, "Potential of Albiglutide, a Long-Acting GLP-1 Receptor Agonist, in Type 2 Diabetes," Diabetes Care 32(10): 1880-1886.
Salmaso S, et al., 2009, "Targeting Glioma Cells in Vitro with Ascorbate-Conjugated Pharmaceutical Nanocarriers," Bioconjugate Chemistry 20: 2348-2355.
Sasson K, et al., 2010, "Engineering Prolonged Acting Prodrugs Employing an Albumin-Binding Probe that Undergoes Slow Hydrolysis at Physiological Conditions," Journal of Controlled Release 142: 214-220.
Schlapschy M, et al., 2013,"PASylation: A Biological Alternative to PEGylation for Extending the Plasma Half-Life of Pharmaceutically Active Proteins," Protein Engineering, Design & Selection 26: 489-501.
SciFinder, Maleimide Side, Nov. 6, 2012.
SciFinder, Minimal Vitamin D side, Nov. 6, 2012.
SciFinder, Vitamin D side, Nov. 6, 2012.
Seifter, S. and Englard, S. (1990), "Analysis for Protein Modifications and Nonprotein Cofactors," Methods Enzymol 182: 626-646.
Sidhu et al., "Phage-displayed Antibody Libraries of Synthetic Heavy Chain Complementarity Determining Regions," J. Mol. Biol. 338(2): 299-310 (2004).
Slatopolsky et al., "A New Analog of Calcitriol, 19-Nor-1,25-(OH),D, , Suppresses Parathyroid Hormone Secretion in Uremic Rats in the Absence of Hypercalcemia," Am J. Kidney Dis. 26: 852 (1995).
So et al., "A Novel Gemini Vitamin D Analog Represses the Expression of a Stem Cell Marker CD44 in Breast Cancer," Mol Pharmacol. 79(3):360-7 (2011).
Stamatov SD and Gronowitz S, 1990, "Glyceroamidothiophosphates of Cholecalciferol (Vitamin D3)," Lipids 25: 149-151.
Steddon et al. "Vitamin D analogues: how do they differ and what is their clinical role," Nephrol. Dial. Transplant. 16(10): 1965-1967 (2001).
Sun C, et al., 2013, "Bifunctional PEGylated Exenatide-Amylinomimetic Hybrids to Treat Metabolic Disorders: An Example of Long-Acting Dual Hormonal Therapeutics," Journal of Medicinal Chemistry 56: 9328-9341.
Swamy N, et al., 1995, "Affinity Purification of Human Plasma Vitamin D-Binding Protein," Protein Expression and Purification 6: 185-188.
Swamy N, et al., 1997, "Roles of Structure and Orientation of Ligands and Ligand Mimics inside the Ligand-Binding Pocket of the Vitamin D-Binding Protein," Biochemistry 36: 7432-7436.

(56) References Cited

OTHER PUBLICATIONS

Swamy N, et al., 2000, "Probing the Vitamin D Sterol Binding Pocket of Human Vitamin D Binding Protein with Bromoacetate Affinity Labeling Reagents Containing the Affinity Probe at C-3, C-6, C-11, and C-19 Positions of Parent Vitamin D Sterols," Archives of Biochemistry and Biophysics 373(2): 471-478.
Teegarden et. al.,"Determination of the Affinity of Vitamin D Metabolites to Serum Vitamin D Binding Protein Using AssayEmploying Lipid-Coated Polystyrene Beads," Anal. Biochemistry 199(2):293-299 (1991).
Touraine P, et al., 2009, "Lipoatrophy in GH Deficient Patients Treated with a Long-Acting PEGylated GH," European Journal of Endocrinology 161(4): 533-40.
Trussel S, et al., 2009, "New Strategy for the Extension of the Serum Half-Life of Antibody Fragments," Bioconjugate Chemistry 20: 2286-2292.
Vaswani and Hamilton, Ann. Allergy, Asthma & Immunol. 1:105-115 (1998).
Verboven C, et al., 2002, "A Structural Basis for the Unique Binding Features of the Human Vitamin D-Binding Protein," Nature Structural Biology 9: 131-6.
Vestergaard ET, et al., "Constant intravenous infusion in healthy men: clinical pharmacokinetics and metabolic effects," Am J Physiol Endocrinol Metab 292:E1829-E1836.
Vlahov IR, et al., 2006, "Design and Regioselective Synthesis of a New Generation of Targeted Chemotherapeutics. Part 1: EC145, a Folic Acid Conjugate of Desacetylvinblastine Monohydrazide," Bioorganic & Medicinal Chemistry Letters 16: 5093-5096.
Wang X-F, et al., 2007, "A Peptide Conjugate of Vitamin E Succinate Targets Breast Cancer Cells with High ErbB2 Expression," Cancer Research 67: 3337-3344.
Wootton AM, 2005, "Improving the Measurement of 25-Hydroxyvitamin D," Clinical Biochemist Reviews 26: 33-6.
Wu B and Sun Y-N, 2014, "Pharmacokinetics of Peptide-Fc Fusion Proteins," Journal of Pharmaceutical Sciences 103:53-64.
Xu J et al., 2009. "Acute glucose-lowering and insulin-sensitizing action of FGF21 in insulin-resistant mouse models—association with liver and adipose tissue effects," Am J Physiol Endocrinol Metab 297: E1105-E1114.
Xu P., et al., 2014, Long-acting hypoglycemic effects of PEGylated FGF21 and insulin glargine in mice with type 1 diabetes, Journal of Diabetes and Its Complications, in press, http://dx.doi.org/10.1016/j.jdiacomp.2014.10.001.
Zeidler J, et al., 2012, "Biologic TNF inhibiting agents for treatment of inflammatory rheumatic diseases: dosing patterns and related costs in Switzerland from a payers perspective" Health Economics Review 2:20.
Zhang J, et al., 2010 "Identification of Two Distinct Cell Binding Sequences in the Vitamin D Binding Protein," Biochimica et Biophysica Acta 1803: 623-629.
Zhang Q, et al., 2010, "Synthesis of C-11 Linked Active Ester Derivatives of Vitamin D3 and Their Conjugations to 42-Residue Helix-Loop-Helix Peptides," Tetrahedron 66: 4577-4586.
Zhang, L. and Bulaj, G. (2012). "Converting Peptides into Drug Leads by Lipidation," Curr Med Chem 19: 1602-1618.
Zhao J, et al., 2013, "Targeted Co-delivery of Docetaxel and siPlk1 by Herceptin-conjugated Vitamin E TPGS Based Immunomicelles," Biomaterials 34: 3411-3421.
Zhou K, et al., 2009, "Studies of Poly(ethylene glycol) Modification of HM-3 Polypeptides," Bioconjugate Chemistry 20: 932-936.
Gozes, "Potential clinical applications of vasoactive intestinal peptide: a selected update," Best Practice & Research Clinical Endocrinology & Metabolism vol. 18, No. 4, pp. 623-640, 2004.
Abe et.al., Synthetic analogues of vitamin D3 with an oxygen atom in the side chain skeleton, FEBS Lett. 226:58-62 (1987).
Addo JK, et al., 2002, "The C19 Position of 25-Hydroxyvitamin D3 Faces Outward in the Vitamin D Sterol-Binding Pocket of Vitamin D-Binding Protein," Bioorganic & Medicinal Chemistry Letters 12: 279-281.

Ahsan, F et al., 2001, Enhanced Bioavailability of Calcitonin Formulated with Alkylglycosides following Nasal and Ocular Administration in Rats, Pharm Res 18:1742-1746.
Amiram M, et al., 2013, "A Depot-Forming Glucagon-Like Peptide-1 Fusion Protein Reduces Blood Glucose for Five Days with a Single Injection," Journal of Controlled Release 172: 144-151.
Amiram M, et al., 2013, "Injectable Protease-Operated Depots of Glucagon-Like Peptide-1 Provide Extended and Tunable Glucose Control," Proceedings of the National Academy of Sciences, USA 110(8): 2792-2797.
Arnaud J and Constans J, 1993, "Affinity Differences for Vitamin D Metabolites Associated with the Genetic Isoforms of the Human Serum Carrier Protein (DBP)," Human Genetics 92: 183-188.
Arnold, JJ et al., 2004, Correlation of Tetradecylmaltoside Induced Increases in Nasal Peptide Drug Delivery with Morphological Changes in Nasal Epithelial Cells, J Pharm Sci 93: 2205-13.
Arnusch CJ, et al., 2012, "Ultrashort Peptide Bioconjugates Are Exclusively Antifungal Agents and Synergize with Cyclodextrin and Amphotericin B," Antimicrobial Agents and Chemotherapy 56(1) 1-9.
Baggio LL, et al., 2004, "A Recombinant Human Glucagon-Like Peptide (GLP)-1-Albumin Protein (Albugon) Mimics Peptidergic Activation of GLP-1 Receptor-Dependent Pathways Coupled with Satiety, Gastrointestinal Motility, and Glucose Homeostasis," Diabetes 53: 2492-2500.
Bailon P, et al., 2001, "Rational Design of a Potent, Long-Lasting Form of Interferon: a 40 kDa Branched Polyethylene Glycol-Conjugated Interferon Alpha-2a for the Treatment of Hepatitis C," Bioconjugate Chemistry 12(2): 195-202.
Bao W, et al., 2013, "Novel Fusion of GLP-1 with a Domain Antibody to Serum Albumin Prolongs Protection against Myocardial Ischemia/Reperfusion Injury in the Rat," Cardiovascular Diabetology 12: 148.
Barrington P, et al., 2011, "A 5-Week Study of the Pharmacokinetics and Pharmacodynamics of LY2189265, a Novel, Long-Acting Glucagon-Like Peptide 1 Analogue, in Patients with Type 2 Diabetes," Diabetes, Obesity, and Metabolism 13:426-433.
Barrington P, et al., 2011, "LY2189265, a Long-Acting Glucagon-Like Peptide 1 Analogue, Showed a Dose-Dependent Effect on Insulin Secretion in Healthy Patients," Diabetes, Obesity, and Metabolism 13:434-438.
Ben-Shabat S, et al., 2005, "Vitamin D3-Based Conjugates for Topical Treatment of Psoriasis: Synthesis, Antiproliferative Activity, and Cutaneous Penetration Studies," Pharmaceutical Research 22(1): 50-57.
Bishop JE, et al., 1994, "Profile of Ligand Specificity of the Vitamin D Binding Protein for 1alpha-25-dihydroxyvitamin D3 and its Analogues," Journal of Bone and Mineral Research 9(8): 1277-1288.
Blouch K, et al., 1997, "Molecular Configuration and Glomerular Size Selectivity in Healthy and Nephrotic Humans," American Journal of Physiology 273 (Renal Physiology 42): F430-F437. (May 20, 1997).
Boerner et al., Human mAb From in Vitro-Primed Lymphocytes, J. Immunol, 147: 86-95 (1991).
Bouillon R, et al., 1980, "Comparative Study of the Affinity of the Serum Vitamin D Binding Protein," Journal of Steroid Biochemistry 13: 1029-1034.
Bouillon R, et al., 1991, "Vitamin D Analogues with Low Affinity for the Vitamin D Binding Protein: Enhanced in Vitro and Decreased in Vivo Activity," Journal of Bone and Mineral Research 6(10): 1051-1057.
Bouman-Theo E, et al., 2008, "A Phase I, Single and Fractionated, Ascending-Dose Study Evaluating the Safety, Pharmacokinetics, Pharmacodynamics, and Immunogenicity of an Erythropoietin Mimetic Antibody Fusion Protein (CNTO 528) in Healthy Male Subjects," Journal of Clinical Pharmacology 48: 1197-1207.
Cai Y, et al., 2013, "Long-Acting Preparations of Exenatide," Drug Design, Development, and Therapy 7: 963-970.
Camacho RC, et al., 2013, "PEGylated FGF21 Rapidly Normalizes Insulin-Stimulated Glucose Utilization in Diet-Induced Insulin Resistant Mice," European Journal of Pharmacology 715: 41-45.
Capon DJ, et al., 1989, "Designing CD4 Immunoadhesions for AIDS Therapy," Nature 337: 525-531.

(56) References Cited

OTHER PUBLICATIONS

Carlberg C, 2003, "Molecular Basis for the Selective Activity of Vitamin D Analogues," Journal of Cellular Biochemistry 88: 274-281.

Chae SY, et al., 2009, "Pharmacokinetic and Pharmacodynamic Evaluation ofSite-Specific PEGylated Glucagon-Like Peptide-1 Analogs asFlexible Postprandial-Glucose Controllers," Journal of Pharmaceutical Sciences 98(4): 1556-1567.

Chae SY, et al., 2010, "Biochemical, Pharmaceutical, and Therapeutic Properties of Long-Acting Lithocholic Acid Derivatized Exendin-4 Analogues," Journal of Controlled Release 142: 206-213.

Chae SY, et al., 2010, "The Fatty Acid Conjugated Exendin-4 Analogues for Type 2 Antidiabetic Therapeutics," Journal of Controlled Release 144: 10-16.

Chalasani KB, et al., 2007, "Effective Oral Delivery of Insulin in Animal Models Using Vitamin B12-coated Dextran Nanoparticles," Journal of Controlled Release 122: 141-150.

Chen et al., Selection and Analysis of an Optimized Anti-VEGF Antibody: Crystal Structure of an Affinity-matured Fab, J. Mol. Biol. 293:865-881 (1999).

Chen S, et al., 2010, "Mechanism-Based Tumor-Targeting Drug Delivery System. Validation of Efficient Vitamin Receptor-Mediated Endocytosis and Drug Release," Bioconjugate Chemistry 21: 979-987.

Choi H-I, et al., 2009, "A Novel L-Ascorbic Acid and Peptide Conjugate with Increased Stability and Collagen Biosynthesis," BMB Reports 42(11): 743-746.

Clackson et al., Making antibody fragments using phage display libraries, Nature, 352: 624-628 (1991).

Clardy-James S, et al., 2013, "Synthesis, Characterization, and Pharmacodynamics of Vitamin-B12-Conjugated Glucagon-Like Peptide-1," ChemMedChem 8: 582-586.

Clark et al. Long-acting Growth Hormones Produced by Conjugation with Polyethylene Glycol*, J. Biol. Chem. 271:21969-21977 (1996).

Cleland JL, et al., 2012, "A Novel Long-Acting Human Growth Hormone Fusion Protein (VRS-317): Enhanced in Vivo Potency and Half-Life," Journal of Pharmaceutical Sciences 101(8): 2744-2754.

Clemens TL, et al., 1983, "A Simple Method for Generation of Antibodies with Specificity for 1,25- Dihydroxyergocalciferol and 1,25-Dihydroxycholecalciferol," Steroids 42(5): 503-509.

Conforti A, et al., 1987, "PEG Superoxide Dismutase Derivatives: Anti-Inflammatory Activity in Carrageenan Pelurisy in Rats," Pharmacological Research Communications 19: 287-294.

Cooke NE and Haddad JG, 1989, "Vitamin D Binding Protein (Gc-Globulin)," Endocrinology Reviews 10: 294-307.

Datta-Mannan A, et al, 2012, "Influence of improved FcRn binding on the subcutaneous bioavailability of monoclonal antibodies in cynomolgus monkeys," MAbs. 4(2):267-73.

de Schepper J, et al., 2011, "Long-Acting PEGylated Human GH in Children with GH Deficiency: A Single-Dose, Dose-Escalation Trial Investigating Safety, Tolerability, Pharmacokinetics and Pharmacodynamics," European Journal of Endocrinology 165(3): 401-409.

de Smidt PC, et al., 1991, "Association of Antisense Oligonucleotides with Lipoproteins Prolongs the Plasma Half-Life and Modifies the Tissue Distribution," Nucleic Acids Research 19(17): 4695-4700.

DeLuca HF, 2008, "Evolution of our Understanding of Vitamin D," Nutrition Reviews 66(suppl. 2): S73-8.

Dennis MS, et al., 2002, "Albumin Binding as a General Strategy for Improving the Pharmacokinetics of Proteins," Journal of Biological Chemistry 277: 35035-35043.

Dennis MS, et al., 2007, "Imaging Tumors with an Albumin-Binding Fab, a Novel Tumor-Targeting Agent," Cancer Research 67: 254-261.

Ding S, et al., 2014, "Multivalent Antiviral XTEN-Peptide Conjugates with Long in Vivo Half-Life and Enhanced Solubility," Bioconjugate Chemistry 25(7): 1351-9.

Doores, K., et al., "Direct deprotected glycosyl-asparagine ligation" Chem. Commun., 1401-1403, 2006.

Elliott S, et al., 2003, "Enhancement of in Vivo Therapeutic Protein Activities through Glycoengineering," Nature Biotechnology 21: 414-421.

Erben and Musculoskel, "Vitamin D analogs and bone," Neuron Interact. 2(1):59-69 (2001).

Fellouse, "Synthetic antibodies from a four-amino-acid code: A dominant role for tyrosine in antigen recognition," Proc. Natl. Acad. Sci. USA 101(34): 12467-12472 (2004).

Fishburn, "The Pharmacology of PEGylation: Balancing PD with PK to Generate Novel Therapeutics," J. Pharm. Sci. 97:4167-4183 (2008).

Fisher CJ, et al., 1996, "Treatment of Septic Shock with the Tumor Necrosis Factor Receptor:Fc Fusion Protein," The New England Journal of Medicine 334: 1697-1702.

Freeman JN, et al., 2013, "Chronic central ghrelin infusion reduces blood pressure and heart rate despite increasing appetite and promoting weight gain in normotensive and hypertensive rats," Peptides 42: 35-42.

Gabizon A, et al., 2004, "Tumor Cell Targeting of Liposome-Entrapped Drugs with Phospholipid-Anchored Folic Acid PEG Conjugates," Advanced Drug Delivery Reviews 56: 1177-1192.

Gaich G, et al., 2013, "The Effects of LY2405319, an FGF21 Analog, in Obese Human Subjects with Type 2 Diabetes," Cell Metabolism 18: 333-340.

Garay RP, et al., 2012, "Antibodies against Polyethylene Glycol in Healthy Subjects and in Patients Treated with PEG-Conjugated Agents," Expert Opinion on Drug Delivery 9(11): 1319-1323.

Gong N, et al., 2011, "Site-Specific PEGylation of Exenatide Analogues Markedly Improved Their Glucoregulatory Activity," British Journal of Pharmacology 163: 399-412.

Gourlet, P., et al. (1998), "Interaction of lipophilic VIP derivatives with recombinant VIP rPACAP 1 and VIP rPACAP receptors," Eur J Pharmacol 354: 105-111.

Haddad JG, 1995, "Plasma Vitamin D-Binding Protein (Gc-Globulin): Multiple Tasks," Journal of Steroid Biochemistry and Molecular Biology 53: 579-82.

Haddad JG, et al., 1992, "Identification of the Sterol- and Actin-Binding Domains of Plasma Vitamin D Binding Protein (Gc-Globulin)," Biochemistry 31: 7174-7181.

Haddad JG, et al., 1993, "Human Plasma Transport of Vitamin D After its Endogenous Synthesis," Journal of Clinical Investigation 91: 2552-2555.

Hakimelahi GH, et al., 2001, "Design and Synthesis of a Cephalosporin-Retinoic Acid Prodrug Activated by a Monoclonal Antibody-betaLactamase Conjugate," Bioorganic & Medicinal Chemistry 9: 2139-2147.

Harris JM and Chess RB, 2003, "Effect of PEGylation on Pharmaceuticals," Nature Reviews in Drug Discovery 2: 214-221.

Harris, "Therapeutic Monoclonals," Biochem. Soc. Transactions 23: 1035-1038 (1995).

Harvill ET and Morrison SL, 1995, "An IgG3-IL2 Fusion Protein Activates Complement, Binds Fc(gamma)RI, Generates LAK Activity and Shows Enhanced Binding to the High Affinity IL-2R," Immunotechnology 1: 95-105.

Havelund S, et al., 2004, "The Mechanism of Protraction of Insulin Determir, a Long-Acting Acylated Analog of Human Insulin," Pharmaceutical Research 21(8): 1498-1504.

Herbst RS, 2009, "Safety, Pharmacokinetics, and Antitumor Activity of AMG 386, a Selective Angiopoietin Inhibitor, in Adult Patients with Advanced Solid Tumors," Journal of Clinical Oncology 27: 3557-3565.

Hiura et. al., "Effects of Ghrelin Administration During Chemotherapy With Advanced Esophageal Cancer Patients," Cancer Jan. 26, 2012, http://onlinelibrary.wiley.com/doi/10.1002/cncr.27430/abstract.

Hoffmann E, et al., 2013, "PK Modulation of Haptenylated Peptides via Non-covalent Antibody Complexation," Journal of Controlled Release 171: 48-56.

Holick MF (editor), 2010, "Vitamin D: Physiology, Molecular Biology, and Clinical Applications," Humana Press pp. 0-1155.

Holt LJ, et al., 2008, "Anti-serum Albumin Domain Antibodies for Extending the Life-Time of Short Lived Drugs," Protein Engineering, Design, & Selection 21(5): 283-288.

(56) References Cited

OTHER PUBLICATIONS

Hoogenboom et al., "Multi-subunit proteins on the surface of filamentous phage: methodologies for displaying antibody (Fab) heavy and light chains," Nucl. Acids Res., 19: 4133-4137 (1991).

Huang A, et al., "A Better Anti-Diabetic Recombinant Human Fibroblast Growth Factor 21 (rhFGF21) Modified with Polyethylene Glycol," PLoS One 6(6): e20669.

Hurle and Gross, "Protein engineering techniques for antibody humanization," Curr. Op. Biotech. 5:428-433 (1994).

Islam I, et al., 1994, "Evaluation of a Vitamin-Cloaking Strategy for Oligopeptide Therapeutics: Biotinylated HIV1-Protease Inhibitors," Journal of Medicinal Chemistry 37: 293-304.

Itoh N, 2014, "FGF21 as a Hepatokine, Adipokine, and Myokine in Metabolism and Diseases," Frontiers in Endocrinology 5: article 107.

Jain, "PEGylation: An Approach for Drug Delivery. A Review," Crit. Rev. Ther. Drug Carrier Syst. 25:403-447 (2008).

Jakobovits et al., "Analysis of homozygous mutant chimeric mice: Deletion of the immunoglobulin heavy-chain joining region blocks B-cell," Proc. Natl. Acad. Sci USA, 90: 2551 (1993).

Jakobovits et al., "Germ Line Transmission and Expression of a Human-Derived Yeast Artificial Chromosome," Nature 362: 255-258 (1993).

Jevsevar S, et al., 2010, "PEGylation of Therapeutic Proteins," Biotechnology Journal 5: 113-128.

Jia ZQ, et al., 2012, "Cardiovascular Effects of a PEGylated Apelin," Peptides 38: 181-188.

Jones et al., Replacing the Complementarity-determining Regions in a Human Antibody with those from a Mouse, Nature 321 :522-525 (1986).

Katre NV, et al., 1987, "Chemical Modification of Recombinant Interleukin 2 by Polyethylene Glycol Increases its Potency in the Murine Meth A Sarcoma Model," Proceedings of the National Academy of Sciences, USA 84: 1487-1491.

Kaul, R. and Balaram, P. (1999), "Stereochemical Control of Peptide Folding," Bioorg Med Chem 7: 105-117.

Kaya T, et al., 2009, "Covalent Labeling of Nuclear Vitamin D Receptor with Affinity Labeling Reagents Containing a Cross-linking Probe at Three Different Positions of the Parent Ligand: Structural and Biochemical Implications," Bioorganic Chemistry 37: 57-63.

Kharitonenkov A and Adams AC, 2014, "Inventing New Medicines: The FGF21 Story," Molecular Metabolism 3: 221-229.

Kharitonenkov and Shanafelt, Curr. Opin. Investig. Drugs 10:359-364 (2009), Abstract Only.

Kharitonenkov et al., "FGF-21 as a novel metabolic regulator," J. Clin. Invest. 115:1627-1635 (2005).

Kim KH and Lee M-S, 2014, "FGF21 as a Stress Hormone: The Roles of FGF21 in Stress Adaptation and the Treatment of Metabolic Diseases," Diabetes & Metabolism Journal 38: 245-251.

Kliewer and Mangelsdorf,"Fibroblast growth factor 21: from pharmacology to physiology1-4," Am. J. Clin. Nutr. 91:254S-257S (2010).

Knight DM, et al., 1993,"Construction and Initial Characterization of a Mouse-Human Chimeric Anti-TNF Antibody," Molecular Immunology 30(16): 1443-1453.

Knutson et al., Biochem Pharmacol 53: 829 (1997).

Kobayashi N, et al., 1992, "Production and Specificity of Antisera Raised against 25-Hydroxyvitamin D3-[C-3]-Bovine Serum Albumin Conjugates," Steroids 57: 488-493.

Kobayashi N, et al., 1994, "Production of a Group-Specific Antibody to 1alpha,25-dihydroxyvitamin D and its Derivatives Having the 1alpha,3beta-dihydroxylated A-Ring Structure," Steroids 59: 404-411.

Kobayashi N, et al., 1994, "Specificity of the Polyclonal Antibodies Raised against a Novel 25-Hydroxyvitamin D3-Bovine Serum Albumin Conjugate Linked through the C11alpha Position," Journal of Steroid Biochemistry & Molecular Biology 48: 567-572.

Kohler et al, "Continuous cultures of fused cells secreting antibody of predefined specificity," Nature, 256: 495 (1975).

Kong J-H, et al., 2010, "Long-Acting Hyaluronate-Exendin 4 Conjugate for the Treatment of Type 2 Diabetes," Biomaterials 31: 4121-4128.

Kontermann R (editor), 2012, "Therapeutic Proteins: Strategies to Modulate Their Plasma Half-lives," Wiley-Blackwell, pp. 0-339.

CARRIERS FOR IMPROVED DRUG DELIVERY

CROSS-REFERENCE

This is a 35 U.S.C. 371 National Phase Application of PCT/US2013/031788 filed Mar. 14, 2013 which claims priority to U.S. Provisional Application No. 61/780,346 filed Mar. 13, 2013, U.S. Provisional Application No. 61/673,874 filed Jul. 20, 2012, and U.S. Provisional Application No. 61/648,516 filed May 17, 2012, the contents of which are incorporated by reference herein in their entirety.

This invention was made with Government support under Grant No. IIP-1248500 awarded by the National Science Foundation, Grant No. W911NF-13-C-0033 awarded by the Department of Defense, and Grant No. 1R43CA174094-01A1 awarded by the National Cancer Institute. The Government has certain rights in this invention.

FIELD OF THE INVENTION

The field of the invention provides the composition and general use of carriers, conjugates, fusions or formulations of therapeutic compounds for the purpose of increasing the potency, absorption, bioavailability or circulating half-life of the compounds by improving pharmacokinetic properties in vivo.

The instant application contains a Sequence Listing that has been submitted electronically in ASCII format and is hereby incorporated by reference in its entirety. Said ASCII copy, created on Nov. 14, 2014, is named XTND002US1_SL.txt and is 17,374 bytes in size.

BACKGROUND OF THE INVENTION

The invention relates to improving the potency, absorption or pharmacokinetic properties of therapeutic compounds. The addition of poly(ethylene glycol) or (PEG) is a known method of increasing the half-life of some compounds by reducing kidney clearance, reducing aggregation, and diminishing potentially unwanted immune recognition (Jain, *Crit. Rev. Ther. Drug Carrier Syst.* 25:403-447 (2008)). The PEG is typically used at a considerably large size (20-40 kDa) to maximize the half-life in circulation. This can be accomplished by using either a single large PEG or multiple smaller PEGs attached to the compound. (Clark et al. *J. Biol. Chem.* 271:21969-21977 (1996); Fishburn, *J. Pharm. Sci.* 97:4167-4183 (2008)).

Absorption is a primary focus in drug development and medicinal chemistry since a drug must be absorbed before any medicinal effects can take place. A drug's pharmacokinetic profile can be affected by many factors. Additionally, the absorption properties of therapeutic compounds vary significantly from compound to compound. Some therapeutic compounds are poorly absorbed following oral or dermal administration. Other therapeutic compounds, such as most peptide- and protein-based therapeutics, cannot be administered orally. Alternate routes of administration such as intravenous, subcutaneous, or intramuscular injections are routinely used for some of compounds; however, these routes often result in slow absorption and exposure of the therapeutic compounds to enzymes that can degrade them, thus requiring much higher doses to achieve efficacy.

A number of peptides have been identified as therapeutically promising. The chemical and biological properties of peptides and proteins make them attractive candidates for use as therapeutic compounds. Peptides and proteins are naturally-occurring molecules made up of amino acids and are involved in numerous physiological processes. Peptides and proteins display a high degree of selectivity and potency, and may not suffer from potential adverse drug-drug interactions or other negative side effects. Thus peptides and proteins hold great promise as a highly diverse, highly potent, and highly selective class of therapeutic compounds with low toxicity. Peptides and proteins, however, may have short in vivo half-lives. For such peptides, this may be a few minutes. This may render them generally impractical, in their native form, for therapeutic administration. Additionally, peptides may have a short duration of action or poor bioavailability.

Fibroblast growth factor 21 (SEQ ID:2) is a protein that circulates in serum. Encoded by the FGF21 gene, it is a member of a family of atypical fibroblast growth factors (FGFs), which include FGF19 and FGF23. It lacks the conventional FGF heparin-binding domain. FGF family members possess broad mitogenic and cell survival activities and are involved in a variety of biological processes including embryonic development, cell growth, morphogenesis, tissue repair, tumor growth and invasion. FGF21 is specifically induced by HMGCS2 activity. FGF21 stimulates glucose uptake in adipocytes but not in other cell types. This effect is additive to the activity of insulin.

In vitro studies indicate that FGF21 prefers binding to the FGFR1c/b-Klotho receptor complex over those containing other FGFR isotypes (Kliewer and Mangelsdorf, *Am. J. Clin. Nutr.* 91:254S-257S (2010)). FGF21 promotes glucose uptake by adipocytes in vitro. Administration of FGF21 to diabetic animals reduces circulating glucose levels while excess FGF21 does not induce hypoglycemia as seen with administration of excess insulin (Kharitonenkov and Shanafelt, *Curr. Opin. Investig. Drugs* 10:359-364 (2009)). Therefore, FGF21 is a promising therapeutic protein for the treatment of diabetes. FGF21, however, was administered frequently to see therapeutic benefits in an animal model (Kharitonenkov et al., *J. Clin. Invest.* 115:1627-1635 (2005)). FGF21 in its natural state has an extremely short half-life in serum (1.1 hr) making exogenous addition of FGF21 in its natural state not clinically practical as a treatment (see WO03/011213). Additionally, FGF21 exhibits poor bioavailability when injected subcutaneously. In a comparative pharmacokinetic study, 1 mg/kg of FGF21 was injected either intravenously (IV) or subcutaneously (SC) and the concentration of FGF21 was analyzed over time. The results showed a significant reduction in bioavailability using a subcutaneous route of administration (Cmax 73 nM) compared to the intravenous route (Cmax of 1890 nM; see Table 1 in Xu J et al., 2009. Am J Physiol Endocrinol Metab 297: E1105-E1114). The foregoing references are incorporated herein by reference in their entirety.

Ghrelin peptide (SEQ ID NO:5) is naturally secreted from the stomach in mammals into circulation to stimulate appetite and release of growth hormone. Ghrelin stimulates the release of growth hormone (GH) from the pituitary gland through the cellular receptor GHS-R and plays important roles in energy homeostasis. In addition, ghrelin acts directly on the central nervous system to decrease sympathetic nerve activity. Ghrelin receptors (GHS-Rs) are concentrated in the hypothalamus-pituitary unit. GHS-R is distributed in peripheral tissues, including the heart, lung, liver, kidney, pancreas, stomach, small and large intestines, adipose, and immune cells.

Ghrelin has been used therapeutically to increase weight and lean body mass in patients suffering from cachexia or involuntary weight loss resulting from a chronic disease such as cancer (Hiura et. al., *Cancer* Jan. 26, 2012, http://onlinelibrary.wiley.com/doi/10.1002/cncr.27430/abstract). Ghrelin, however, has a naturally short half-life of 11 mins in humans (Akamizu et al., *Eur J Endocrinol* 150:447-55 (2004)) and thus must be dosed often to see therapeutic effects.

Infliximab (Remicade®, Janssen Biotech Inc., U.S. Pat. No. 5,919,452 and US 2002/0141996, incorporated herein by reference in their entirety) is a monoclonal antibody that binds tumor necrosis factor alpha (TNF-α, SEQ ID:10) that is used to treat autoimmune diseases. Infliximab was approved by the U.S. Food and Drug Administration (FDA) for the treatment of psoriasis, Crohn's disease, ankylosing spondylitis, psoriatic arthritis, rheumatoid arthritis, and ulcerative colitis. TNF-α is a chemical messenger (cytokine) and a key part of the autoimmune reaction. Infliximab is administered intravenously by a healthcare professional and is not approved for subcutaneous dosing.

SUMMARY OF THE INVENTION

The invention provides carriers that enhance the absorption, stability, half-life, duration of effect, potency, or bioavailability of therapeutic compounds. The carriers comprise targeting groups that bind the Vitamin D Binding protein (DBP), conjugation groups for coupling the targeting groups to the therapeutic compounds, and optional scaffolding moieties.

In an embodiment of the invention, the targeting group is vitamin D, a vitamin D analog, a vitamin D-related metabolite, an analog of a vitamin D related-metabolite, a peptide that binds DBP, an anti-DBP antibody, an anti-DBP antibody derivative, a nucleotide aptamer that binds DBP, or a small carbon-based molecule that binds DBP.

In another embodiment, the coupling group is an amine-reactive group, a thiol-reactive group, a maleimide group, a thiol group, an aldehyde group, an NHS-ester group, a 4-nitrophenyl ester, an acylimidazole, a haloacetyl group, an iodoacetyl group, a bromoacetyl groups, a SMCC group, a sulfo SMCC group, a carbodiimide group and bifunctional cross-linkers such as NHS-Maleimido or combinations thereof. The coupling groups of the invention can promote thiol linkages, amide linkages, oxime linkages, hydrazone linkages, thiazolidinone linkages or utilizes cycloaddition reactions (e.g. click chemistry) to couple the carrier or targeting group to a therapeutic compound.

In another embodiment, the pharmaceutical carrier further comprising a scaffold moiety, comprising poly(ethylene glycol), polylysine, polyethyleneimine, poly(propyleneglycol), a peptide, serum albumin, thioredoxin, an immunoglobulin, an amino acid, a nucleic acid, a glycan, a modifying group that contains a reactive linker, a water-soluble polymer, a small carbon chain linker, or an additional therapeutic moiety.

In another embodiment, the scaffold moiety is between about 100 Da. and 200,000 Da. In preferred embodiments, the scaffold moiety is between about 100 Da. and 20,000 Da., 200 Da. and 15,000 Da., 300 Da. and 10,000 Da., 400 Da. and 9,000 Da., 500 Da. and 5,000 Da., 600 Da. and 2,000 Da., 1000 Da. and 200,000 Da., 5000 Da. and 100,000 Da., 10,000 Da. and 80,000 Da., 20,000 Da. and 60,000 Da., or 20,000 Da. and 40,000 Da.

The invention provides a pharmaceutical composition comprising a therapeutic compound conjugated to, fused to, or formulated with a carrier. The carrier comprises a targeting group that binds DBP and increases the absorption, bioavailability, or half-life of the therapeutic compound in circulation. The pharmaceutical compositions of the invention may comprise two or more therapeutic compounds conjugated to a single carrier. The pharmaceutical compositions of the invention may comprise two or more carriers conjugated to a therapeutic compound.

In one embodiment, the targeting group in the pharmaceutical composition is vitamin D, a vitamin D analog, a vitamin D-related metabolite, an analog of a vitamin D-related metabolite, a peptide that binds DBP, an anti-DBP antibody, an anti-DBP antibody derivative, a nucleotide aptamer that binds DBP, or a small, carbon-based molecule that binds DBP.

In another embodiment, the pharmaceutical composition further comprises a scaffold moiety. In a preferred embodiment, the scaffold moiety is poly(ethylene glycol), polylysine, polyethyleneimine, poly(propyleneglycol), a peptide, serum albumin, thioredoxin, an immunoglobulin, an amino acid, a nucleic acid, a glycan, a modifying group that contains a reactive linker, a water-soluble polymer, a small carbon chain linker, or an additional therapeutic compound.

The pharmaceutical compositions of the invention may comprise small molecules, chemical entities, nucleic acids, nucleic acid derivatives, peptides, peptide derivatives, naturally-occurring proteins, non-naturally-occurring proteins, peptide-nucleic acids (PNA), stapled peptides, morpholinos, phosphorodiamidate morpholinos, antisense drugs, RNA-based silencing drugs, aptamers, glycoproteins, enzymes, hormones, cytokines, interferons, growth factors, blood coagulation factors, antibodies, antibody fragments, antibody derivatives, toxin-conjugated antibodies, metabolic effectors, analgesics, antipyretics, anti-inflammatory agents, antibiotics, anti-microbial agents, anti-viral agents, anti-fungal drugs, musculoskeletal drugs, cardiovascular drugs, renal drugs, pulmonary drugs, digestive disease drugs, hematologic drugs, urologic drugs, metabolism drugs, hepatic drugs, neurological drugs, anti-diabetes drugs, anti-cancer drugs, drugs for treating stomach conditions, drugs for treating colon conditions, drugs for treating skin conditions, or drugs for treating lymphatic conditions.

In a preferred embodiment, the pharmaceutical composition comprises a protein having FGF21 activity comprising an amino acid sequence with at least a 90% sequence identity to SEQ ID NO:2. In another preferred embodiment, the targeting group is Vitamin D. In another preferred embodiment, the scaffold moiety is poly(ethylene glycol).

In a most preferred embodiment, the invention contemplates a pharmaceutical composition comprising a protein having FGF21 activity comprising an amino acid sequence with at least a 90% sequence identity to SEQ ID NO:2, a scaffold moiety that is poly(ethylene glycol), and a targeting group that is Vitamin D. In this embodiment, the targeting group increases the absorption, bioavailability, or the half-life of the therapeutic compound in circulation. In another most preferred embodiment, the invention contemplates a pharmaceutical composition comprising a protein having FGF21 activity and the amino acid sequence of SEQ ID NO:2.

In a preferred embodiment, the pharmaceutical composition comprises a protein having ghrelin activity comprising an amino acid sequence with at least a 90% sequence identity to SEQ ID NO:5. In another preferred embodiment, the targeting group is Vitamin D. In another preferred embodiment, the scaffold moiety is poly(ethylene glycol).

In a most preferred embodiment, the invention contemplates a pharmaceutical composition comprising a protein having ghrelin activity comprising an amino acid sequence with at least a 90% sequence identity to SEQ ID NO:5, a scaffold moiety that is poly(ethylene glycol), and a targeting group that is Vitamin D. In this embodiment, the targeting group increases the absorption, bioavailability, or the half-life of the therapeutic compound in circulation. In another most preferred embodiment, the invention contemplates a pharmaceutical composition comprising a protein having ghrelin activity and the amino acid sequence of SEQ ID NO:5.

In one embodiment, the pharmaceutical composition comprises an antibody. In a preferred embodiment, the antibody is an anti-TNF-α antibody that specifically binds a protein having an amino acid sequence of at least a 90% sequence identity to SEQ ID NO:10. In a more preferred embodiment, the anti-TNF-α antibody specifically binds a protein having the amino acid sequence of SEQ ID NO:10. In another preferred embodiment, the targeting group is Vitamin D. In another preferred embodiment, the scaffold moiety is poly(ethylene glycol).

In a most preferred embodiment, the invention comprises an anti-TNF-α antibody that specifically binds a protein having an amino acid sequence with at least a 90% sequence identity to SEQ ID NO:10, a scaffold moiety that is poly(ethylene glycol), and a targeting group that is Vitamin D. In this embodiment, the targeting group increases the absorption, bioavailability, or the half-life of the therapeutic compound in circulation.

In certain embodiments, the present invention provides carriers that include those of formula I:

         I

Wherein:
B is a targeting group selected from vitamin D, a vitamin D analog, a vitamin D-related metabolite, an analog of a vitamin D related-metabolite, a peptide that binds DBP, an anti-DBP antibody, an anti-DBP antibody derivative, a nucleotide aptamer that binds DBP, or a small carbon-based molecule that binds DBP;
S is a scaffold moiety, comprising poly(ethylene glycol), polylysine, polyethyleneimine, poly(propy or thiol-reactive coupling groups. Maleimide is a useful coupling group for use in coupling to sulfhydryl groups such as on a free cysteine residue that can be site-specifically engineered into a peptide or protein in a desired position. Other coupling groups such as NHS— that target amine groups or aldehyde that can be used to site specifically attach to the N-terminus of a therapeutic compound are well known to those skilled in the art. Other more specialized coupling groups are contemplated and could be substituted by one skilled in the art.

In some methods, the targeting group is vitamin D, a vitamin D analog, a vitamin D-related metabolite, an analog of a vitamin D-related metabolite, a peptide that binds DBP, an anti-DBP antibody, an anti-DBP antibody derivative, a nucleotide aptamer that binds DBP, or a small carbon-based molecule that binds DBP.

In other embodiments, methods of manufacturing pharmaceutical compositions further comprise conjugating a scaffold moiety to the targeting group or drug. The scaffold moiety may be poly(ethylene glycol), polylysine, polyethyleneimine, poly(propyleneglycol), a peptide, serum albumin, thioredoxin, an immunoglobulin, an amino acid, a nucleic acid, a glycan, a modifying group that contains a reactive linker, a water-soluble polymer, a small carbon chain linker, or an additional therapeutic compound.

DETAILED DESCRIPTION OF THE INVENTION

Figure 1:
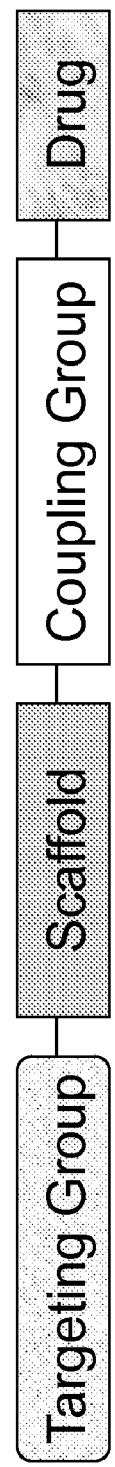
FIG. 1: Schematic diagram showing the general structure of a carrier coupled to a drug. The carrier comprises a targeting group, a scaffold, and optionally, a coupling group.

The invention provides carrier molecules that are covalently attached to, fused to or formulated with therapeutic proteins, peptides, nucleic acids or small molecules for the purpose of improving the potency, absorption, bioavailability, circulating half-life or pharmacokinetic properties of the therapeutic compounds. In certain embodiments, the carriers comprise a targeting group, a scaffold, and a coupling group. In other embodiments, the carriers lack a scaffold, which acts, among other things, as a "spacer" between the targeting group and the therapeutic compound.

The carriers are designed to be suitable for use in humans and animals. The carriers serve the purpose of improving the pharmacokinetic properties of a biological or chemical entity that is coupled to, conjugated to, fused to, or formulated with the carrier. This occurs through the interaction of the targeting group with vitamin D binding protein (DBP), which can actively transport molecules quickly and effectively from the site of administration to the circulating plasma, thereby reducing exposure of the drug to degradative enzymes. The carriers, by binding to DBP, also improve the circulating half-life of the drug, thus increasing the potency and therapeutic efficacy of the drug by preventing kidney filtration. Methods for conjugating the carrier to therapeutic compounds described herein are known in the art. By way of example, conjugation using the coupling groups of the invention may be carried out using the compositions and methods described in WO93/012145 (Atassi et al.) and U.S. Pat. No. 7,803,777 (Defrees et al.), each of which are incorporated by reference herein in their entirety.

In describing and claiming one or more embodiments of the present invention, the following terminology will be used in accordance with the definitions described below.

The term "absorption" is the movement of a drug into the bloodstream. A drug needs to be introduced via some route of administration (e.g. oral, topical or dermal) or in a specific dosage form such as a tablet, capsule or liquid. Intravenous therapy, intramuscular injection, and enteral nutrition provide less variability in absorption and bioavailability is often near 100%. The fastest route of absorption is inhalation.

An "antagonist" refers to a molecule capable of neutralizing, blocking, inhibiting, abrogating, reducing or interfering with the activities of a particular or specified protein, including its binding to one or more receptors in the case of a ligand, or binding to one or more ligands in case of a receptor. Antagonists include antibodies and antigen-binding fragments thereof, proteins, peptides, glycoproteins, glycopeptides, glycolipids, polysaccharides, oligosaccharides, nucleic acids, bioorganic molecules, peptidomimetics, pharmacological agents and their metabolites, transcriptional and translation control sequences, and the like. Antagonists also include small molecule inhibitors of proteins, hormones, or other bioactive molecules. Antagonists may be fusion proteins, receptor molecules, antisense molecules, aptamers, ribozymes, or derivatives that bind specifically to the proteins, hormones, or other bioactive molecules and thereby sequester its binding to its target.

"Antibodies" (Abs) and "immunoglobulins" (Igs) refer to glycoproteins having similar structural characteristics. While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

"Aptamers" are nucleic acid-based compounds that have been selected to bind a specific target. An example of an aptamer-based therapeutic compound can be found in WO07/035922, incorporated by reference herein in its entirety.

The term "bioavailability" refers to the fraction of an administered dose of unchanged drug that reaches the systemic circulation, one of the principal pharmacokinetic properties of drugs. When a medication is administered intravenously, its bioavailability is 100%. When a medication is administered via other routes (such as orally), its bioavailability generally decreases (due to incomplete absorption and first-pass metabolism) or may vary from patient to patient. Bioavailability is an important parameter in pharmacokinetics that is considered when calculating dosages for non-intravenous routes of administration.

"Carriers" are compounds that can be conjugated to, fused to, coupled to or formulated with therapeutic compounds to improve the absorption, half-life, bioavailability, pharmacokinetic or pharmacodynamic properties of the drugs. They comprise a targeting group, a coupling group, and optionally, a scaffold moiety.

An "effective amount" refers to an amount of therapeutic compound that is effective, at dosages and for periods of time necessary, to achieve the desired therapeutic or prophylactic result. A "therapeutically effective amount" of a therapeutic compound may vary according to factors such as the disease state, age, sex, and weight of the individual, and the ability of the antibody to elicit a desired response in the individual. A therapeutically effective amount may be measured, for example, by improved survival rate, more rapid recovery, or amelioration, improvement or elimination of symptoms, or other acceptable biomarkers or surrogate markers. A therapeutically effective amount is also one in which any toxic or detrimental effects of the therapeutic compound are outweighed by the therapeutically beneficial effects. A "prophylactically effective amount" refers to an amount of therapeutic compound that is effective, at dosages and for periods of time necessary, to achieve the desired prophylactic result. Typically, but not necessarily, since a prophylactic dose is used in subjects prior to or at an earlier stage of disease, the prophylactically effective amount will be less than the therapeutically effective amount.

"Half-life" is a scientific term known in the art that refers to the amount of time that elapses when half of the quantity of a test molecule is no longer detected. An in vivo half-life refers to the time elapsed when half of the test molecule is no longer detectable in circulating serum or tissues of a human or animal.

A "hormone" is a biological or chemical messenger from one cell (or group of cells) to another cell that has signaling capability. As described herein, hormones for use in the invention may be peptides, steroids, pheromones, interleukins, lymphokines, cytokines, or members of other hormone classes known in the art.

"Homologs" are bioactive molecules that are similar to a reference molecule at the nucleotide sequence, peptide sequence, functional, or structural level. Homologs may include sequence derivatives that share a certain percent identity with the reference sequence. Thus, in one embodiment, homologous or derivative sequences share at least a 70 percent sequence identity. In a preferred embodiment, homologous or derivative sequences share at least an 80 or 85 percent sequence identity. In a more preferred embodiment, homologous or derivative sequences share at least an 86, 87, 88, 89, 90, 91, 92, 93, 94, 95, 96, 97, 98, or 99 percent sequence identity. Homologous or derivative nucleic acid sequences may also be defined by their ability to remain bound to a reference nucleic acid sequence under high stringency hybridization conditions. Homologs having a structural or functional similarity to a reference molecule may be chemical derivatives of the reference molecule. Methods of detecting, generating, and screening for structural and functional homologs as well as derivatives are known in the art.

"Hybridization" generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al, Current Protocols in Molecular Biology, Wiley Interscience Publishers, (1995).

An "individual," "subject" or "patient" is a vertebrate. In certain embodiments, the vertebrate is a mammal. Mammals include, but are not limited to, primates (including human and non-human primates) and rodents (e.g., mice, hamsters, guinea pigs, and rats). In certain embodiments, a mammal is a human. A "control subject" refers to a healthy subject who has not been diagnosed as having a disease, dysfunction, or condition that has been identified in an individual, subject, or patient. A control subject does not suffer from any sign or symptom associated with the disease, dysfunction, or condition.

A "medicament" is an active drug that has been manufactured for the treatment of a disease, disorder, or condition.

"Morpholinos" are synthetic molecules that are non-natural variants of natural nucleic acids that utilize a phosphorodiamidate linkage, described in U.S. Pat. No. 8,076,476, incorporated by reference herein in its entirety.

"Nucleic acids" are any of a group of macromolecules, either DNA, RNA, or variants thereof, that carry genetic information that may direct cellular functions. Nucleic acids may have enzyme-like activity (for instance ribozymes) or may be used to inhibit gene expression in a subject (for instance RNAi). The nucleic acids used in the inventions described herein may be single-stranded, double-stranded, linear or circular. The inventions further incorporate the use of nucleic acid variants including, but not limited to, aptamers, PNA, Morpholino, or other non-natural variants of nucleic acids. By way of example, nucleic acids useful for the invention are described in U.S. Pat. No. 8,076,476, incorporated by reference herein in its entirety.

"Patient response" or "response" can be assessed using any endpoint indicating a benefit to the patient, including, without limitation, (1) inhibition, to some extent, of disease progression, including slowing down and complete arrest; (2) reduction in the number of disease episodes and/or symptoms; (3) inhibition (i.e., reduction, slowing down or complete stopping) of a disease cell infiltration into adjacent peripheral organs and/or tissues; (4) inhibition (i.e. reduction, slowing down or complete stopping) of disease spread; (5) decrease of an autoimmune condition; (6) favorable change in the expression of a biomarker associated with the disorder; (7) relief, to some extent, of one or more symptoms associated with a disorder; (8) increase in the length of disease-free presentation following treatment; or (9) decreased mortality at a given point of time following treatment.

As used herein, the term "peptide" is any peptide comprising two or more amino acids. The term peptide includes short peptides (e.g., peptides comprising between 2-14 amino acids), medium length peptides (15-50) or long chain peptides (e.g., proteins). The terms peptide, medium length peptide and protein may be used interchangeably herein. As used herein, the term "peptide" is interpreted to mean a polymer composed of amino acid residues, related naturally occurring structural variants, and synthetic non-naturally occurring analogs thereof linked via peptide bonds, related naturally-occurring structural variants, and synthetic non-naturally occurring analogs thereof. Synthetic peptides can be synthesized, for example, using an automated peptide synthesizer. Peptides can also be synthesized by other means such as by cells, bacteria, yeast or other living organisms. Peptides may contain amino acids other than the 20 gene-encoded amino acids. Peptides include those modified either by natural processes, such as processing and other post-translational modifications, but also by chemical modification techniques. Such modifications are well described in basic texts and in more detailed monographs, and are well-known to those of skill in the art. Modifications occur anywhere in a peptide, including the peptide backbone, the amino acid side-chains, and the amino or carboxyl termini.

As used herein, a "pharmaceutically acceptable carrier" or "therapeutic effective carrier" is aqueous or nonaqueous (solid), for example alcoholic or oleaginous, or a mixture thereof, and can contain a surfactant, emollient, lubricant, stabilizer, dye, perfume, preservative, acid or base for adjustment of pH, a solvent, emulsifier, gelling agent, moisturizer, stabilizer, wetting agent, time release agent, humectant, or other component commonly included in a particular form of pharmaceutical composition. Pharmaceutically acceptable carriers are well known in the art and include, for example, aqueous solutions such as water or physiologically buffered saline or other solvents or vehicles such as glycols, glycerol, and oils such as olive oil or injectable organic esters. A pharmaceutically acceptable carrier can contain physiologically acceptable compounds that act, for example, to stabilize or to increase the absorption of specific inhibitor, for example, carbohydrates, such as glucose, sucrose or dextrans, antioxidants such as ascorbic acid or glutathione, chelating agents, low molecular weight proteins or other stabilizers or excipients.

The term "pharmacokinetics" is currently defined as the time course of the absorption, distribution, metabolism, and excretion of a therapeutic compound. Improved "pharmacokinetic properties" are defined as: improving one or more of the pharmacokinetic properties as desired for a particular therapeutic compound. Examples include but are not limited to: reducing elimination through metabolism or secretion, increasing drug absorption, increasing half-life, and/or increasing bioavailability.

"PNA" refers to peptide nucleic acids with a chemical structure similar to DNA or RNA. Peptide bonds are used to link the nucleotides or nucleosides together.

"Scaffolds" are molecules to which other molecules can be covalently or or non-covalently attached or formulated. The scaffolds of the invention may act as "spacers" or "linkers" between the targeting group and the drug. Scaffolds may also contain a reactive linker or may have beneficial therapeutic properties in addition to the drug. Thus, the scaffolds of the invention may be, for example, PEG, serum albumin, thioredoxin, an immunoglobulin, a modifying group that contains a reactive linker, a water-soluble polymer, or a therapeutic compound.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures.

"Stringent conditions" or "high stringency conditions", as defined herein, can be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μl/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

The "therapeutic compounds" disclosed herein refer to small molecules, chemical entities, nucleic acids, nucleic acid derivatives, peptides, peptide derivatives, naturally-occurring proteins, non-naturally-occurring proteins, glycoproteins, and steroids that are administered to subjects to treat a diseases or dysfunctions or to otherwise affect the health of individuals. Non-limiting examples of therapeutic compounds include polypeptides such as enzymes, hormones, cytokines, antibodies or antibody fragments, antibody derivatives, drugs that affect metabolic function, as well as organic compounds such as analgesics, antipyretics, anti-inflammatory agents, antibiotics, anti-viral compounds, anti-fungal compounds, cardiovascular drugs, drugs that affect renal function, electrolyte metabolism, drugs that act on the central nervous system, chemotherapeutic compounds, receptor agonists and receptor antagonists. Therapeutic compounds include, for example, extracellular molecules such as serum factors including, but not limited to, plasma proteins such as serum albumin, immunoglobulins, apolipoproteins or transferrin, or proteins found on the surface of erythrocytes or lymphocytes. Thus, exemplary therapeutic compounds include small molecules, chemical entities, nucleic acids, nucleic acid derivatives, peptides, peptide derivatives, naturally-occurring proteins, non-naturally-occurring proteins, peptide-nucleic acids (PNA), stapled peptides, phosphorodiamidate morpholinos, antisense drugs, RNA-based silencing drugs, aptamers, glycoproteins, enzymes, hormones, cytokines, interferons, growth factors, blood coagulation factors, antibodies, antibody fragments, antibody derivatives, toxin-conjugated antibodies, metabolic effectors, analgesics, antipyretics, anti-inflammatory agents, antibiotics, anti-microbial agents, anti-viral agents, anti-fungal drugs, musculoskeletal drugs, cardiovascular drugs, renal drugs, pulmonary drugs, digestive disease drugs, hematologic drugs, urologic drugs, metabolism drugs, hepatic drugs, neurological drugs, anti-diabetes drugs, anti-cancer drugs, drugs for treating stomach conditions, drugs for treating colon conditions, drugs for treating skin conditions, and drugs for treating lymphatic conditions. The term "therapeutic compound" as used herein has essentially the same meaning as the terms "drug" or "therapeutic agent."

As used herein, "treatment" refers to clinical intervention in an attempt to alter the natural course of the individual or cell being treated, and can be performed before or during the course of clinical pathology. Desirable effects of treatment include preventing the occurrence or recurrence of a disease or a condition or symptom thereof, alleviating a condition or symptom of the disease, diminishing any direct or indirect pathological consequences of the disease, decreasing the rate of disease progression, ameliorating or palliating the disease state, and achieving remission or improved prognosis. In some embodiments, methods and compositions of the invention are useful in attempts to delay development of a disease or disorder.

A "vitamin" is a recognized term in the art and is defined as a fat-soluble or water-soluble organic substance essential in minute amounts for normal growth and activity of the body and is obtained naturally from plant and animal foods or supplements.

"Vitamin D" is a group of fat-soluble secosteroids. Several forms (vitamers) of vitamin D exist. The two major forms are vitamin $D_2$ or ergocalciferol, and vitamin $D_3$ or cholecalciferol. Vitamin D without a subscript refers to either $D_2$ or $D_3$ or both. In humans, vitamin D can be ingested as cholecalciferol (vitamin $D_3$) or ergocalciferol (vitamin $D_2$). Additionally, humans can synthesize it from cholesterol when sun exposure is adequate.

"Vitamin D binding protein" or "DBP" is a naturally circulating serum protein found in all mammals that, among other activities, can bind to and transport vitamin D and its analogs to sites in the liver and kidney where the vitamin is modified to its active form, and it retains vitamin D in its various forms in circulation for, on average, 30 days in humans. A DBP protein sequence is disclosed in SEQ ID NO:7 and an exemplary nucleic acid sequence encoding the DBP protein sequence is disclosed in SEQ ID NO:8. DBP has multiple naturally-occurring isoforms. Exemplary isoforms are available in the public sequence databases (e.g. Accession Nos. NM_001204306.1, NM_001204307.1, NM_000583.3, BC036003.1, M12654.1, X03178.1, AK223458, P_001191235.1, NP_000574.2, AAA61704.1, AAD13872.1, NP_001191236.1, AAA19662.2, I54269, P02774.1, EAX05645.1, AAH57228.1, AAA52173.1, AAB29423.1, AAD14249.1, AAD14250.1, and BAD97178.1).

The invention contemplates the use of DBP variants and homologs that contain conservative or non-conservative amino acid substitutions that substantially retain DBP activity. DBP binding molecules or functional DBP variants may be identified using known techniques and characterized using known methods (Bouillon et al., *J Bone Miner Res.* 6(10): 1051-7 (1991), Teegarden et. al., *Anal. Biochemistry* 199(2): 293-299 (1991), McLeod et al, *J Biol Chem.* 264(2):1260-7 (1989), Revelle et al., *J. Steroid Biochem.* 22:469-474 (1985)) The foregoing references are incorporated by reference herein in their entirety.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like.

The invention provides effective routes for administration of proteins, peptides, other biologics, nucleic acids, and small molecule drugs. The invention further provides effective routes of drug administration via transdermal, oral, parenteral, subcutaneous, intracutaneous, intravenous, intramuscular, intraarticular, intrasynovial, intrasternal, intrathecal, intralesional, intracranial injection, infusion, inhalation, ocular, topical, rectal, nasal, buccal, sublingual, vaginal, or implanted reservoir modes.

In addition, the inventions described herein provide compositions and methods for maintaining target binding activity, i.e. pharmacodynamics (PD), for therapeutic compounds. It further provides compositions and methods for improving the pharmacokinetic (PK) profiles of therapeutic compounds as described herein. The invention further provides compositions and methods for improved drug absorption profiles as compared to the drug absorption profiles for the drugs using the same routes of administration or different routes of administration but without the inventions described herein.

The invention further provides compositions and methods for improved drug bioavailability profiles as compared to the drug bioavailability profiles for the drugs using the same routes of administration or different routes of administration but without the inventions described herein. The invention further provides compositions and methods for improved drug half-life profiles as compared to the drug half-life profiles for the drugs using the same routes of administration or different routes of administration but without the inventions described herein.

The invention also provides alternative routes of drug administration that are more cost-effective and favorable to the patients when compared to the drugs without the inventions described herein.

The invention provides compositions and methods for using molecules that serve as carriers that can be conjugated to, fused to, or formulated with active therapeutic compounds for the purpose of improving the absorption, half-life, bioavailability, or pharmacokinetic properties of the drugs. The carriers have the properties of binding to the body's natural DBP. One aspect of the invention provides use of the natural DBP to transport the carrier-drug complex from the site of administration to the circulating serum. Another aspect of the invention is the use of the natural DBP to retain a drug in circulation for an extended period of time. This can prevent its excretion from the body and increase the exposure of the therapeutic compound in the body to achieve a longer lasting therapeutic effect. In another aspect of the invention, a smaller dose of drug is required when conjugated to, fused to or formulated with the carrier, when compared to the unconjugated, unfused or unformulated drug. Another aspect of the invention is the use of a carrier to replace the function of a much larger PEG compound when coupled to a therapeutic compound. This can improve the pharmacokinetic profile and efficacy of the conjugated, fused or formulated compound.

The invention provides a carrier molecule that is preferably composed of one or more parts or components. In one embodiment, the carrier comprises a targeting group and a coupling group for attaching the targeting group to the therapeutic compound. In another embodiment, the carrier comprises a scaffold moiety that is linked to the targeting group and the therapeutic compound. The targeting group is vitamin D, a vitamin D analog, a vitamin D-related metabolite, a vitamin D-related metabolite analog, or another molecule that can bind to or interact with the vitamin D binding protein (DBP). In one embodiment, the targeting group is an antibody or antibody derivative, a peptide designed to bind DBP or a fragment thereof, a peptide derived from a phage display or other peptide library selected against DBP or a fragment thereof, a nucleotide aptamer that binds DBP, a small molecule designed to bind DBP or derived from a chemical library selected against DBP, or a fragment thereof.

The therapeutic compound carrier conjugates of the invention typically have about 1, 2, 3, 4, 5, 6, 7, 8, 9, or 10 targeting groups individually attached to a therapeutic compound. In one embodiment, the carrier conjugate of the invention will comprise about 4 targeting groups individually attached to a therapeutic compound, or about 3 targeting groups individually attached to a therapeutic compound, or about 2 targeting groups individually attached to a therapeutic compound, or about 1 targeting group attached to a therapeutic compound. The structure of each of the targeting groups attached to the therapeutic compound may be the same or different. In a preferred embodiment, one or more targeting groups are stably attached to the therapeutic compound at the N-terminus of a therapeutic protein. In another preferred embodiment, one or more targeting groups are stably attached to the therapeutic protein at the C-terminus of a therapeutic protein. In other preferred embodiments, one or more targeting groups may be stably attached to other sites on the therapeutic protein. For example, a therapeutic compound carrier conjugate may comprise a targeting group attached to the N-terminus and additionally a targeting group attached to a lysine residue. In another embodiment, a therapeutic compound carrier conjugate has a targeting group attached to a therapeutic protein via a modification such as a sugar residue as part of a glycosylation site, or on an acylation site of a peptide or attached to a phosphorylation site or other natural or non-natural modifications that are familiar to one skilled in the art. Also contemplated are attachment sites using a combination of sites mentioned above. One preferred embodiment of the present invention comprises a targeting group that is attached to the therapeutic compound at one specific site on a therapeutic compound. In another preferred embodiment, the attachment site on a protein may be a cysteine, lysine, the N-terminus or C-terminus.

In another embodiment, the scaffold is a pharmaceutically acceptable carrier. In preferred embodiments, the scaffold is poly(ethylene glycol), polylysine, polyethyleneimine, poly(propyleneglycol), a peptide, serum albumin, thioredoxin, an immunoglobulin, an amino acid, a nucleic acid, a glycan, a modifying group that contain a reactive linker, a water-soluble polymer, a small carbon chain linker, or an additional therapeutic moiety.

In one embodiment, water-soluble scaffold moieties have some detectable degree of solubility in water. Methods to detect and/or quantify water solubility are well known in the art. Exemplary water-soluble polymers include peptides, saccharides, poly(ethers), poly(amines), poly(carboxylic acids) and the like.

Peptides can have mixed sequences or be composed of a single amino acid, e.g., poly(lysine). An exemplary polysaccharide is poly(sialic acid). An exemplary poly(ether) is poly(ethylene glycol), e.g. m-PEG. Poly(ethyleneimine) is an exemplary polyamine, and poly(acrylic) acid is a representative poly(carboxylic acid). The polymer backbone of the water-soluble polymer can be poly(ethylene glycol) (i.e. PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein. The polymer backbone can be linear or branched.

Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(-PEG-OH)$_m$ in which R represents the core moiety, such as glycerol or pentaerythritol, and m represents the number of arms. Multiarmed PEG molecules, such as those described in U.S. Pat. No. 5,932,462, which is incorporated by reference herein in its entirety, can also be used as the polymer backbone.

Many other polymers are also suitable for the invention. Polymer backbones that are non-peptidic and water-soluble, with from 2 to about 300 termini, are particularly useful in the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), polyvinylpyrrolidone), polylysine, polyethyleneimine, poly(hydroxypropylmethacrylamide), poly(α-hydroxy acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures thereof. Although the molecular weight of each chain of the polymer backbone can vary, it is typically in the range of about 100 Da to about 100,000 Da.

In other embodiments, the scaffold moiety may be a peptide, serum albumin, thioredoxin, an immunoglobulin, an amino acid, a nucleic acid, a glycan, a modifying group that contains a reactive linker, a water-soluble polymer, a small carbon chain linker, or an additional therapeutic compound. In one embodiment, the scaffold moieties are non-toxic to humans and animals. In another embodiment, the scaffolds are endogenous serum proteins. In another embodiment, the scaffold moieties are water-soluble polymers. In another embodiment, the scaffolds are non-naturally-occurring polymers. In another embodiment, the scaffolds are naturally-occurring moieties that are modified by covalent attachment to additional moieties (e.g., PEG, poly(propylene glycol), poly(aspartate), biomolecules, therapeutic moieties, or diagnostic moieties).

The conjugation of hydrophilic polymers, such as PEG is known in the art. In its most common form, PEG is a linear polymer terminated at each end with hydroxyl groups: HO—CH$_2$CH$_2$O—(CH$_2$CH$_2$O)$_n$—CH$_2$CH$_2$—OH where n typically ranges from about 3 to about 4000. In a preferred embodiment, the PEG has a molecular weight distribution that is essentially homodisperse. In another preferred embodiment, the PEG is a linear polymer. In another preferred embodiment the PEG is a branched polymer.

Many end-functionalized or branched derivatives and various sizes are known in the art and commercially available. By way of example, conjugation of the PEG or PEO may be carried out using the compositions and methods described herein and in U.S. Pat. No. 7,803,777 (Defrees et al.) and U.S. Pat. No. 4,179,337 (Davis et al.), each of which are incorporated by reference herein in their entirety.

In some embodiments, smaller therapeutic compounds are paired with smaller scaffold moieties and larger therapeutic compounds are paired with larger scaffold moieties. It is contemplated, however, that smaller therapeutic compounds could be paired with a larger scaffold moiety and vice versa. Smaller therapeutic compounds are defined as having a molecular weight of 1 Da to 10 kDa. Larger therapeutic compounds are defined as having a molecular weight of 10 kDa to 1000 kDa.

The scaffolds of the present invention, for example, could have a molecular weight of 100 Daltons (Da.), 500 Da., 1000 Da., 2000 Da., 5000 Da., 10,000 Da., 15,000 Da., 20,000 Da., 30,000 Da., 40,000 Da. or 60,000 Da. In one embodiment of the invention, "small" scaffold moieties may be between about 100 Da. and 20,000 Da. In another embodiment, "large" scaffold moieties may be greater than about 20,000 Da. to about 200,000 Da. In preferred embodiments, the scaffold moiety is between about 100 Da. and 200,000 Da. In more preferred embodiments, the scaffold moiety is between about 100 Da. and 20,000 Da., 200 Da. and 15,000 Da., 300 Da. and 10,000 Da., 400 Da. and 9,000 Da., 500 Da. and 5,000 Da., 600 Da. and 2,000 Da., 1000 Da. and 200,000 Da., 20,000 Da. and 200,000 Da., 100,000 and 200,000 Da., 5000 Da. and 100,000 Da., 10,000 Da. and 80,000 Da., 20,000 Da. and 60,000 Da., or 20,000 Da. and 40,000 Da.

Another component of the carrier molecule preferably comprises a coupling group that is used to covalently attach the drug to the scaffold or the carrier. The coupling groups of the invention include an amine-reactive group, a thiol-reactive group, a maleimide group, a thiol group, an aldehyde group, an NHS-ester group, a haloacetyl group, an iodoacetyl group, a bromoacetyl groups, a SMCC group, a sulfo SMCC group, a carbodiimide group and bifunctional cross-linkers such as NHS-Maleimido, combinations thereof, or other coupling groups familiar to persons skilled in the art. The coupling groups of the invention can promote thiol linkages, amide linkages, oxime linkages, hydrazone linkages, thiazolidinone linkages or utilizes cycloaddition reactions also called click chemistry to couple the carrier to a therapeutic compound. In another embodiment, the composition preferably includes a combination of one or more therapeutic compounds attached to the coupling group of the scaffold molecule.

NHS groups are known to those skilled in the art as being useful for coupling to native peptides and proteins without having to engineer in a site of attachment. NHS groups allow attachment to most proteins and peptides that contain amino acids with amine groups such as a lysine residue. Utilization of NHS groups allows for flexibility in the site of carrier conjugation as protein structure and reaction time can influence the attachment site and number of carrier molecules conjugated to the therapeutic compound. By way of example, controlling the molar ratio of NHS-carrier to therapeutic compound, one skilled in the art can have some control over the number of carrier molecules attached to the therapeutic compound thus allowing for more than one carrier to be conjugated to a given therapeutic compound, if desired.

Conjugation of the carrier to a therapeutic compound is achieved by mixing a solution of the molecules together in a specific molar ratio using compatible solutions, buffers or solvents. For example, a molar ratio of 1:1, 2:1, 4:1, 5:1, 10:1, 20:1, 25:1, 50:1, 100:1, 1000:1, or 1:2, 1:4, 1:5, 1:10, 1:20 1:25, 1:50, 1:100 or 1:1000 of carrier to therapeutic compound could be used. In certain embodiments, a molar ratio of 1:1, 2:1, 4:1, 5:1, 10:1, 20:1, 25:1 or 1:2, 1:4, 1:5, 1:10, 1:20 1:25, 1:50 of carrier to therapeutic compound could be used. In preferred embodiments, a molar ratio of 1:1, 2:1, 4:1, 5:1, 10:1 or 1:2, 1:4, 1:5, 1:10 of carrier to therapeutic compound could be used. By varying the ratio, this could result in different numbers of individual carriers attached to the therapeutic compound, or could help to select a specific site of attachment. Attachment of the carriers is also pH, buffer, salt and temperature dependent and varying these parameters among other parameters can influence the site of attachment the number of carriers attached and the speed of the reaction. For example, by selecting a pH for the reaction at or below pH 6 could help selectively conjugate an aldehyde version of the carrier to the N-terminus of the therapeutic protein or peptide.

In certain embodiments, the present invention provides carriers that include those of formula I:

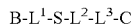
B-L$^1$-S-L$^2$-L$^3$-C    I

Wherein:
B is a targeting group selected from vitamin D, a vitamin D analog, a vitamin D-related metabolite, an analog of a vitamin D related-metabolite, a peptide that binds DBP, an anti-DBP antibody, an anti-DBP antibody derivative, a nucleotide aptamer that binds DBP, or a small carbon-based molecule that binds DBP;
S is a scaffold moiety, comprising poly(ethylene glycol), polylysine, polyethyleneimine, poly(propyleneglycol), a peptide, serum albumin, thioredoxin, an immunoglobulin, an amino acid, a nucleic acid, a glycan, a modifying group that contains a reactive linker, polylactic acid, a water-soluble polymer, a small carbon chain linker, or an additional therapeutic compound;
C is an amine-reactive group, a thiol-reactive group, a maleimide group, a thiol group, a disulfide group, an aldehyde group, an NHS-ester group, a 4-nitrophenyl ester, an acylimidazole, a haloacetyl group, an iodoacetyl group, a bromoacetyl groups, a SMCC group, a sulfo SMCC group, a carbodiimide group and bifunctional cross-linkers such as NHS-Maleimido or combinations thereof;
L$^1$ and L$^2$ are linkers independently selected from —(CH$_2$)$_n$—, —C(O)NH—, —HNC(O)—, —C(O)O—, —OC(O)—, —O—, —S—S—, —S—, —S(O)—, —S(O)$_2$— and —NH—;
L$^3$ is —(CH$_2$)$_o$—;
n is an integer from 0-3; and
o is an integer from 0-3.

In preferred embodiments, the present invention provides carriers that include those of formula I:

B-L$^1$-S-L$^2$-L$^3$-C    I

Wherein:
B is a targeting group selected from vitamin D, a vitamin D analog, a vitamin D-related metabolite, an analog of a vitamin D related-metabolite, or a small carbon-based molecule that binds DBP;
S is a scaffold moiety, comprising poly(ethylene glycol), polylysine, poly(propyleneglycol), a peptide, serum albumin, an amino acid, a nucleic acid, a glycan, polylactic acid, a water-soluble polymer, or a small carbon chain linker;
C is a maleimide group, a thiol group, a disulfide group, an aldehyde group, an NHS-ester group, an iodoacetyl group, or a bromoacetyl group;
L$^1$ and L$^2$ are linkers independently selected from —(CH$_2$)$_n$—, —C(O)NH—, —HNC(O)—, —C(O)O—, —OC(O)—, —O—, —S—, and —NH—;
L$^3$ is —(CH$_2$)$_o$—;
n is an integer from 0-3; and
o is an integer from 0-3.

In more preferred embodiments, the present invention provides carriers that include those of formula I:

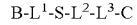
B-L$^1$-S-L$^2$-L$^3$-C    I

Wherein:
B is a targeting group selected from vitamin D, a vitamin D analog, or a vitamin D-related metabolite;
S is a scaffold moiety, comprising poly(ethylene glycol), polylysine or poly(propyleneglycol);
C is a maleimide group, a disulfide group, an aldehyde group, an NHS-ester group or an iodoacetyl group;
L$^1$ and L$^2$ are linkers independently selected from —(CH$_2$)$_n$—, —C(O)NH—, —HNC(O)—, —C(O)O— and —OC(O)—;
L$^3$ is —(CH$_2$)$_o$—;
n is an integer from 0-3; and
o is an integer from 0-3.

In most preferred embodiments, the present invention provides carriers that include those of formulas IIa and IIb:

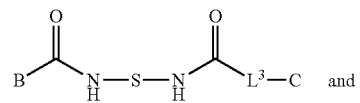

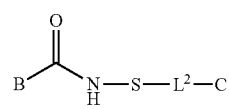

Wherein:
B is a targeting group selected from vitamin D, a vitamin D analog, or a vitamin D-related metabolite;

S is a scaffold moiety, comprising poly(ethylene glycol), or poly(propyleneglycol); and
C is a maleimide group, a disulfide group, an aldehyde group, an NHS-ester group or an iodoacetyl group;
$L^2$ is —$(CH_2)_n$—;
$L^3$ is —$(CH_2)_o$—;
n is 1; and
o is 2.

In certain most preferred embodiments of formula IIa, B is represented by formula III, S is poly(ethylene glycol) and $L^3$-C is represented by formula IVa.

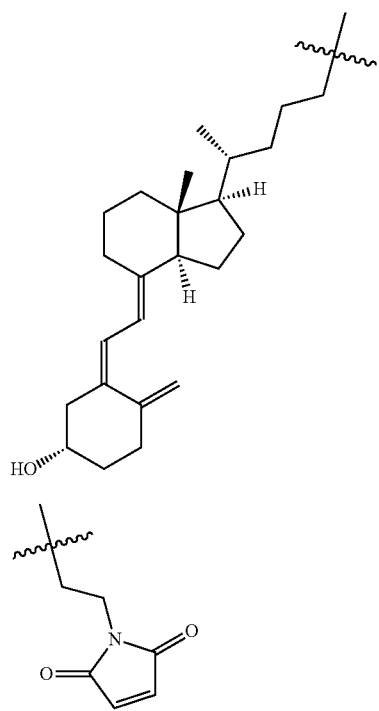

In certain most preferred embodiments of formula IIb, B is represented by formula III, S is poly(ethylene glycol) and $L^2$-C is represented by formula IVb.

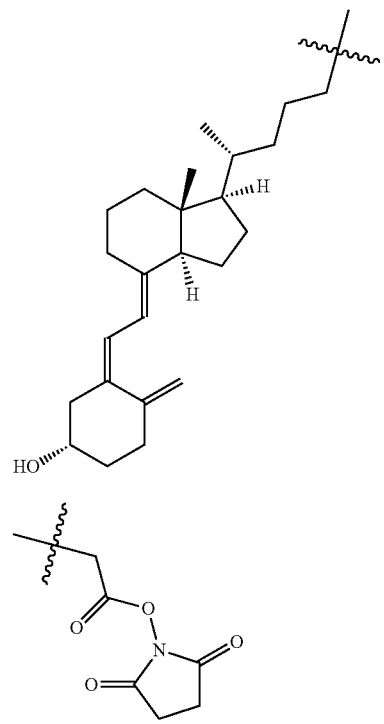

In certain most preferred embodiment, S is between about 100 Da. and 200,000 Da. In other most preferred embodiments, the scaffold moiety is between about 100 Da. and 20,000 Da., 200 Da. and 15,000 Da., 300 Da. and 10,000 Da., 400 Da. and 9,000 Da., 500 Da. and 5,000 Da., 600 Da. and 2,000 Da., 1000 Da. and 200,000 Da., 5000 Da. and 100,000 Da., 10,000 Da. and 80,000 Da., 20,000 Da. and 60,000 Da., or 20,000 Da. and 40,000 Da.

In a specific embodiment, the present invention provides a carrier represented by formula V.

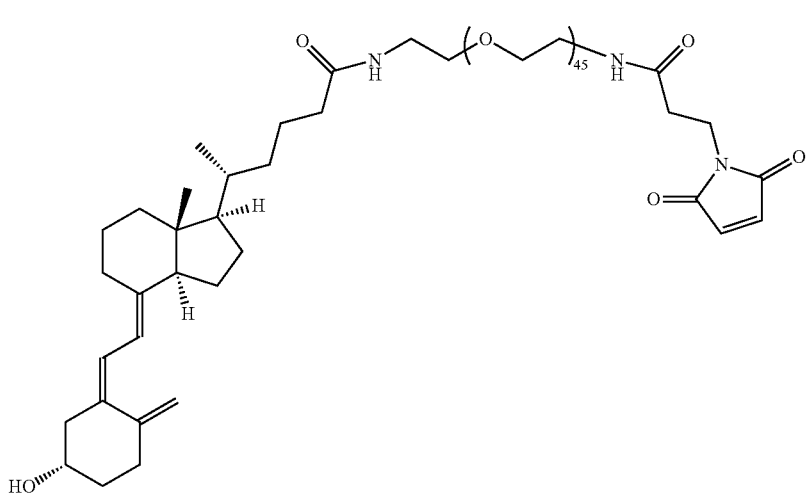

In another specific embodiment, the present invention provides a carrier represented by formula VI.

VI

[Chemical structure of vitamin D derivative conjugated via amide linkage to -(OCH2CH2)45-O-CH2-C(O)-O-N-hydroxysuccinimide ester]

In certain embodiments, the present invention provides a method for producing a carrier of formula I:

B-L¹-S-L²-L³-C   I comprising the step of reacting a compound of formula Ia:

B—COOH   Ia with a compound of formula Ib:

H₂N—S-L²-L³-C   Ib in the presence of an amide coupling agent,
wherein B, S, C and L² are defined as above and L¹ is —C(O)NH—.

One skilled in the art will recognize that a compound of formula Ib can be used either as a free base or as a suitable salt form. Suitable salt forms include, but are not limited to TFA, HCl, HBr, MsOH, TfOH and AcOH.

Any suitable amide coupling agent may be used to form a compound of formula I. Suitable amide coupling agents include, but are not limited to 2-chloromethylpyridinium iodide, BOP, PyBOP, HBTU, HATU, DCC, EDCl, TBTU and T3P. In certain embodiments, the amide coupling agent is used alone. In certain embodiments, the amide coupling agent is used with a co-reagent such as HOBT or DMAP. In certain embodiments, the amide coupling agent is used with a base such as triethylamine or diisopropylethylamine. In certain embodiments, the amide coupling agent is used with both a co-reagent such as HOBT or DMAP and a base such as triethylamine or diisopropylethylamine. One skilled in the art will recognize that co-reagents other than HOBT or DMAP may be used. Furthermore, one skilled in the art will recognize that bases other than triethylamine or diisopropylethylamine may be used.

In certain embodiments, the carboxylic acid component of formula Ia is produced by treating an ester of formula Id with a hydrolyzing agent:

B—COOR   Id wherein, B is defined as above and R is a $C_1$-$C_6$ branched or unbranched alkyl group.

Any suitable hydrolyzing agent can be used to prepare a compound of formula Ia from a compound of formula Id.

In certain other embodiments, the present invention provides a method for producing a carrier of formula Ig:

$$B-\overset{O}{\underset{}{C}}-\overset{H}{\underset{}{N}}-S-L^2-L^3-C$$   Ig comprising the steps of reacting a compound of formula Ia:

B—COOH   Ia with a compound of formula Ic:

H₂N—S-L²-L³-COOR¹   Ic in the presence of an amide coupling agent forming a compound of formula Ie;
Hydrolyzing an ester of formula Ie to a carboxylic acid of formula If; and $$B-\overset{O}{\underset{}{C}}-\overset{H}{\underset{}{N}}-S-L^2-L^3-COOR^1 \longrightarrow$$
Ie $$B-\overset{O}{\underset{}{C}}-\overset{H}{\underset{}{N}}-S-L^2-L^3-COOH$$
If Converting a carboxylic acid of formula If to an active ester of formula I;

$$B-\overset{O}{\underset{}{C}}-\overset{H}{\underset{}{N}}-S-L^2-L^3-COOH \longrightarrow$$
If

B—L¹—S—L²—L³—C
I wherein B, S, C, R¹, L², L³, n and o are defined as above and L¹ is —C(O)NH—.

One skilled in the art will recognize that a compound of formula Ic can be used either as a free base or as a suitable salt form. Suitable salt forms include, but are not limited to TFA, HCl, HBr, MsOH, TfOH and AcOH.

Any suitable amide coupling agent may be used to form a compound of formula Ie. Suitable amide coupling agents include, but are not limited to 2-chloromethylpyridinium iodide, BOP, PyBOP, HBTU, HATU, DCC, EDCl, TBTU and T3P. In certain embodiments, the amide coupling agent is used alone. In certain embodiments, the amide coupling agent is used with a co-reagent such as HOBT or DMAP. In certain embodiments, the amide coupling agent is used with a base such as triethylamine or diisopropylethylamine. In certain embodiments, the amide coupling agent is used with both a co-reagent such as HOBT or DMAP and a base such as triethylamine or diisopropylethylamine. One skilled in the art will recognize that co-reagents other than HOBT or DMAP may be used. Furthermore, one skilled in the art will recognize that bases other than triethylamine or diisopropylethylamine may be used.

In certain embodiments, the carboxylic acid component of formula Ia is produced by treating an ester of formula Id with a hydrolyzing agent:

    Id wherein, B is defined as above and R is a $C_1$-$C_6$ branched or unbranched alkyl group.

Any suitable hydrolyzing agent can be used to prepare a compound of formula Ia from a compound of formula Id. Suitable hydrolyzing agents include, but are not limited to lithium hydroxide, sodium hydroxide and potassium hydroxide.

Any suitable hydrolyzing agent can be used to prepare a compound of formula If from a compound of formula Ie. Suitable hydrolyzing agents include, but are not limited to lithium hydroxide, sodium hydroxide and potassium hydroxide.

Any suitable leaving group can be coupled with a carboxylic acid of formula If in the presence of a suitable coupling reagent to form an active ester of formula I. Suitable leaving groups include, but are not limited to imidazole, HOBT, NHS and 4-nitrophenol. Suitable coupling reagents include, but are not limited to 2-chloromethylpyridinium iodide, BOP, PyBOP, HBTU, HATU, DCC, EDCl, TBTU and T3P.

In some embodiments, an active ester of formula I is formed from a carboxylic acid of formula If using a combination of a suitable leaving group and a coupling reagent.

In some embodiments, an active ester of formula I is formed from a carboxylic acid of formula If using a single reagent that produces a leaving group and also effects a coupling reaction. Such reagents include, but are not limited to 1,1'-carbonyldiimidazole, N,N'-disuccinimidyl carbonate, 4-nitrophenyl trifluoroacetate and HBTU. In some embodiments, the single reagent is used alone. In other embodiments, the single reagent is used with an acyl transfer catalyst. Such acyl transfer catalysts include, but are not limited to DMAP and pyridine. One skilled in the art will recognize that additional acyl transfer catalysts may be used.

In a specific embodiment, the present invention provides a method for producing a carrier represented by formula V:

comprising the step of reacting a compound of formula Va:

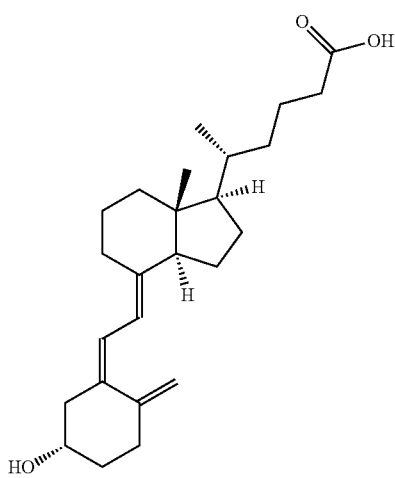

with a compound of formula Vb:

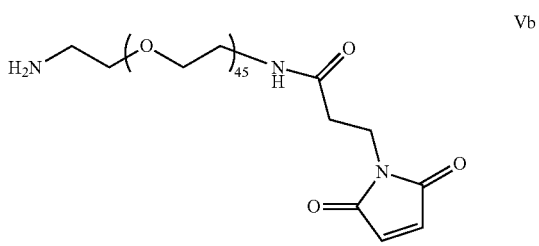

in the presence of an amide coupling agent. One skilled in the art will recognize that a compound of formula Vb can be used either as a free base or as a suitable salt form. Suitable salt forms include, but are not limited to TFA, HCl, HBr, MsOH, TfOH and AcOH.

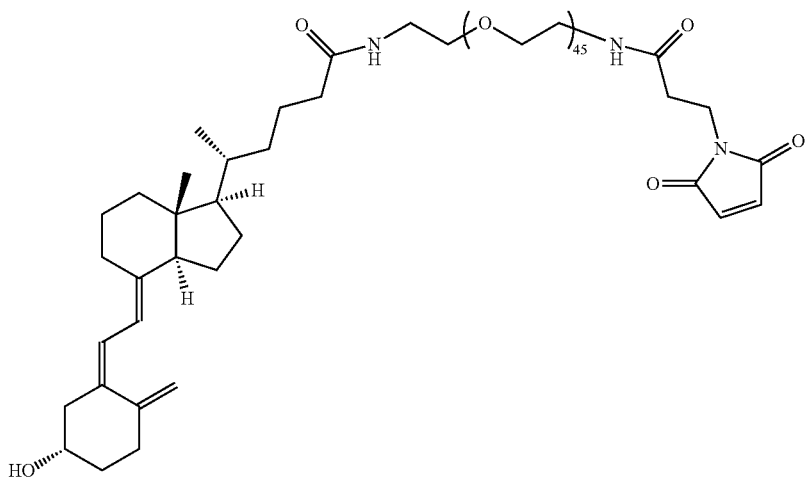

Any suitable amide coupling agent may be used to form a compound of formula V. Suitable amide coupling agents include, but are not limited to 2-chloromethylpyridinium iodide, BOP, PyBOP, HBTU, HATU, DCC, EDCl, TBTU and T3P. In certain embodiments, the amide coupling agent is used alone. In certain embodiments, the amide coupling agent is used with a co-reagent such as HOBT or DMAP. In certain embodiments, the amide coupling agent is used with a base such as triethylamine or diisopropylethylamine. In certain embodiments, the amide coupling agent is used with both a co-reagent such as HOBT or DMAP and a base such as triethylamine or diisopropylethylamine. One skilled in the art will recognize that co-reagents other than HOBT or DMAP may be used. Furthermore, one skilled in the art will recognize that bases other than triethylamine or diisopropylethylamine may be used.

In a specific embodiment, the carboxylic acid component of formula Va is produced by treating a methyl ester of formula Vc with a hydrolyzing agent:

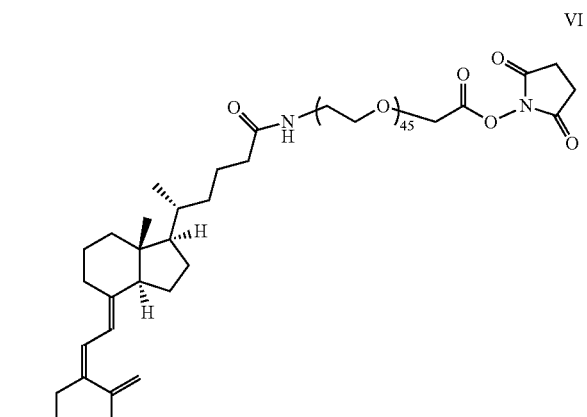

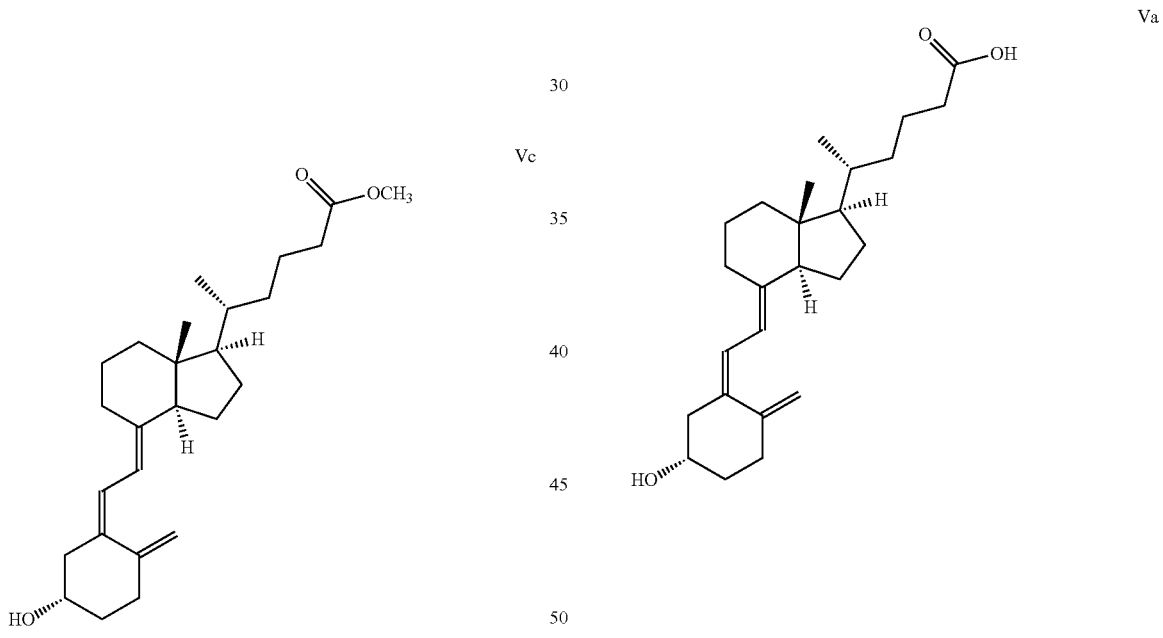

Any suitable hydrolyzing agent can be used to prepare a compound of formula Va from a compound of formula Vc. Suitable hydrolyzing agents include, but are not limited to lithium hydroxide, sodium hydroxide and potassium hydroxide.

In another specific embodiment, the present invention provides a method for producing a carrier represented by formula VI:

comprising the steps of reacting a compound of formula Va:

with a compound of formula VIa:

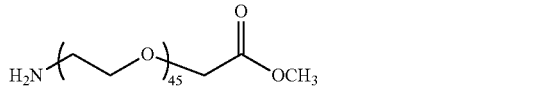

in the presence of an amide coupling agent forming a compound of formula VIb;
Hydrolyzing an ester of formula VIb to a carboxylic acid of formula VIc; and

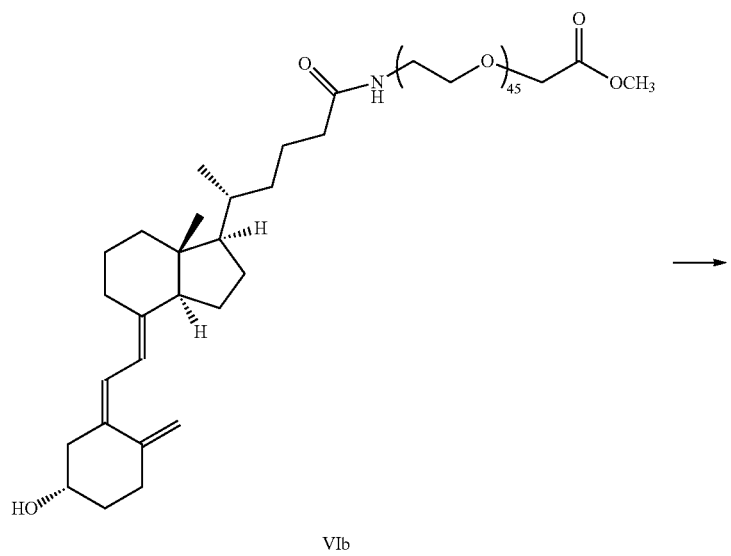
VIb
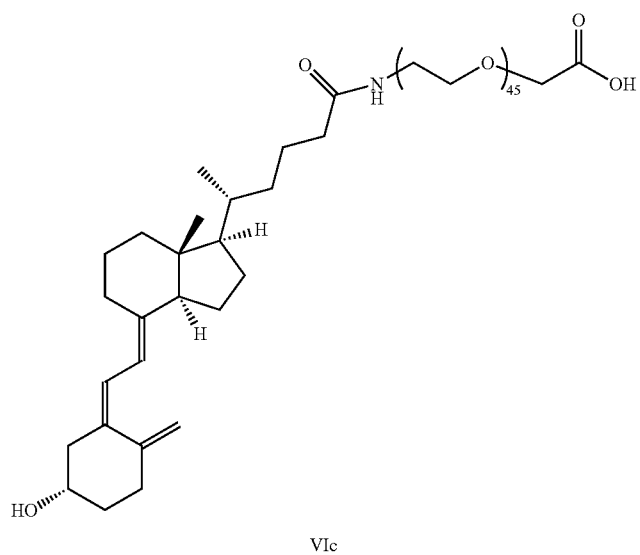
VIc
Converting a carboxylic acid of formula VIc to an active ester of formula VI;

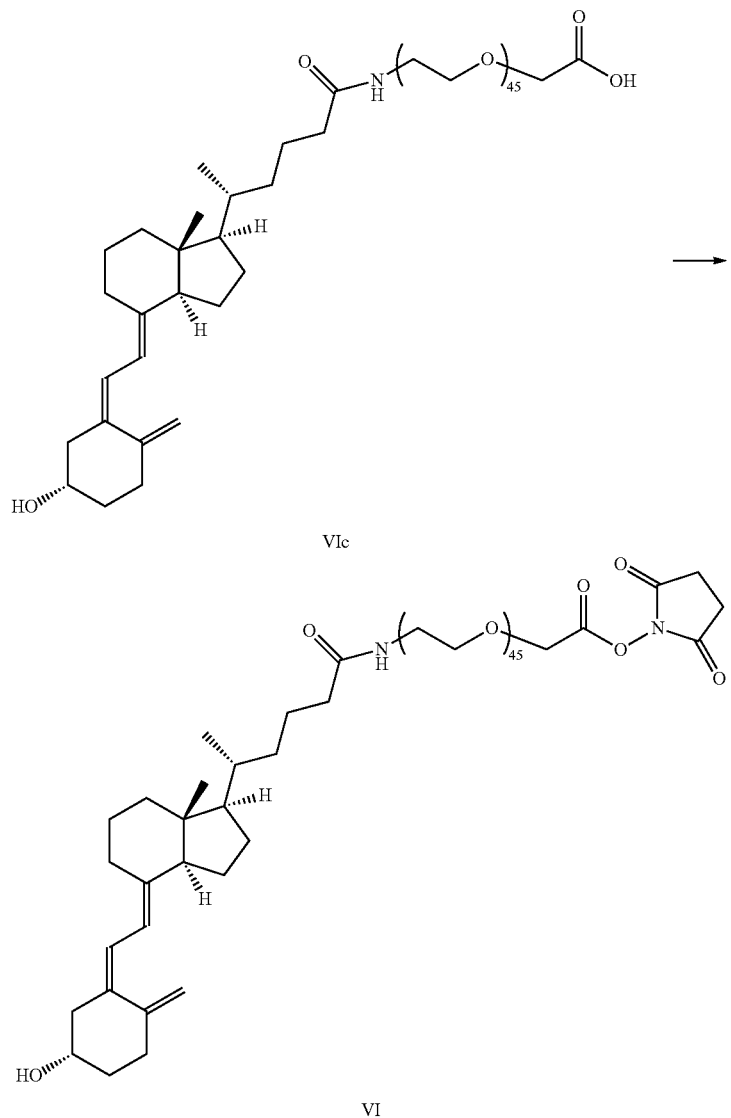

One skilled in the art will recognize that a compound of formula VIa can be used either as a free base or as a suitable salt form. Suitable salt forms include, but are not limited to TFA, HCl, HBr, MsOH, TfOH and AcOH.

Any suitable amide coupling agent may be used to form a compound of formula VIb. Suitable amide coupling agents include, but are not limited to 2-chloromethylpyridinium iodide, BOP, PyBOP, HBTU, HATU, DCC, EDCl, TBTU and T3P. In certain embodiments, the amide coupling agent is used alone. In certain embodiments, the amide coupling agent is used with a co-reagent such as HOBT or DMAP. In certain embodiments, the amide coupling agent is used with a base such as triethylamine or diisopropylethylamine. In certain embodiments, the amide coupling agent is used with both a co-reagent such as HOBT or DMAP and a base such as triethylamine or diisopropylethylamine. One skilled in the art will recognize that co-reagents other than HOBT or DMAP may be used. Furthermore, one skilled in the art will recognize that bases other than triethylamine or diisopropylethylamine may be used.

Any suitable hydrolyzing agent can be used to prepare a compound of formula VIc from a compound of formula VIb. Suitable hydrolyzing agents include, but are not limited to lithium hydroxide, sodium hydroxide and potassium hydroxide.

NHS can be coupled with a carboxylic acid of formula VIc in the presence of a suitable coupling reagent to form an active ester of formula VI. Suitable coupling reagents include, but are not limited to 2-chloromethylpyridinium iodide, BOP, PyBOP, HBTU, HATU, DCC, EDCl, TBTU and T3P.

In some embodiments, an active ester of formula VI is formed from a carboxylic acid of formula VIc using a combination of NHS and a coupling reagent.

In some embodiments, an active ester of formula VI is formed from a carboxylic acid of formula VIc using a single reagent that produces a leaving group and also effects a coupling reaction. Such reagents include, but are not limited to, N,N'-disuccinimidyl carbonate. In some embodiments, the single reagent is used alone. In other embodiments, the single reagent is used with an acyl transfer catalyst. Such acyl transfer catalysts include, but are not limited to DMAP and pyridine. One skilled in the art will recognize that additional acyl transfer catalysts may be used.

In a specific embodiment, the carboxylic acid component of formula Va is produced by treating a methyl ester of formula Vc with a hydrolyzing agent:

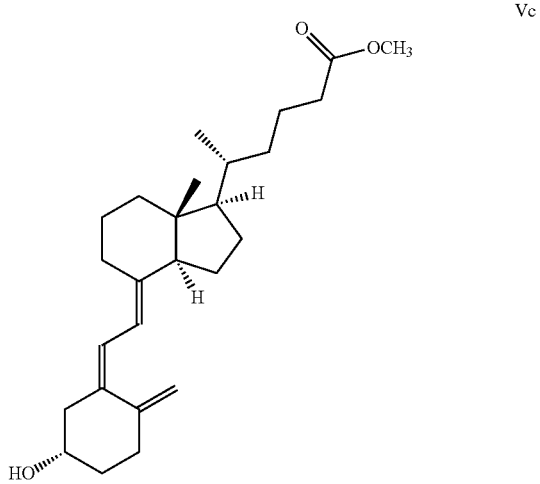 [SMILES: C=C1CC[C@H](O)C/C1=C/C=C1\CCC[C@]2(C)[C@@H]([C@H](C)CCCC(=O)OC)CC[C@@H]12]

Vc

Any suitable hydrolyzing agent can be used to prepare a compound of formula Va from a compound of formula Vc. Suitable hydrolyzing agents include, but are not limited to lithium hydroxide, sodium hydroxide and potassium hydroxide.

If desired, therapeutic compound carrier conjugates having different molecular weights can be isolated using gel filtration chromatography and/or ion exchange chromatography. Gel filtration chromatography may be used to fractionate different therapeutic compound carrier conjugates (e.g., 1-mer, 2-mer, 3-mer, and so forth, wherein "1-mer" indicates one targeting group molecule per therapeutic compound, "2-mer" indicates two targeting groups attached to therapeutic compound, and so on) on the basis of their differing molecular weights (where the difference corresponds essentially to the average molecular weight of the targeting group).

Gel filtration columns suitable for carrying out this type of separation include Superdex and Sephadex columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, and (iii) sodium dodecyl sulfate polyacrylamide gel electrophoresis (SDS PAGE).

Separation of therapeutic compound carrier conjugates can also be carried out by reverse phase chromatography using a reverse phase-high performance liquid chromatography (RP-HPLC) C18 column (Amersham Biosciences or Vydac) or by ion exchange chromatography using an ion exchange column, e.g., a DEAE- or CM-Sepharose ion exchange column available from Amersham Biosciences. The resulting purified compositions are preferably substantially free of the non-targeting group-conjugated therapeutic compound. In addition, the compositions preferably are substantially free of all other non-covalently attached targeting groups The invention provides compositions and methods for rendering a drug more potent by improving its pharmacokinetic properties using vitamin D or another DBP binding molecule. The natural pathway for the formation of vitamin D at the skin upon exposure to ultraviolet light relies on the interaction with DBP to bring the UV activated vitamin D into circulation where it can be utilized for cellular processes (Lips, *Prog. Biophys. Molec. Biol.* 92:4-8 (2006); DeLuca, *Nutr. Rev.* 66 (suppl. 2):573-578 (2008)). DBP brings vitamin D into circulation quickly and effectively. DBP also keeps active vitamin D in circulation for, on average, 30 days (Cooke, N. E., and J. G. Haddad. 1989. Endocr. Rev. 10:294-307; Haddad, J. G. et al. 1993. J. Clin. Invest. 91:2552-2555; Haddad, J. G. 1995. J. Steroid Biochem. Molec. Biol. 53:579-582). The invention provides for the first time using DBP to more effectively deliver therapeutic compounds to the body. In one embodiment, the therapeutic compound is covalently linked or fused to a carrier. In another embodiment, the therapeutic compound is formulated with the carrier but not covalently linked. In one embodiment, the carrier interacts with DBP for the purpose of carrying the drug into the body more effectively from the site of administration. In another embodiment, the carrier keeps the drug in circulation for an extended period of time.

In one embodiment, the carrier comprises a targeting group and a coupling group for attaching the targeting group to the therapeutic compound. In another embodiment, the carrier comprises a scaffold moiety that is linked to the targeting group and the therapeutic compound. The targeting group is vitamin D, a vitamin D analog, a vitamin D-related metabolite, a vitamin D-related metabolite analog, or another molecule that can bind to or interact with the vitamin D binding protein (DBP). In one embodiment, the targeting group is an antibody or antibody derivative, a peptide designed to bind DBP or a fragment thereof, a peptide derived from a phage display or other peptide library selected against DBP or a fragment thereof, a nucleotide aptamer that binds DBP, a small molecule designed to bind DBP or derived from a chemical library selected against DBP, or a fragment thereof or moiety that can bind DBP as disclosed herein. In another embodiment, the carrier comprises DBP itself or a derivative of DBP.

Vitamin D is a group of fat-soluble secosteroids. Several forms (vitamers) of vitamin D exist. The two major forms are vitamin $D_2$ or ergocalciferol, and vitamin $D_3$ or cholecalciferol, vitamin D without a subscript refers to either $D_2$ or $D_3$ or both. In humans, vitamin D can be ingested as cholecalciferol (vitamin $D_3$) or ergocalciferol (vitamin $D_2$). Additionally, humans can synthesize it from cholesterol when sun exposure is adequate.

Vitamin D is further modified by enzymes found in various organs to a family of "vitamin D metabolites" that are also capable of binding DBP. For instance, vitamin D is converted to calcidiol (25OH hydroxy-Vitamin D) in the liver. Part of the calcidiol is converted by the kidneys to calcitriol (1,25 (OH)$_2$ dihydroxy-Vitamin D). Calcidiol is also converted to calcitriol outside of the kidneys for other purposes. Also found in the body is 24,25(OH)$_2$ dihydroxy-Vitamin D. Thus, in one embodiment, the targeting group is a vitamin D metabolite.

In another embodiment, the targeting group is a "Vitamin D analog." These compounds are based on the vitamin D structure and retain partial function of vitamin D. They interact with some of the same proteins as Vitamin D (e.g. DBP and the Vitamin D receptor), albeit at varying affinities. Exemplary analogs include: OCT, a chemically synthesized analogue of 1,25(OH)$_2$D3 with an oxygen atom at the 22 position in the side chain (Abe et. al., *FEBS Lett.* 226:58-62 (1987)); Gemini vitamin D analog, 1α,25-dihydroxy-20R-21 (3-hydroxy-3-deuteromethyl-4,4,4-trideuterobutyl)-23-yne-26,27-hexafluoro-cholecalciferol (BXL0124) (So et al., *Mol*

Pharmacol. 79(3):360-7 (2011)); Paricalcitol, a vitamin $D_2$ derived sterol lacking the carbon-19 methylene group found in all natural vitamin D metabolites (Slatopolsky et al., *Am J. Kidney Dis.* 26: 852 (1995)); Doxercalciferol (1α-hydroxyvitamin $D_2$), like alfacalcidol (1α-hydroxyvitamin $D_3$), is a prodrug which is hydroxylated in the liver to $1α,25(OH)_2D2$. Unlike alfacalcidol, doxercalciferol is also 24-hydroxylated to produce $1α,24(S)—(OH)_2D2$ (Knutson et al., *Biochem Pharmacol* 53: 829 (1997)); Dihydrotachysterol$_2$ ($DHT_2$), hydroxylated in vivo to $25(OH)DHT_2$ and $1,25(OH)_2DHT_2$ (McIntyre et al., *Kidney Int.* 55: 500 (1999)). See also Erben and Musculoskel, *Neuron Interact.* 2(1):59-69 (2001) and Steddon et al. *Nephrol. Dial. Transplant.* 16 (10): 1965-1967 (2001). The foregoing references are incorporated by reference in their entirety.

In another embodiment, the carrier further comprises a pharmaceutically acceptable scaffold moiety covalently attached to the targeting group and the therapeutic compound. The scaffold moiety of the carriers of the invention does not necessarily participate in but may contribute to the function or improve the pharmacokinetic properties of the therapeutic compound. The scaffolds of the invention do not substantially interfere with the binding of the targeting group to DBP. Likewise, the scaffolds of the invention do not substantially interfere with structure or function of the therapeutic compound. The length of the scaffold moiety is dependent upon the character of the targeting group and the therapeutic compound. One skilled in the art will recognize that various combinations of atoms provide for variable length molecules based upon known distances between various bonds (Morrison, and Boyd, *Organic Chemistry,* 3rd Ed, Allyn and Bacon, Inc., Boston, Mass. (1977), incorporated herein by reference). Other scaffolds contemplated by the invention include peptide linkers, protein linkers such as human serum albumin, an antibody or fragment thereof, nucleic acid linkers, small carbon chain linkers, carbon linkers with oxygen or nitrogen interspersed, also combinations of these examples are contemplated.

In another embodiment, a peptide has been selected as the targeting group that binds DBP. Methods of screening peptide or protein libraries for DBP binding peptides are known in the art. In a preferred embodiment, a two-hybrid method of identifying DBP binding peptides is used. In another preferred embodiment, an in vitro screen for DBP binding is used. This targeting peptide can then be covalently attached to or alternatively formulated with a drug. In a preferred embodiment, a scaffold moiety is used. In another embodiment, the targeting group is an aptamer that was selected because it binds DBP. Said aptamer may then be covalently attached to or formulated with a drug either through a scaffold or fused directly to the drug.

In one embodiment, the drug is a a DNA molecule, an RNA molecule, an aptamer (single-stranded or double-stranded), DNA or RNA oligonucleotides, larger DNA molecules that are linear or circular, oligonucleotides that are used for RNA interference (RNAi), variations of DNA such as substitution of DNA/RNA hybrid molecules, synthetic DNA-like molecules such as PNA or other nucleic acid derivative molecules (see WO07/035922, incorporated by reference herein in its entirety). In another embodiment, the therapeutic compound is composed of nuclease-resistant DNA or RNA oligonucleotides. In a preferred embodiment, nuclease-resistant DNA oligonucleotides are Morpholinos, (i.e. phosphorodiamidate analogs of nucleic acids that bind to nucleic acids in a sequence-specific manner, AVI BioPharma, Bothell, Wash.).

In another embodiment, the drug is a small molecule or chemical entity. In another embodiment, the drug is a peptide or a derivative of a peptide such as a PNA. In another embodiment, the drug is a protein comprised of all or part of a polypeptide, whether full-length or a fragment or truncated version, whether PEGylated, glycosylated or otherwise covalently or noncovalently modified or left unmodified.

Therapeutic compounds include proteins, peptides, glycoproteins, glycopeptides, glycolipids, polysaccharides, oligosaccharides, nucleic acids, and the like. Exemplary polypeptides include growth factors, such as hepatocyte growth factors (HGF), nerve growth factors (NGF), epidermal growth factors (EGF), fibroblast growth factors including FGF21, blood coagulation factors, hormones such as growth hormones, follicle stimulating hormone (FSH), cytokines, interferons, tumor necrosis factors, enzymes, bone morphogenetic proteins, neurotrophins, and growth differentiation factors. Compositions and methods of the invention also include conjugated agonists, antagonists, or other effectors of the above-mentioned proteins, glycoproteins, small molecules, hormones, growth factors, and other molecules found within a patient or subject.

Also within the scope of the invention are therapeutic peptides. The term peptide is meant to include a string of amino acids. The amino acids in the peptides of the invention may be naturally-occurring or non-naturally-occurring. The peptides of the invention may be synthesized chemically or biologically, and can include cysteine-rich peptides, circular peptides, stapled peptides, peptides that include D- or L-amino acids and mixtures thereof, peptidomimetics, peptide-nucleic acids (PNAs), and combinations thereof. Exemplary embodiments include AIDS vaccines, allergy vaccines, anti-inflammatory peptides, anti-integrin peptides, anti-TCR vaccines, anti-allergy peptides, anti-cancer peptides, anti-fungal peptides, anti-bacterial peptides, anti-rheumatic peptides, anti-thrombin peptides, anti-viral peptides, G Protein-Coupled Receptor (GPCR) ligands and related peptides (e.g. the Secretin family), CGRP analogues, GPCR antagonists, CMV peptides, calpain inhibitors, collagenase inhibitors, DAP inhibitors, defensins, dialytic oligopeptides, Enhancins, endorphins, endothelin antagonists, fibronectin inhibitors, gastrin antagonists, ghrelin, glucagon antagonists, gonadorelin analogs, growth factor peptides, hypothalamic hormones, pituitary hormones, peptides that control gut function and appetite, proinflammatory adipose tissue products, peptides that stimulate stem cell proliferation, proinflammatory peptides, natural products, herpes simplex vaccines, heparin binding peptides, hepatitis-B vaccines, immunomodulating peptides, influenza vaccines, LHRH antagonists, opiod peptide derivatives, MMP inhibitors, MUC-1 vaccines, malaria vaccines, melanoma vaccines, meningitis vaccines, neuropeptides, opioid peptides, osteogenic growth peptides, osteoporosis peptides, papillomavirus vaccines, prostate cancer vaccines, RGD peptides, RSV vaccines, T cell receptor peptides and the like. The invention contemplates synthetic analogs thereof which would be improved as clinical products through further modification by the methods described herein. Those skilled in the art will recognize many additional commercially important peptides that are amenable to modifications described herein to provide increased half-life, duration of action, absorption and/or bioavailability.

Also contemplated within the scope of embodiments described herein are peptides that are branched or cyclic, with or without branching. Cyclic, branched and branched circular peptides result from post-translational natural processes and are also made by suitable synthetic methods. In some embodiments, any peptide product described herein comprises a peptide analog described above that is then covalently attached to an alkyl-glycoside surfactant moiety.

Also contemplated within the scope of embodiments presented herein are peptide chains that are substituted in a suitable position by the modification of the analogs claimed herein. For example, acylation is on a linker amino acid, for example, at the ε-position of Lysine, with fatty acids such as octanoic, decanoic, dodecanoic, tetradecanoic, hexadecanoic, octadecanoic, 3-phenylpropanoic acids and the like, or with saturated or unsaturated alkyl chains (Zhang, L. and Bulaj, G. (2012) Curr Med Chem 19: 1602-1618, incorporated herein by reference in its entirety).

Also contemplated within the scope of embodiments presented herein are peptide chains that are comprised of natural and unnatural amino acids or analogs of natural amino acids. As used herein, peptide and/or protein "analogs" comprise non-natural amino acids based on natural amino acids, such as tyrosine analogs, which includes para-substituted tyrosines, ortho-substituted tyrosines, and meta-substituted tyrosines, wherein the substituent on the tyrosine comprises an acetyl group, a benzoyl group, an amino group, a hydrazine, an hydroxyamine, a thiol group, a carboxy group, a methyl group, an isopropyl group, a C2-C20 straight chain or branched hydrocarbon, a saturated or unsaturated hydrocarbon, an O-methyl group, a polyether group, a halogen, a nitro group, or the like. Examples of Tyr analogs include 2,4-dimethyl-tyrosine (Dmt), 2,4-diethyl-tyrosine, O-4-allyl-tyrosine, 4-propyl-tyrosine, Ca-methyl-tyrosine and the like. Examples of lysine analogs include ornithine (Orn), homolysine, Ca-methyl-lysine (CMeLys), and the like. Examples of phenylalanine analogs include, but are not limited to, meta-substituted phenylalanines, wherein the substituent comprises a methoxy group, a C1-C20 alkyl group, for example a methyl group, an allyl group, an acetyl group, or the like. Specific examples include, but are not limited to, 2,4,6-trimethyl-L-phenylalanine (Tmp), O-methyl-tyrosine, 3-(2-naphthyl)alanine (Nal(2)), 3-(1-naphthyl)alanine (Nal(1)), 3-methyl-phenylalanine, 1,2,3,4-tetrahydroisoquinoline-3-carboxylic acid (Tic), fluorinated phenylalanines, isopropyl-phenylalanine, p-azido-phenylalanine, p-acyl-phenylalanine, p-benzoyl-phenylalanine, p-iodo-phenylalanine, p-bromophenylalanine, p-amino-phenylalanine, and isopropyl-phenylalanine, and the like.

Also contemplated within the scope of embodiments presented herein are peptide chains containing nonstandard or unnatural amino acids known to the art, for example, C-alpha-disubstituted amino acids such as Aib, Ca-diethylglycine (Deg), aminocyclopentane-1-carboxylic acid (Ac4c), aminocyclopentane-1-carboxylic acid (Ac5c), and the like. Such amino acids frequently lead to a restrained structure, often biased toward an alpha helical structure (Kaul, R. and Balaram, P. (1999) Bioorg Med Chem 7: 105-117, incorporated herein by reference in its entirety). Additional examples of such unnatural amino acids useful in analog design are homoarginine (Har), and the like. Substitution of reduced amide bonds in certain instances leads to improved protection from enzymatic destruction or alters receptor binding. By way of example, incorporation of a Tic-Phe dipeptide unit with a reduced amide bond between the residues (designated as Tic-F[CH2-NH]^-Phe) reduces enzymatic degradation.

Also contemplated within the scope of embodiments presented herein are modifications at the amino or carboxyl terminus may optionally be introduced into the present peptides or proteins (Nestor, J. J., Jr. (2009) Current Medicinal Chemistry 16: 4399-4418). For example, the present peptides or proteins can be truncated or acylated on the N-terminus (Gourlet, P., et al. (1998) Eur J Pharmacol 354: 105-1 1 1, Gozes, I. and Furman, S. (2003) Curr Pharm Des 9: 483-494), the contents of which is incorporated herein by reference).

Other modifications to the N-terminus of peptides or proteins, such as deletions or incorporation of D-amino acids such as D-Phe also can give potent and long acting agonists or antagonists when substituted with the modifications described herein such as long chain alkyl glycosides. Such agonists and antagonists also have commercial utility and are within the scope of contemplated embodiments described herein. The foregoing references are incorporated herein in their entirety.

Also contemplated within the scope of embodiments described herein are carriers covalently attached, fused to or formulated with therapeutic compound analogs, wherein the native therapeutic compound is modified by acetylation, acylation, PEGylation, ADP-ribosylation, amidation, covalent attachment of a lipid or lipid derivative, covalent attachment of phosphotidylinositol, cross-linking, cyclization, disulfide bond formation, demethylation, formation of covalent cross-link formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, (Nestor, J. J., Jr. (2007) Comprehensive Medicinal Chemistry II 2: 573-601, Nestor, J. J., Jr. (2009) Current Medicinal Chemistry 16: 4399-4418, Creighton, T. E. (1993, Wold, F. (1983) Posttranslational Covalent Modification of Proteins 1-12, Seifter, S. and Englard, S. (1990) Methods Enzymol 182: 626-646, Rattan, S. I., et al. (1992) Ann N Y Acad Sci 663: 48-62). The foregoing reference are incorporated by reference in their entirety.

Glycosylated therapeutic peptides may be prepared using conventional Fmoc chemistry and solid phase peptide synthesis techniques, e.g., on resin, where the desired protected glycoamino acids are prepared prior to peptide synthesis and then introduced into the peptide chain at the desired position during peptide synthesis. Thus, the therapeutic peptide polymer conjugates may be conjugated in vitro. The glycosylation may occur before deprotection. Preparation of amino acid glycosides is described in U.S. Pat. No. 5,767,254, WO 2005/097158, and Doores, K., et al., Chem. Commun., 1401-1403, 2006, which are incorporated herein by reference in their entirety. For example, alpha and beta selective glycosylations of serine and threonine residues are carried out using the Koenigs-Knorr reaction and Lemieux's in situ anomerization methodology with Schiff base intermediates. Deprotection of the Schiff base glycoside is then carried out using mildly acidic conditions or hydrogenolysis. A composition, comprising a glycosylated therapeutic peptide conjugate is made by stepwise solid phase peptide synthesis involving contacting a growing peptide chain with protected amino acids in a stepwise manner, wherein at least one of the protected amino acids is glycosylated, followed by water-soluble polymer conjugation. Such compositions may have a purity of at least 95%, at least 97%, or at least 98%, of a single species of the glycosylated and conjugated therapeutic peptide.

Monosaccharides that may by used for introduction at one or more amino acid residues of the therapeutic peptides defined and/or disclosed herein include glucose (dextrose), fructose, galactose, and ribose. Additional monosaccharides suitable for use include glyceraldehydes, dihydroxyacetone, erythrose, threose, erythrulose, arabinose, lyxose, xylose, ribulose, xylulose, allose, altrose, mannose, N-Acetyl-neuraminic acid, fucose, N-Acetylgalactosamine, and N-Acetylglucosamine, as well as others. Glycosides, such as mono-, di-, and trisaccharides for use in modifying a therapeutic peptide, one or more amino acid residues of the therapeutic peptides defined and/or disclosed herein include sucrose, lactose, maltose, trehalose, melibiose, and cellobiose, among others. Trisaccharides include acarbose, raffinose, and melezitose.

In further embodiments of the invention, the therapeutic compounds defined and/or disclosed herein may be chemically coupled to biotin. The biotin/therapeutic compound can then bind to avidin.

Also within the scope of the invention are polypeptides that are antibodies. The term antibody is meant to include monoclonal antibodies, polyclonal antibodies, toxin-conjugated antibodies, humanized antibodies, antibody fragments (e.g., Fc domains), Fab fragments, single chain antibodies, bi- or multi-specific antibodies, Llama antibodies, nano-bodies, diabodies, Fv, Fab, F(ab')2, Fab', scFv, scFv-Fc, and the like. Also included in the term are antibody-fusion proteins, such as Ig chimeras. Preferred antibodies include humanized or fully human monoclonal antibodies or fragments thereof The terms "antibody" and "immunoglobulin" are used interchangeably in the broadest sense and include monoclonal antibodies (e.g., full length or intact monoclonal antibodies), polyclonal antibodies, monovalent antibodies, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

The terms "full length antibody," "intact antibody" and "whole antibody" are used herein interchangeably to refer to an antibody in its substantially intact form, not antibody fragments as defined below. The terms particularly refer to an antibody with heavy chains that contain the Fc region. "Antibody fragments" comprise a portion of an intact antibody, preferably comprising the antigen binding region thereof. Examples of antibody fragments include Fab, Fab', F(ab')2, and Fv fragments; diabodies; linear antibodies; single-chain antibody molecules; and multispecific antibodies formed from antibody fragments. The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies.

In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

Antibodies that bind specifically to an antigen have a high affinity for that antigen. Antibody affinities may be measured by a dissociation constant (Kd). In certain embodiments, an antibody provided herein has a dissociation constant (Kd) of $\leq 100$ nM, $\leq 10$ nM, $\leq 1$ nM, 0.1 nM, $\leq 0.01$ nM, or $\leq 0.001$ nM (e.g. 10-8M or less, e.g. from 10-8 M to 10-13M, e.g., from 10-9M to 10-13 M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of (125I)-labeled antigen in the presence of a titration series of unlabeled antigen, then capturing bound antigen with an anti-Fab antibody-coated plate (see, e.g., Chen et al., J. Mol. Biol. 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [125I]-antigen are mixed with serial dilutions of a Fab of interest (e.g., consistent with assessment of the anti-VEGF antibody, Fab-12, in Presta et al., Cancer Res. 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with, e.g., immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates (kon) and dissociation rates (koff) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio koff/kon See, e.g., Chen et al., J. Mol. Biol. 293:865-881 (1999). If the on-rate exceeds 106 M-1 s-1 by the surface plasmon resonance assay above, then the on-rate can be determined by using a fluorescent quenching technique that measures the increase or decrease in fluorescence emission intensity (excitation=295 nm; emission=340 nm, 16 nm bandpass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette. Other coupling chemistries for the target antigen to the chip surface (e.g., streptavidin/biotin, hydrophobic interaction, or disulfide chemistry) are also readily available instead of the amine coupling methodology (CM5 chip) described above, as will be understood by one of ordinary skill in the art.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al, *Nature,* 256: 495 (1975); Harlow et al, *Antibodies: A Laboratory Manual,* (Cold Spring Harbor Laboratory Press, 2nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), phage display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101 (34): 12467-12472 (2004); and Lee et al., *J. Immunol. Methods* 284(1-2): 119-132(2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996) and Lonberg and Huszar, *Intern. Rev. Immunol.* 13: 65-93 (1995). The above patents, publications, and references are incorporated by reference in their entirety.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit, or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, Ann. Allergy, *Asthma & Immunol.* 1:105-115 (1998); Harris, *Biochem. Soc. Transactions* 23: 1035-1038 (1995); Hurle and Gross, *Curr. Op. Biotech.* 5:428-433 (1994). The foregoing references are incorporated by reference in their entirety.

A "human antibody" is one which comprises an amino acid sequence corresponding to that of an antibody produced by a human and/or has been made using any of the techniques for making human antibodies as disclosed herein. Such techniques include screening human-derived combinatorial libraries, such as phage display libraries (see, e.g., Marks et al., *J. Mol. Biol,* 222: 581-597 (1991) and Hoogenboom et al., *Nucl. Acids Res.,* 19: 4133-4137 (1991)); using human myeloma and mouse-human heteromyeloma cell lines for the production of human monoclonal antibodies (see, e.g., Kozbor, *J. Immunol,* 133: 3001 (1984); Brodeur et al., *Monoclonal Antibody Production Techniques and Applications,* pp. 55-93 (Marcel Dekker, Inc., New York, 1987); and Boerner et al., *J. Immunol,* 147: 86 (1991)); and generating monoclonal antibodies in transgenic animals (e.g., mice) that are capable of producing a full repertoire of human antibodies in the absence of endogenous immunoglobulin production (see, e.g., Jakobovits et al., *Proc. Natl. Acad. Sci USA,* 90: 2551 (1993); Jakobovits et al., *Nature,* 362: 255 (1993); Bruggermann et al., *Year in Immunol.,* 7: 33 (1993)). This definition of a human antibody specifically excludes a humanized antibody comprising antigen-binding residues from a non-human animal.

All known types of such antibodies are within the scope of the invention. Exemplary antibodies include those that bind to growth factors, cytokines, lymphokines, cell surface receptors, enzymes, vascular endothelial growth factors, fibroblast growth factors, and antibodies to their respective receptors. Other exemplary antibodies include monoclonal antibodies directed to receptor-IgG Fc fusion proteins, and glycoproteins. Any modified (e.g., mutated) version of any of the above listed polypeptides is also within the scope of the invention. Therapeutic compounds to be used in the invention are known in the art and are disclosed by way of example in U.S. Pat. No. 7,608,681, incorporated herein by reference in its entirety. Additionally, the invention contemplates conjugates of inhibitors or antagonists of naturally-occurring or non-naturally occurring antibodies in a subject that cause autoimmune diseases or undesirable inflammatory conditions.

Some aspects of the assembly of carriers utilizes chemical methods that are well-known in the art. For example, Vitamin E-PEG is manufactured by Eastman Chemical, Biotin-PEG is manufactured by many PEG manufacturers such as Enzon, Nektar and NOF Corporation. Methods of producing PEG molecules with some vitamins and other therapeutic compounds linked to them follows these and other chemical methods known in the art. The attachment of PEG to an oligonucleotide or related molecule occurs, for example, as the PEG2-N-hydroxysuccinimide ester coupled to the oligonucleotide through the 5' amine moiety. Several coupling methods are contemplated and include, for example, NHS coupling to amine groups such as a lysine residue on a peptide, maleimide coupling to sulfhydryl group such as on a cysteine residue, iodoacetyl coupling to a sulfhydryl group, pyridyldithiol coupling to a sulfhydryl group, hydrazide for coupling to a carbohydrate group, aldehyde for coupling to the N-terminus, or tetrafluorophenyl ester coupling that is known to react with primary or secondary amines. Other possible chemical coupling methods are known to those skilled in the art and can be substituted. By way of example, conjugation using the coupling groups of the invention may be carried out using the compositions and methods described in WO93/012145 (Atassi et al.) and also see U.S. Pat. No. 7,803,777 (Defrees et al.), incorporated by reference herein in their entirety.

In one embodiment, carrier compounds may be covalently or noncovalently attached to the drug. In another embodiment, the carrier compounds are separate from the drugs but are mixed together at discrete concentrations so as to become formulated into functional units. Exemplary drug formulations of the invention include aqueous solutions, organic solutions, powder formulations, solid formulations and a mixed phase formulations.

Pharmaceutical compositions of this invention comprise any of the compounds of the present invention, and pharmaceutically acceptable salts thereof, with any pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts retain the desired biological activity of the therapeutic composition without toxic side effects. Examples of such salts are (a) acid addition salts formed with inorganic acids, for example, hydrochloric acid, hydrobromic acid, sulfuric acid, phosphoric acid, nitric acid and the like/and salts formed with organic acids such as, for example, acetic acid, trifluoroacetic acid, tartaric acid, succinic acid, maleic acid, fumaric acid, gluconic acid, citric acid, malic acid, ascorbic acid, benzoic acid, tanic acid, pamoic acid, alginic acid, polyglutamic acid, naphthalenesulfonic acid, naphthalene disulfonic acid, polygalacturonic acid and the like; (b) base addition salts or complexes formed with polyvalent metal cations such as zinc, calcium, bismuth, barium, magnesium, aluminum, copper, cobalt, nickel, cadmium, and the like; or with an organic cation formed from N,N'-dibenzylethylenediamine or ethlenediamine; or (c) combinations of (a) and (b), e.g. a zinc tannate salt and the like.

The pharmaceutical compositions of this invention may be administered by transdermal, oral, parenteral, inhalation, ocular, topical, rectal, nasal, buccal (including sublingual), vaginal, or implanted reservoir modes. The pharmaceutical compositions of this invention may contain any conventional, non-toxic, pharmaceutically-acceptable carriers, adjuvants or vehicles. The term parenteral as used herein includes subcutaneous, intracutaneous, intravenous, intramuscular, intraarticular, intrasynovial, intrasternal, intrathecal, intralesional, and intracranial injection or infusion techniques.

Also contemplated, in some embodiments, are pharmaceutical compositions comprising as an active ingredient, therapeutic compounds described herein, or pharmaceutically acceptable salt thereof, in a mixture with a pharmaceutically acceptable, non-toxic component. As mentioned above, such compositions may be prepared for parenteral administration, particularly in the form of liquid solutions or suspensions; for oral or buccal administration, particularly in the form of tablets or capsules; for intranasal administration, particularly in the form of powders, nasal drops, evaporating solutions or aerosols; for inhalation, particularly in the form of liquid solutions or dry powders with excipients, defined broadly; for transdermal administration, particularly in the form of a skin patch or microneedle patch; and for rectal or vaginal administration, particularly in the form of a suppository.

The compositions may conveniently be administered in unit dosage form and may be prepared by any of the methods well-known in the pharmaceutical art, for example, as described in Remington's Pharmaceutical Sciences, $17^{th}$ ed., Mack Publishing Co., Easton, Pa. (1985), incorporated herein by reference in its entirety. Formulations for parenteral administration may contain as excipients sterile water or saline alkylene glycols such as propylene glycol, polyalkylene glycols such as polyethylene glycol, saccharides, oils of vegetable origin, hydrogenated napthalenes, serum albumin or other nanoparticles (as used in Abraxane™, American Pharmaceutical Partners, Inc. Schaumburg, Ill.), and the like. For oral administration, the formulation can be enhanced by the addition of bile salts or acylcarnitines. Formulations for nasal administration may be solid or solutions in evaporating solvents such as hydrofluorocarbons, and may contain excipients for stabilization, for example, saccharides, surfactants, submicron anhydrous alpha-lactose or dextran, or may be aqueous or oily solutions for use in the form of nasal drops or metered spray. For buccal administration, typical excipients include sugars, calcium stearate, magnesium stearate, pregelatinated starch, and the like.

Delivery of modified therapeutic compounds described herein to a subject over prolonged periods of time, for example, for periods of one week to one year, may be accomplished by a single administration of a controlled release system containing sufficient active ingredient for the desired release period. Various controlled release systems, such as monolithic or reservoir-type microcapsules, depot implants, polymeric hydrogels, osmotic pumps, vesicles, micelles, liposomes, transdermal patches, iontophoretic devices and alternative injectable dosage forms may be utilized for this purpose. Localization at the site to which delivery of the active ingredient is desired is an additional feature of some controlled release devices, which may prove beneficial in the treatment of certain disorders.

In certain embodiments for transdermal administration, delivery across the barrier of the skin would be enhanced using electrodes (e.g. iontophoresis), electroporation, or the application of short, high-voltage electrical pulses to the skin, radiofrequencies, ultrasound (e.g. sonophoresis), microprojections (e.g. microneedles), jet injectors, thermal ablation, magnetophoresis, lasers, velocity, or photomechanical waves. The drug can be included in single-layer drug-in-adhesive, multi-layer drug-in-adhesive, reservoir, matrix, or vapor style patches, or could utilize patchless technology. Delivery across the barrier of the skin could also be enhanced using encapsulation, a skin lipid fluidizer, or a hollow or solid microstructured transdermal system (MTS, such as that manufactured by 3M), jet injectors. Additives to the formulation to aid in the passage of therapeutic compounds through the skin include prodrugs, chemicals, surfactants, cell penetrating peptides, permeation enhancers, encapsulation technologies, enzymes, enzyme inhibitors, gels, nanoparticles and peptide or protein chaperones.

One form of controlled-release formulation contains the therapeutic compound or its salt dispersed or encapsulated in a slowly degrading, non-toxic, non-antigenic polymer such as copoly(lactic/glycolic) acid, as described in the pioneering work of Kent et al., U.S. Pat. No. 4,675,189, incorporated by reference herein. The compounds, or their salts, may also be formulated in cholesterol or other lipid matrix pellets, or silastomer matrix implants. Additional slow release, depot implant or injectable formulations will be apparent to the skilled artisan. See, for example, Sustained and Controlled Release Drug Delivery Systems, JR Robinson ed., Marcel Dekker Inc., New York, 1978; and Controlled Release of Biologically Active Agents, R W Baker, John Wiley & Sons, New York, 1987. The foregoing are incorporated by reference in their entirety.

An additional form of controlled-release formulation comprises a solution of biodegradable polymer, such as copoly (lactic/glycolic acid) or block copolymers of lactic acid and PEG, is a bioacceptable solvent, which is injected subcutaneously or intramuscularly to achieve a depot formulation. Mixing of the therapeutic compounds described herein with such a polymeric formulation is suitable to achieve very long duration of action formulations.

When formulated for nasal administration, the absorption across the nasal mucous membrane may be further enhanced by surfactants, such as, for example, glycocholic acid, cholic acid, taurocholic acid, ethocholic acid, deoxycholic acid, chenodeoxycholic acid, dehdryocholic acid, glycodeoxycholic acid, cycledextrins and the like in an amount in the range of between about 0.1 and 15 weight percent, between about 0.5 and 4 weight percent, or about 2 weight percent. An additional class of absorption enhancers reported to exhibit greater efficacy with decreased irritation is the class of alkyl maltosides, such as tetradecylmaltoside (Arnold, J J et al., 2004, J Pharm Sci 93: 2205-13; Ahsan, F et al., 2001, Pharm Res 18:1742046) and references therein, all of which are hereby incorporated by reference.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topical transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When formulated for delivery by inhalation, a number of formulations offer advantages. Adsorption of the therapeutic compound to readily dispersed solids such as diketopiperazines (for example, Technosphere particles [Pfutzner, A and Forst, T, 2005, Expert Opin Drug Deliv 2:1097-1106] or similar structures gives a formulation that results in rapid initial uptake of the therapeutic compound. Lyophilized powders, especially glassy particles, containing the therapeutic compound and an excipient are useful for delivery to the lung with good bioavailability, for example, see Exubera® (inhaled insulin by Pfizer and Aventis Pharmaceuticals Inc.).

Dosage levels of between about 0.01 and about 100 mg/kg body weight per day, preferably 0.5 and about 50 mg/kg body weight per day of the active ingredient compound are useful in the prevention and treatment of disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, gender, diet, time of administration, rate of excretion, drug combination, the severity and course of an infection, the patient's disposition to the infection and the judgment of the treating physician.

The carrier-drug conjugate, fusion or formulation provides advantages to the drug manufacturer and the patient over the unconjugated, unfused or unformulated drug. Specifically, the carrier-drug conjugate or formulation will be a more potent and longer lasting drug requiring smaller and less frequent dosing compared to the unconjugated, unfused or unformulated drug. This translates into lowered healthcare costs and a more convenient drug administration schedule for the patient. The carrier-drug conjugate or formulation can also influence the route of injection of a drug that is normally infused by intravenous injection to now be administered via subcutaneous injection or in a transdermal delivery system. The route of administration via subcutaneous injection or transdermal delivery is most favored because they can be self-administered by patients at home. This can improve patient compliance.

In yet another aspect of the invention, the levels of DBP can be increased as part of the carrier-drug therapy. It has been reported that estrogen can increase DBP levels (Speeckaert et al., Clinica Chimica Acta 371:33). It is contemplated here that levels of DBP can be increased by administration of estrogen for more effective delivery of carrier-drug conjugates.

In yet another aspect of the invention, it is contemplated that the carrier can be used to deliver drugs transdermally. Since DBP normally transports UV activated vitamin D at locations close to the surface of the skin, the use of a transdermal delivery system with the carrier becomes feasible.

In order that the invention described herein may be more fully understood, the following examples are set forth. It should be understood that these examples are for illustrative purposes only and are not to be construed as limiting this invention in any manner.

EXAMPLES

Example 1

Preparation of an Exemplary Thiol-Reactive Carrier Composed of Vitamin $D_3$-PEG with a Maleimide Reactive Group The maleimide on the carrier in this example was used to conjugate to a free cysteine on a protein or peptide in Examples 2 and 3. It is contemplated that the size of the PEG in the scaffolds of the invention are from 0.1 kDa to 100 kDa. Thus, a 2 kDa PEG was selected as a scaffold for this example. The starting materials used in this example were purchased from commercial sources: Vitamin D analog (compound L Toronto Research Chemicals Catalog No. B691610) and the 2 kDa mPEG-maleimide (compound 4, Creative PEGworks Catalog No. PHB-940).

Figure 2:
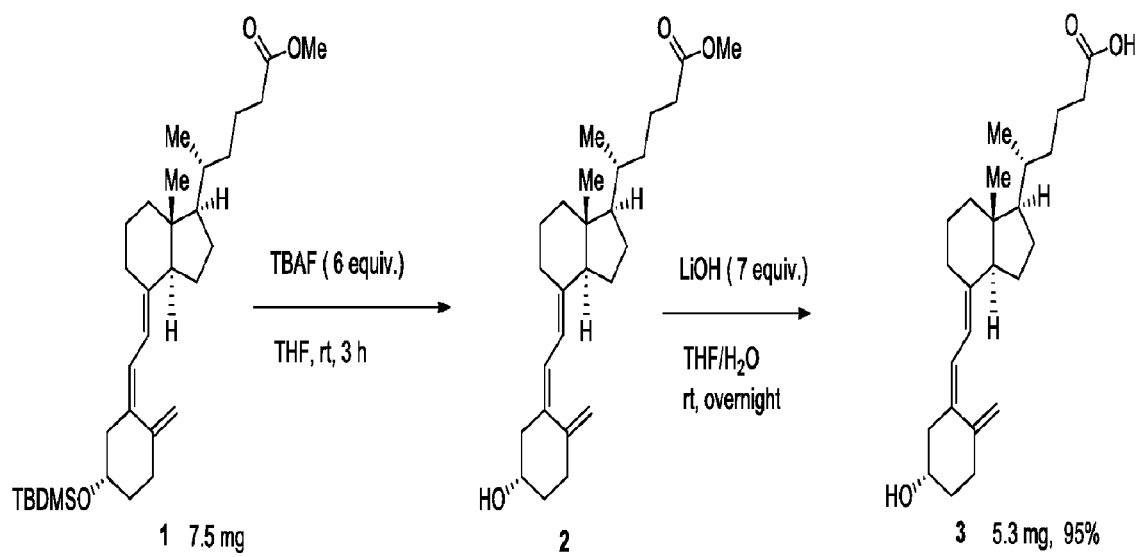
FIG. 2: Reaction scheme showing the chemical structures and syntheses used to generate a carrier, a Vitamin $D_3$-PEG-Maleimide adduct. The carrier was generated by conjugating 1) a Vitamin D analog (the targeting group), 2) a PEG scaffold, and 3) a maleimide coupling group.
Figure 2:
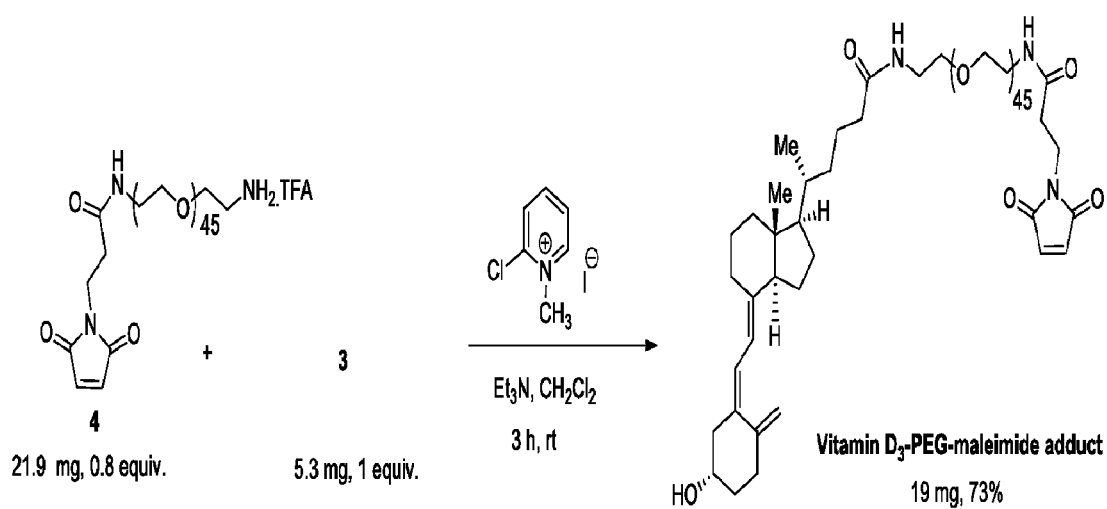

According to FIG. 2, (R)-methyl5-((1R,3aS,7aR,E)-4-((Z)-2-((S)-5-(((tert-butyldimethylsilyl)oxy)-2-methylenecyclohexylidene)ethylidene)-7a-methyloctahydro-1H-inden-1-yl)hexanoate (compound 1, 7.5 mg, 0.0145 mmol, 1 equiv., purchased from Toronto Research Chemicals) was dissolved in anhydrous tetrahydrofuran (0.4 mL) and flushed with nitrogen. Tetrabutylammonium fluoride (22.7 mg, 0.087 mmol, 6 equiv.) was added and the reaction was stirred at room temperature for 3 hours with monitoring by thin layer chromatography (TLC, silica gel, 30% ethyl acetate in hexanes, UV detection, phosphomolybdic acid stain). To the resulting mixture containing compound 2 was added lithium hydroxide monohydrate (4.2 mg, 0.1015 mmol, 7 equiv.), tetrahydrofuran (0.3 mL) and water (0.15 mL). The reaction was flushed with nitrogen and stirred at room temperature for 18 hours. Evaluation by TLC and mass spectroscopy (MS) indicated complete reaction with the presence of expected compound 3. The reaction mixture was diluted with ether (2×15 mL) and washed with 10% aqueous citric acid (30 mL), water (30 mL) and brine (30 mL). The organic layer was dried over anhydrous sodium sulfate and concentrated while maintaining the temperature below 20° C. The sample was further dried under a stream of nitrogen giving ((R)-5-((1R,3aS,7aR,E)-4-4Z)-2-((S)-5-hydroxy-2-methylenecyclohexylidene)ethyl-idene)-7a-methyloctahydro-1H-inden-1-yl)hexanoic acid) (compound 3, 5.3 mg, 95% yield) as a colorless gum. Rf 0.2 (silica gel, 40% EtOAc in hexanes). NMR analysis revealed the presence of about 1.14% of THF and about 0.14% of ether.

Compound 3 (5.3 mg, 0.0137 mmol, 1 equiv.), compound 4 (MAL-PEG-amine TFA salt, 21.9 mg, 0.0109 mmol, 0.8 equiv., purchased from Creative Pegworks) and 2-chloro-1-methylpyridinium iodide (8.7 mg, 0.0342 mmol, 2.5 equiv.) were dissolved in anhydrous dichloromethane (0.5 mL). Triethylamine (7.6 µL, 0.0548 mmol, 4 equiv.) was added and the reaction mixture was stirred for 3 hours at room temperature under nitrogen. The reaction was then diluted with dichloromethane (30 mL) and washed with 10% aqueous citric acid (40 mL), saturated aqueous sodium bicarbonate (30 mL) and brine (30 mL). The organic layer was dried over anhydrous sodium sulfate, filtered and concentrated while maintaining the temperature below 20° C. The sample was further dried under a stream of nitrogen to afford the target compound as a brown gum. Rf 0.6 (silica gel, 20% methanol in dichloromethane). TLC analysis (ninhydrin stain) of the isolated product indicated the absence of compound 4. 1H NMR analysis of the isolated material confirmed its identity and purity. The NMR analysis did not show an appreciable amount of methylene chloride or other solvents.

Example 2

Preparation and Characterization of a Modified FGF21 Protein-Carrier Conjugate

A modified FGF21 was conjugated to the Vitamin $D_3$-PEG-maleimide carrier described in Example 1. As shown below, the FGF21-carrier composition provides significantly improved pharmacokinetic properties when compared to a naturally-occurring FGF21, thereby making the carrier-conjugated molecule an important therapeutic compound for the treatment of diabetes.

FGF21 was expressed in *E. coli*, purified and conjugated to the carrier as follows. A modifi FGF21 was designed to incorporate a free cysteine residue near the amino-terminus of FGF21 to allow site-specific coupling of the protein to the carrier and a His$_6$ tag added for ease of purification. The modified FGF21 coding sequence (SEQ ID NO:4) was computationally optimized for expression in *E. coli*, and the gene was chemically synthesized by a contract research organization (DNA2.0 Menlo Park, Calif.) and cloned into the expression vector pJexpress401 that contains a T5 promoter and a kanamycin resistance gene. The plasmid was transformed into *E. coli* Origami2 cells (EMD Biosciences Inc.). Expression of the FGF21 from the pJexpress401 vector in the Origami strain was accomplished as follows. Luria Broth plus 1% glucose was inoculated with an overnight culture at a 1:100 dilution and grown to log phase where the OD600 was 0.6. Then the culture temperature was reduced from 37° C. to 18° C. and the culture was induced using 0.2 mM IPTG and grown overnight at 18° C. while shaking at 180 rpm. Cells were harvested, lysed and the supernatant collected. The protein was affinity purified using immobilized metal affinity chromatography (IMAC) resin and polished by ion exchange chromatography.

Purified FGF21 protein was then buffer exchanged into 10 mM Tris pH 8.0, 50 mM NaCl, 1 mM EDTA. Conjugation to the Vitamin D$_3$-PEG-maleimide carrier molecule (Example 1) was accomplished by mixing the thiol-reactive carrier dissolved in DMSO at 10 mg/mL with the FGF21 protein containing a free cysteine (SEQ ID NO:3) at 0.5 mg/mL in a molar ratio of 2:1 carrier to protein. The conjugated protein was separated from unreacted components by ion exchange chromatography. Conjugation and purity was confirmed by SDS-PAGE. FGF21 alone and the FGF21-carrier conjugate were then buffer exchanged to PBS and sterilized using a 0.22 micron filter for use in the animal study.

Figure 3:
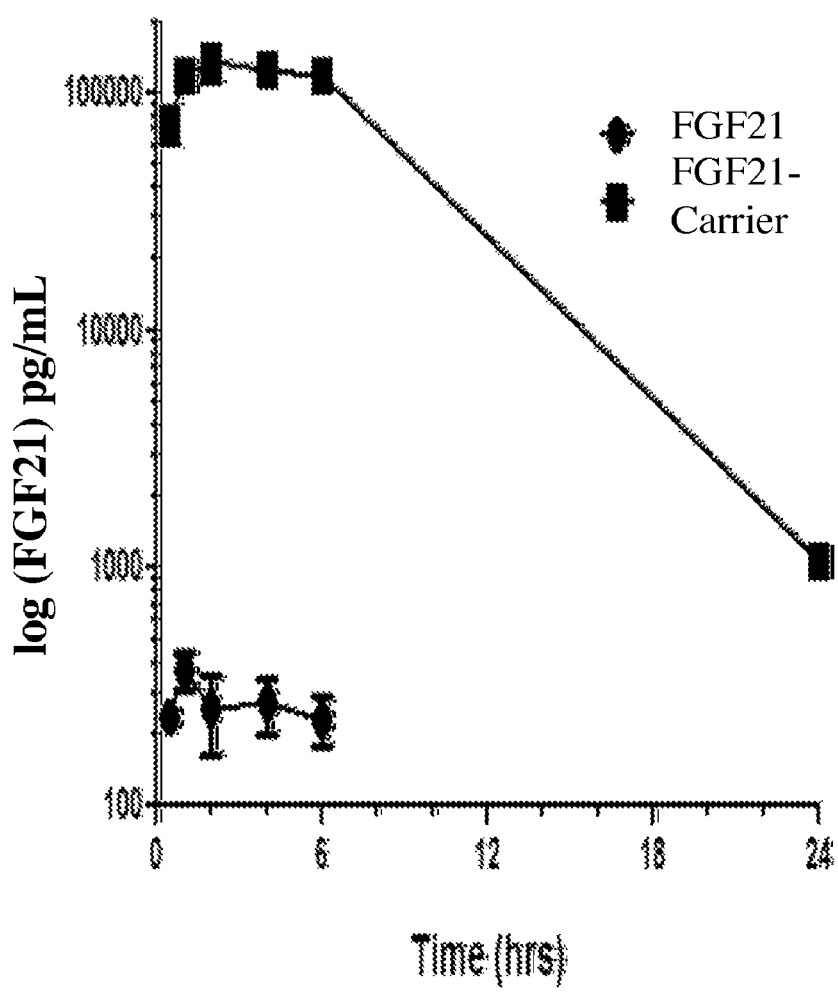
FIG. 3: Bioavailability and pharmacokinetics of an FGF21-carrier conjugate. FGF21 alone (SEQ ID NO:3) or conjugated to the Vitamin $D_3$-PEG-Maleimide carrier were injected subcutaneously into Sprague Dawley rats at 0.1 mg/kg. Plasma samples were analyzed for FGF21 concentration by ELISA in duplicate and an average from 3-5 animals per time point were plotted on the semi-log plot graph.

Pharmacokinetics of FGF21 (SEQ ID NO:3) or the FGF21-carrier conjugate was studied in Sprague Dawley rats. Briefly, 0.1 mg/kg of each molecule was injected separately into the rats by SC injection. Samples of plasma were collected at 30 mins, 60 mins, 120 mins, 240 mins, 360 mins, 24 hrs and 48 hrs. Samples were analyzed using a commercial ELISA kit validated for FGF21 (Millipore, Cat. #EZH-FGF21-19K). The results show a significant difference in absorption following SC administration between the FGF21 and the FGF21-carrier conjugate at the following time points (30, 60, 120 and 240 mins), beyond which FGF21 levels began to decline (FIG. 3). These data show that the conjugation of carrier to FGF21 significantly increased the bioavailability of FGF21 following SC injection (380-fold increase, calculated by dividing the average Cmax of FGF21, 376 pg/mL from average Cmax of the FGF21-carrier conjugate, 143526 pg/mL). The area under the curve (AUC) was also calculated as 1047980 h*pg/mL for the FGF21-carrier conjugate and 1551 h*pg/mL for FGF21 alone. Therefore, there was a 675-fold increase in drug exposure when dividing the mean AUC of FGF21-carrier conjugate from the mean AUC of FGF21. Together, the data demonstrates the utility of the carrier molecule in increasing the bioavailability and indicates that conjugated FGF21 has significant pharmacokinetic advantages over the native FGF21.

Example 3

Preparation and Characterization of a Ghrelin Peptide-Carrier Conjugate

In this example, conjugation of the Vitamin D$_3$-PEG-maleimide carrier generated in Example 1 to ghrelin imparted a significantly longer half-life on ghrelin, thereby making the conjugated molecule a potentially useful therapeutic for the treatment of cachexia, anorexia and/or frailty in the elderly.

A synthetic rat ghrelin peptide with an added C-terminal cysteine was purchased from Innovagen (Lund, Sweden, SEQ ID NO:6). The Vitamin D$_3$-PEG-maleimide carrier as described in Example 1 was selected to be proportional in size to a 2-3 kDa peptide so that conjugation might not significantly affect the bioactivity. Conjugation with the carrier was accomplished by mixing a thiol reactive carrier (from Example 1) dissolved in DMSO at 10 mg/mL with the ghrelin peptide containing a free cysteine at a concentration of 1 mg/mL in 15 mM MES pH 6.0, 1 mM EDTA in a molar ratio of 2:1 carrier to peptide. The conjugated peptide was separated from unreacted components by ion exchange chromatography. Conjugation and purity was confirmed by SDS-PAGE. Rat ghrelin (rGhrelin) peptide and the rGhrelin-carrier conjugates were then buffer exchanged to PBS and filter sterilized using a 0.22 micron filter for use in the animal study.

Figure 4:
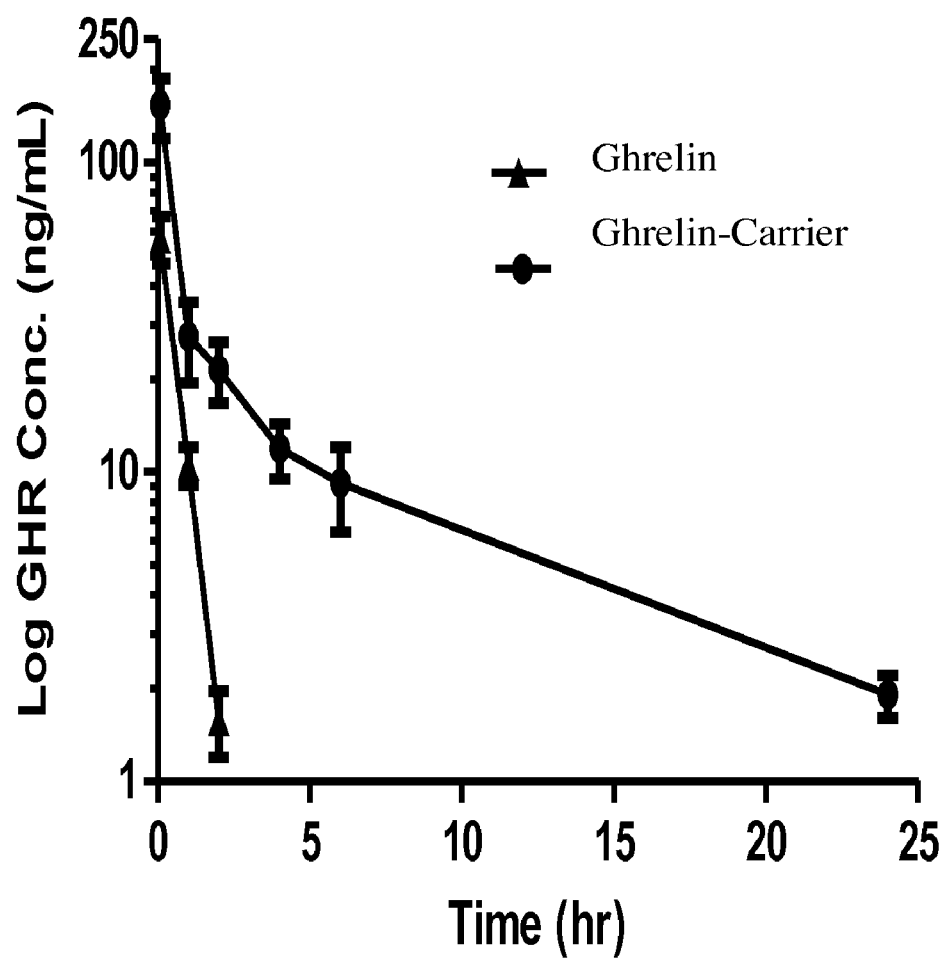
FIG. 4: Pharmacokinetics of Ghrelin-carrier conjugate. Ghrelin (SEQ ID NO:6) alone or conjugated to the Vitamin $D_3$-PEG-Maleimide carrier were injected intravenously into Sprague Dawley rats at 0.1 mg/kg. Plasma samples were analyzed for Ghrelin concentration by ELISA in duplicate and an average from 3-5 animals per time point were plotted on the semi-log plot graph.

Pharmacokinetics of rGhrelin (SEQ ID NO:6) or the rGhrelin-carrier conjugate was studied in Sprague Dawley rats. Briefly, 0.1 mg/kg of each molecule was injected separately into the rats by intravenous (IV) injection. Samples of plasma were collected at 30 mins, 60 mins, 120 mins, 240 mins, 360 mins, 24 hrs and 48 hrs. Samples were analyzed using a commercial ELISA kit validated for analyzing rGhrelin from rat plasma (Millipore, Cat. #EZRGRT-91K). The results show significant differences in the pharmacokinetic profiles of rGhrelin and the rGhrelin-carrier conjugate (FIG. 4). Calculation of the half-life using WinNonLin revealed a 0.37 hr half-life for rGhrelin and an 8 hr half-life for the rGhrelin-carrier conjugate, which is calculated to be a 22-fold improvement. The data demonstrate a second example of the usefulness of the carrier molecule in increasing half-life. Thus, ghrelin in a conjugated form is a useful therapeutic for the treatment of ghrelin-responsive diseases such as cachexia, anorexia and frailty in the elderly.

Example 4

Assessment of the Receptor Binding Activity of a Ghrelin Peptide-Carrier

The activity of the ghrelin peptide, when conjugated to a carrier, was not adversely affected by the presence of the scaffold and targeting groups. To show this, ghrelin (SEQ ID:5) and Vitamin D$_3$-PEG-maleimide carrier-conjugated ghrelin from Example 3 were compared for receptor binding and activation of a ghrelin receptor (agonist activity) using a cell-based receptor agonist assay as described below.

The test compounds were added to GHS-R-expressing CHO-K1 cell cultures. Ghrelin binds and activates the GHS-R receptor and intracellular calcium responses were assessed as an indicator of agonist activity. The activity was measured by a calcium flux-based assay developed by GenScript USA Inc. for the FLIPR™ (Fluorescence Imaging Plate Reader) high-throughput cellular screening instrument.

CHO-K1 cells expressing GHS-R were cultured in Ham's F12 supplemented with 10% fetal bovine serum, 500 mg/mL G418 and were passaged in order to maintain optimal cell health. The cells were seeded in a 384-well black-wall, clear-bottom plate at a density of 20,000 cells per well in 20 μL of growth medium 18 hours prior to the assay and maintained at 37° C./5% CO$_2$. At the beginning of the assay, 20 μL of Calcium-4 loading buffer was added into the wells. The plate was incubated in the dark at 37° C. for 60 minutes then at room temperature for 15 minutes. The ghrelin and ghrelin-conjugate test articles were at an initial concentration of 1 mM in DMSO. The test articles were serially diluted 10-fold in Hank's Buffered Saline Solution (HBSS) with 20 mM HEPES buffer pH 7.4 prior to addition to the test plates. The final concentration of each test article was 5× the concentration before addition to the cells. The intracellular calcium levels in the cells were measured for 20 seconds using the FLIPR™ instrument prior to addition of the test articles. Ten µL of each diluted test article was added to the plate to make a final volume of 50 µL. Changes in intracellular calcium levels were measured for an additional 100 sec (21 to 120 seconds).

The average value of the 20 second reading (1 to 20 seconds) was calculated as the baseline reading and the relative fluorescent units ($\Delta$RFU) intensity values were calculated with the maximal fluorescent units (21 to 120 seconds) subtracting the average value of baseline reading. Data acquisition and analyses was performed using ScreenWorks® (version 3.1) and exported to Excel.

The % activation of compound was calculated using the following equation:

$$\% \text{ activation} = (\Delta\text{RFU}_{compound} - \Delta\text{RFU}_{Background}) / (\Delta\text{RFU}_{Agonist\ control} - \Delta\text{RFU}_{Background}) \} *100\%$$

activation was then plotted as a function of the log of the cumulative doses of compounds. The data represent the average of duplicate determinations. The EC50 was determined using a data analysis wizard written by GenScript.

The EC50 value of ghrelin without carrier was 88.5 nM. In comparison, the carrier-conjugated ghrelin had an EC50 value of 85 nM, which is nearly identical to the control peptide. Thus, the agonist activity of the peptide was preserved following conjugation of the carrier to the ghrelin peptide. Note that the assays were done in the presence of 10% serum that contains DBP. No interference in receptor binding and activation was observed for the carrier-conjugated peptide.

Example 5

Preparation of an Exemplary Amine-Reactive Carrier Composed of Vitamin $D_3$-PEG with a NHS-Reactive Group NHS-reactive groups on carriers were generated for conjugation to amine groups on proteins. A 2 kDa PEG was selected as a scaffold for this example. The starting materials used in this example were purchased from Toronto Research Chemicals for the Vitamin D analog (compound 1) and from Creative Pegworks for the 2 kDa mPEG-amino acid (compound 5).

Figure 5:
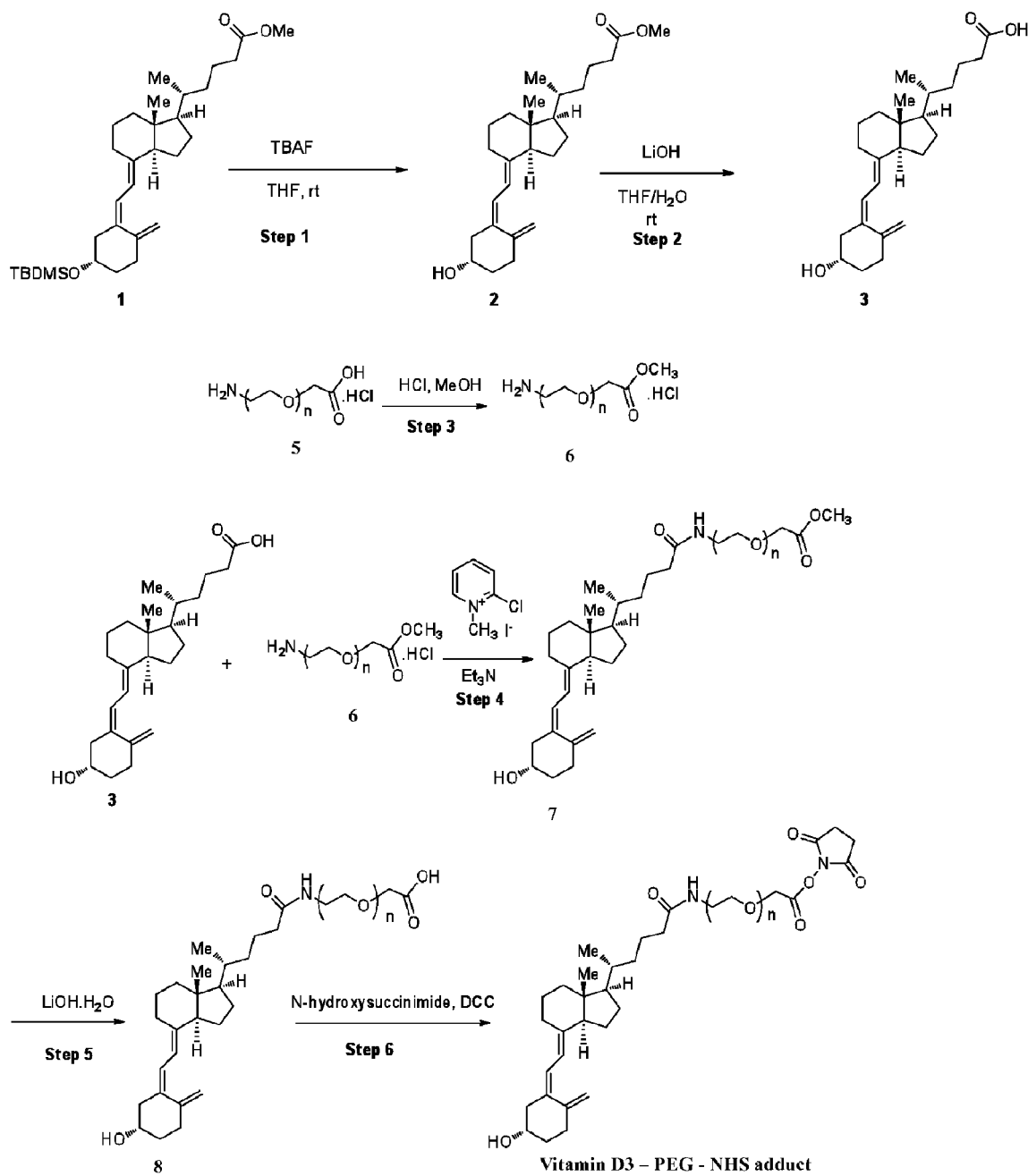
FIG. 5: Reaction scheme showing the chemical structures and syntheses used to generate another carrier, a Vitamin $D_3$-PEG-NHS adduct. The carrier was generated by conjugating 1) a Vitamin D analog (the targeting group), 2) a PEG scaffold, and 3) an NHS coupling group.

According to FIG. 5 (steps 1 and 2): (R)-Methyl-5-((1R,3aS,7aR,E)-4-((Z)-2-((S)-5-((tert-butyldimethylsilyl)oxy)-2-methylenecy-clohexylidene)ethylidene)-7a-methyloctahydro-1H-inden-1-yl)hexanoate (compound 1, 8.2 mg, 0.0159 mmol, 1 equiv.) was dissolved in anhydrous tetrahydrofuran (THF, 0.4 mL) and the mixture was flushed with nitrogen. Tetrabutylammonium fluoride solution (25 mg, 0.096 mmol, 6 equiv.) was added and the reaction mixture was stirred at room temperature for 3 hr with monitoring by thin layer chromatography (TLC, silica gel, 30% ethyl acetate in hexanes, UV detection, phosphomolybdic acid stain). To the resulting mixture containing compound 2, lithium hydroxide monohydrate (4.6 mg, 0.109 mmol, 7 equiv.), THF (0.3 mL), and water (0.16 mL) were added. The reaction mixture was flushed with nitrogen and stirred at room temperature for 18 hr. Evaluation by TLC and mass spectroscopy (MS) indicated complete reaction with the presence of the expected compound 3. The reaction mixture was diluted with ether (10 mL) and washed with 10% aqueous citric acid (10 mL), water (10 mL) and brine (10 mL). The organic layer was dried over anhydrous sodium sulfate and concentrated while maintaining the temperature below 20° C. The sample was further dried under a stream of nitrogen giving ((R)-5-((1R,3aS,7aR,E)-4-((Z)-2-((S)-5-hydroxy-2-methylenecyclo-hexylidene)ethyl-indene)-7a-methyloctahydro-1H-inden-1-yl)hexanoic acid (compound 3, 6.1 mg, 99% yield) as a colorless gum. Rf 0.2 (silica gel, 40% ethyl acetate (EtOAc) in hexanes). Nuclear magnetic resonance spectroscopy (NMR) analysis revealed the presence of ~7% of ether.

According to FIG. 5 (step 3): to a solution of PEG-amino acid 4 (18.5 mg, 0.0092 mmol, purchased from Creative Pegworks) in anhydrous methanol, HCl in dioxane (4 M, 1.5 mL) was added, and the reaction mixture was heated at 70° C. in a sealed tube for 20 hr. The reaction was monitored by TLC (ninhydrin stain), and upon completion of the reaction, it was concentrated on a rotavap. The residue was co-evaporated with dichloromethane (3×5 mL) and ether (3×5 mL) to a pale yellow foam, which was suspended in ether (5 mL). The liquid was decanted and the solid obtained was dried to isolate the desired product 5 (14 mg, 75%) as a pale yellow solid. Rf 0.2 (silica gel, 20% methanol (MeOH)/DCM/0.2% NH4OH). NMR analysis did not show an appreciable amount of methylene chloride or ether.

According to FIG. 5 (step 4): compound 3 (3.4 mg, 0.009 mmol, 1 equiv.), compound 6 (methyl ester PEG-amine HCl salt, 14 mg, 0.007 mmol, 0.8 equiv.) and 2-chloro-1-methylpyridinium iodide (5.6 mg, 0.022 mmol, 2.5 equiv.) were dissolved in anhydrous dichloromethane (0.6 mL). Triethylamine (5 µL, 0.0356 mmol, 4 equiv.) was added and the reaction mixture was stirred for 3 hr at room temperature under nitrogen. The reaction was incomplete at this time, therefore an additional amount of compound 3 (1.7 mg, 0.0045 mmol) was added and the reaction was continued further 3 hr, then diluted with dichloromethane (10 mL) and washed with 10% aqueous citric acid (10 mL), saturated aqueous sodium bicarbonate (10 mL) and brine (10 mL). The organic layer was dried over anhydrous sodium sulfate, filtered and concentrated while maintaining the temperature below 20° C. The sample was purified by silica gel (2 g) flash chromatography. The column was first eluted with ethyl acetate to remove unreacted compound 3 and then with 1-10% MeOH/dichloromethane (20 mL each). Fractions containing pure product were combined together and evaporated on a rotavap, while maintaining the temperature below 20° C. The sample was dried under a stream of nitrogen to afford compound 7 as a brown gum (10 mg, 60%). Rf 0.3 (silica gel, 5% MeOH in dichloromethane). TLC analysis (ninhydrin stain) of the isolated product indicated the absence of compound 6. 1H NMR analysis of the isolated material confirmed its identity and purity. The NMR analysis revealed the presence of 1.1% of methylene chloride.

According to FIG. 5 (step 5): compound 7 (10 mg, 0.0042 mmol) was dissolved in a mixture of THF (0.2 mL) and a drop of methanol. To this solution was added lithium hydroxide monohydrate solution (0.9 mg, 0.021 mmol, 5 equiv. in 0.1 mL of water). The reaction mixture was flushed with nitrogen and stirred at room temperature for 18 hr. Evaluation by TLC indicated complete reaction with the presence of compound 8. The reaction mixture was diluted with dichloromethane (10 mL) and washed with 10% aqueous citric acid (10 mL) and brine (10 mL). The organic layer was dried over anhydrous sodium sulfate and concentrated while maintaining the temperature below 20° C. The sample was further dried under a stream of nitrogen giving the desired Vitamin-$D_3$-PEG-acid (compound 8, 7 mg, 71% yield) as a brown gum. Rf 0.2 (silica gel, 10% MeOH/dichloromethane). NMR analysis revealed the presence of ~2% of dichloromethane.

Stock solutions were prepared: 34 g of N-hydroxysuccinimide in 1 mL of anhydrous dimethylformamide (DMF) and 61 mg of dicyclohexylcarbodiimide (DCC) in 1 mL of anhydrous dichloromethane According to FIG. 5 (step 6): to a solution of compound 8 (7 mg, 0.003 mmol, 1 equiv.) in dichloromethane (0.3 mL) was added a solution of N-hydroxysuccinimide in DMF (10 µL, 0.34 mg, 0.003 mmol) followed by a solution of DCC in dichloromethane (10 µL, 0.61 mg, 0.003 mmol) and the reaction mixture was flushed with nitrogen and stirred for 20 hr. Since the reaction was incomplete as indicated by TLC, additional amounts of N-hydroxysuccinimide in DMF (25 µL, 0.85 mg, 0.0075 mmol) and DCC in dichloromethane (25 µL, 1.53 mg, 0.0075 mmol) were added and the reaction was continued for another 20 hr. Chloroform (10 mL) was added to the reaction mixture, and it was washed with water (10 mL). The organic phase was dried over sodium sulfate and the removal of solvent provided the desired target compound Vitamin $D_3$-PEG-NHS (7.0 mg, crude). $^1$H NMR and TLC ($R_f$: 0.3, 10% MeOH/chloroform) of this material indicated the presence of desired material. Vitamin $D_3$-PEG-NHS carrier was then used in Example 6.

Example 6

Preparation and Characterization of an Antibody-Carrier Conjugate

The infliximab-carrier conjugate of showed increased serum concentrations and bioavailability in rats when compared to infliximab alone.

Infliximab, sold as a lyophilized powder with the appropriate salts (Hannah Pharmaceuticals), was resuspended to a concentration of 10 mg/mL with water. The Vitamin $D_3$-PEG-NHS carrier was resuspended at a concentration of 10 mg/mL in DMSO. The Vitamin $D_3$-PEG-NHS carrier and the infliximab were then mixed at a molar ratio of 5:1 and 10:1 carrier to infliximab. A therapeutic compound carrier conjugate of the invention typically has at least 1 and could be between 1-10 carrier molecules individually attached to a therapeutic compound. By using an NHS version of the carrier, more than one carrier can be attached to a therapeutic protein and this can be experimentally controlled by altering the molar ratio of carrier to target therapeutic in the reaction. In this example, a target distribution of 2-4 carriers was set as a desired parameter. By testing two different molar ratios and examining the resulting conjugates by mass spectrometry, an actual ratio was determined.

The infliximab and infliximab NHS-carrier conjugates were separated from unconjugated carrier by use of a desalting column with a 40 kDa cutoff (Zeba Spin, Thermo Scientific). Mass spectrometry was used to calculate the intact mass of infliximab in the reactions. The results show that unmodified infliximab had a mass predominantly of 149 kDa. The mass of the carrier-conjugated infliximab had a mass in increasing ratios with an average attachment of the 3 kDa carrier of 2-4 carriers per antibody.

Figure 6:
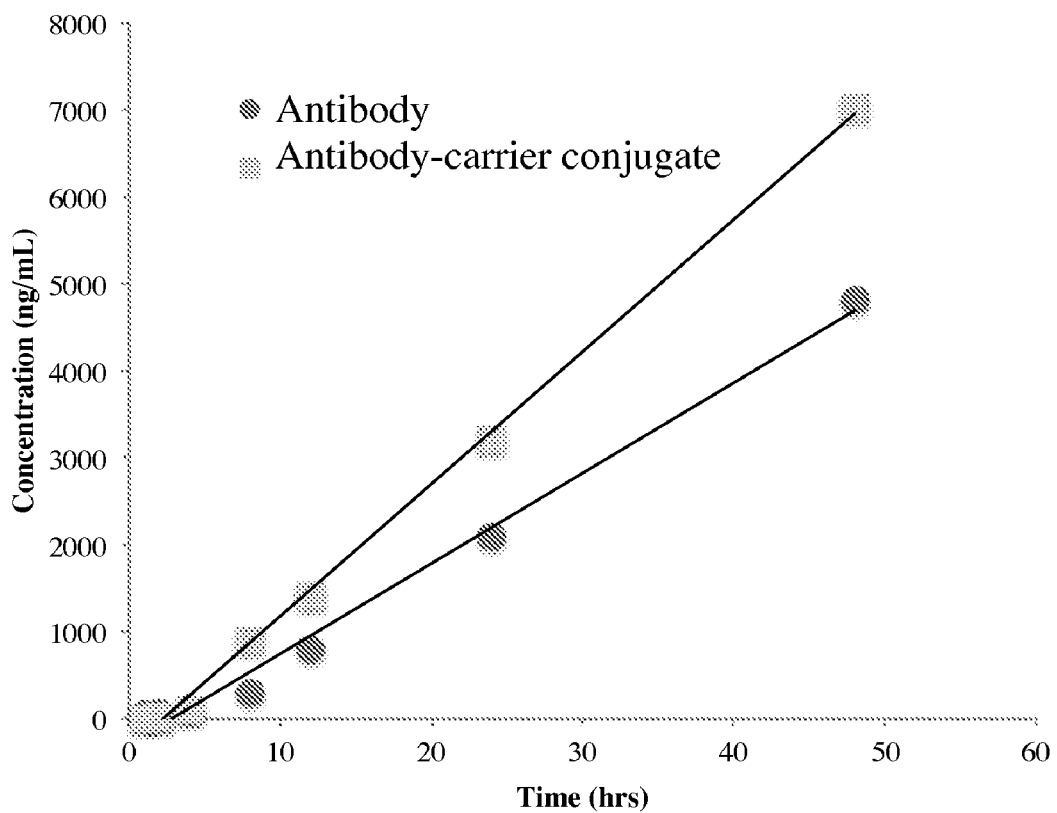
FIG. 6: Bioavailability and pharmacokinetics of an infliximab-carrier conjugate. Infliximab alone or conjugated to the Vitamin $D_3$-PEG-NHS carrier was injected subcutaneously into Sprague Dawley rats at 1 mg/kg. Plasma samples were analyzed for infliximab concentration by an infliximab-specific ELISA and an average from 3 animals per time point were plotted on a linear plot graph.

The purified 5:1 reaction product was then used in a rat pharmacokinetic study comparing infliximab to the infliximab-carrier conjugate administered subcutaneously (SC). The dose was 1 mg/kg in all test groups with three rats per group. Serum samples were collected pre-dosing and at various times from 5 min to 48 hrs post injection. Serum samples were then analyzed by ELISA using an ELISA kit specific for determining the levels of infliximab in serum (Promonitor™, Progenika™). Pharmacokinetic parameters were determined using WinNonLin. The results shown in FIG. 6 demonstrate a 1.5-fold improvement in serum concentration and area under the curve (AUC) when the antibody is conjugated to the Vitamin $D_3$-PEG-NHS carrier when compared to the unconjugated antibody. More specifically, at the 24 hr and 48 hr time points, a concentration of 2100 ng/mL and 4800 ng/mL are observed for infliximab. In contrast, at the 24 hr and 48 hr time points, a concentration of 3200 ng/mL and 7000 ng/mL are observed for carrier conjugated-infliximab. This translates into a 50% improvement in bioavailability. The AUC calculation showed a 50% improvement (FIG. 6). Thus, this example shows the utility of the carrier in improving the serum concentration and bioavailability of infliximab when compared to the unconjugated antibody.

Exemplary Sequences

```
Human FGF21 protein sequence
                                                 SEQ ID NO: 1
MDSDETGFEHSGLWVSVLAGLLLGACQAHPIPDSSPLLQFGGQVRQRYLYTDDAQQTE

AHLEIREDGTVGGAADQSPESLLQLKALKPGVIQILGVKTSRFLCQRPDGALYGSLHF

DPEACSFRELLLEDGYNVYQSEAHGLPLHLPGNKSPHRDPAPRGPARFLPLPGLPPAL

PEPPGILAPQPPDVGSSDPLSMVGPSQGRSPSYAS

Mature human FGF21 protein sequence
                                                 SEQ ID NO: 2
HPIPDSSPLLQFGGQVRQRYLYTDDAQQTEAHLEIREDGTVGGAADQSPESLLQLKALK

PGVIQILGVKTSRFLCQRPDGALYGSLHFDPEACSFRELLLEDGYNVYQSEAHGLPLHL

PGNKSPHRDPAPRGPARFLPLPGLPPALPEPPGILAPQPPDVGSSDPLSMVGPSQGRSP

SYAS

Modified mature human FGF21 protein sequence (N-terminal
6-his tag, tev cleavage site, an additional 182P at the C
terminus, and modifications to the following residues using
the numbering of the mature human FGF21 sequence: I3C, and
G170E)
                                                 SEQ ID NO: 3
MGSHHHHHHSSGENLYFQGHPCPDSSPLLQFGGQVRQRYLYTDDAQQTEAHLEIREDGT

VGGAADQSPESLLQLKALKPGVIQILGVKTSRFLCQRPDGALYGSLHFDPEACSFRELL
```

LEDGYNVYQSEAHGLPLHLPGNKSPHRDPAPRGPARFLPLPGLPPALPEPPGILAPQPP

DVGSSDPLSMVEPSQGRSPSYASP

Optimized coding sequence for FGF21 expression in E. coli
(see amino acids SEQ ID NO: 3)
SEQ ID NO: 4
ATGGGCTCACATCATCACCACCATCATAGCAGCGGAGAGAACTTGTATTTTCAGGGA

CATCCGTGCCCTGACAGCAGCCCGCTGCTGCAGTTCGGTGGTCAAGTCCGTCAGCGT

TACCTGTACACTGACGACGCGCAACAGACCGAGGCGCACCTGGAAATTCGCGAAGAT

GGTACGGTGGGTGGCGCAGCGGACCAAAGCCCGGAGTCCCTGTTGCAGCTGAAGGCC

CTGAAGCCGGGTGTCATCCAAATCCTGGGCGTTAAAACCAGCCGTTTTCTGTGCCAA

CGTCCGGATGGTGCGCTGTACGGTTCCCTGCACTTCGACCCAGAGGCATGTAGCTTT

CGTGAACTGCTGCTGGAAGATGGCTATAATGTGTACCAGTCTGAGGCGCACGGTCTG

CCGTTGCACTTGCCGGGTAACAAAAGCCCGCACCGCGACCCAGCACCGCGTGGTCCG

GCTCGCTTCCTGCCGCTGCCGGGTCTGCCTCCGGCGCTGCCGGAGCCGCCAGGCATT

CTGGCTCCGCAACCGCCGGATGTTGGCAGCAGCGATCCGCTGAGCATGGTTGAACCG

TCGCAGGGCCGCAGCCCGTCTTATGCCAGCCCGTAA

Human Ghrelin protein sequence
SEQ ID NO: 5
GS(n-octanoyl-S)FLSPEHQRVQQRKESKKPPAKLQPR Rat Ghrelin with added C-term cys
SEQ ID NO: 6
GS(n-octanoyl-S)FLSPEHQKAQQRKESKKPPAKLQPRC DBP protein sequence
SEQ ID NO: 7
MKRVLVLLLAVAFGHALERGRDYEKNKVCKEFSHLGKEDFTSLSLVLYSRKFPSGTFE

QVSQLVKEVVSLTEACCAEGADPDCYDTRTSALSAKSCESNSPFPVHPGTAECCTKEG

LERKLCMAALKHQPQEFPTYVEPTNDEICEAFRKDPKEYANQFMWEYSTNYGQAPLSL

LVSYTKSYLSMVGSCCTSASPTVCFLKERLQLKHLSLLTTLSNRVCSQYAAYGEKKSR

LSNLIKLAQKVPTADLEDVLPLAEDITNILSKCCESASEDCMAKELPEHTVKLCDNLS

TKNSKFEDCCQEKTAMDVFVCTYFMPAAQLPELPDVELPTNKDVCDPGNTKVMDKYTF

ELSRRTHLPEVFLSKVLEPTLKSLGECCDVEDSTTCFNAKGPLLKKELSSFIDKGQEL

CADYSENTFTEYKKKLAERLKAKLPDATPTELAKLVNKHSDFASNCCSINSPPLYCDS

EIDAELKNIL

DBP nucelotide sequence
SEQ ID NO: 8
TTTAATAATAATTCTGTGTTGCTTCTGAGATTAATAATTGATTAATTCATAGTCAGGA

ATCTTTGTAAAAAGGAAACCAATTACTTTTGGCTACCACTTTTACATGGTCACCTACA

GGAGAGAGGAGGTGCTGCAAGACTCTCTGGTAGAAAAATGAAGAGGGTCCTGGTACTA

CTGCTTGCTGTGGCATTTGGACATGCTTTAGAGAGAGGCCGGGATTATGAAAAGAATA

AAGTCTGCAAGGAATTCTCCCATCTGGGAAAGGAGGACTTCACATCTCTGTCACTAGT

CCTGTACAGTAGAAAATTTCCCAGTGGCACGTTTGAACAGGTCAGCCAACTTGTGAAG

GAAGTTGTCTCCTTGACCGAAGCCTGCTGTGCGGAAGGGGCTGACCCTGACTGCTATG

ACACCAGGACCTCAGCACTGTCTGCCAAGTCCTGTGAAAGTAATTCTCCATTCCCCGT

TCACCCAGGCACTGCTGAGTGCTGCACCAAAGAGGGCCTGGAACGAAAGCTCTGCATG

GCTGCTCTGAAACACCAGCCACAGGAATTCCCTACCTACGTGGAACCCACAAATGATG

AAATCTGTGAGGCGTTCAGGAAAGATCCAAAGGAATATGCTAATCAATTTATGTGGGA

-continued

ATATTCCACTAATTACGGACAAGCTCCTCTGTCACTTTTAGTCAGTTACACCAAGAGT

TATCTTTCTATGGTAGGGTCCTGCTGTACCTCTGCAAGCCCAACTGTATGCTTTTTGA

AAGAGAGACTCCAGCTTAAACATTTATCACTTCTCACCACTCTGTCAAATAGAGTCTG

CTCACAATATGCTGCTTATGGGGAGAAGAAATCAAGGCTCAGCAATCTCATAAAGTTA

GCCCAAAAAGTGCCTACTGCTGATCTGGAGGATGTTTTGCCACTAGCTGAAGATATTA

CTAACATCCTCTCCAAATGCTGTGAGTCTGCCTCTGAAGATTGCATGGCCAAAGAGCT

GCCTGAACACACAGTAAAACTCTGTGACAATTTATCCACAAAGAATTCTAAGTTTGAA

GACTGTTGTCAAGAAAAAACAGCCATGGACGTTTTTGTGTGCACTTACTTCATGCCAG

CTGCCCAACTCCCCGAGCTTCCAGATGTAGAGTTGCCCACAAACAAAGATGTGTGTGA

TCCAGGAAACACCAAAGTCATGGATAAGTATACATTTGAACTAAGCAGAAGGACTCAT

CTTCCGGAAGTATTCCTCAGTAAGGTACTTGAGCCAACCCTAAAAAGCCTTGGTGAAT

GCTGTGATGTTGAAGACTCAACTACCTGTTTTAATGCTAAGGGCCCTCTACTAAAGAA

GGAACTATCTTCTTTCATTGACAAGGGACAAGAACTATGTGCAGATTATTCAGAAAAT

ACATTTACTGAGTACAAGAAAAAACTGGCAGAGCGACTAAAAGCAAAATTGCCTGATG

CCACACCCACGGAACTGGCAAAGCTGGTTAACAAGCACTCAGACTTTGCCTCCAACTG

CTGTTCCATAAACTCACCTCCTCTTTACTGTGATTCAGAGATTGATGCTGAATTGAAG

AATATCCTGTAGTCCTGAAGCATGTTTATTAACTTTGACCAGAGTTGGAGCCACCCAG

GGGAATGATCTCTGATGACCTAACCTAAGCAAAACCACTGAGCTTCTGGGAAGACAAC

TAGGATACTTTCTACTTTTCTAGCTACAATATCTTCATACAATGACAAGTATGATGA

TTTGCTATCAAAATAAATTGAAATATAATGCAAACCATAAAAAAAAAAAAAAAAAAA

AAA

Tumor necrosis factor-alpha (TNF-α)
SEQ ID NO: 9

ATGAGCACTGAAAGCATGATCCGGGACGTGGAGCTGGCCGAGGAGGCGCTCCCCAAG

AAGACAGGGGGGCCCCAGGGCTCCAGGCGGTGCTTGTTCCTCAGCCTCTTCTCCTTC

CTGATCGTGGCAGGCGCCACCACGCTCTTCTGCCTGCTGCACTTTGGGGTGATCGGC

CCCCAGAGGGAAGAGTTCCCCAGGGACCTCTCTCTAATCAGCCCTCTGGCCCAGGCA

GTCAGATCATCTTCTCGAACCCCGAGTGACAAGCCTGTAGCCCATGTTGTAGCAAAC

CCTCAAGCTGAGGGGCAGCTCCAGTGGCTGAACCGCCGGGCCAATGCCCTCCTGGCC

AATGGCGTGGAGCTGAGAGATAACCAGTTGGTGGTGCCATCAGAGGGCCTGTACCTC

ATCTACTCCCAGGTCCTCTTCAAGGGCCAAGGCTGCCCCTCCACCCATGTGCTCCTC

ACCCACACCATCAGCCGCATCGCCGTCTCCTACCAGACCAAGGTCAACCTCCTCTCT

GCCATCAAGAGCCCCTGCCAGAGGGAGACCCCAGAGGGGGCTGAGGCCAAGCCCTGG

TATGAGCCCATCTATCTGGGAGGGGTCTTCCAGCTGGAGAAGGGTGACCGACTCAGC

GCTGAGATCAATCGGCCCGACTATCTCGACTTTGCCGAGTCTGGGCAGGTCTACTTT

GGGATCATTGCCCTGTGA

Tumor necrosis factor-alpha (TNF-α)
SEQ ID NO: 10
MSTESMIRDVELAEEALPKKTGGPQGSRRCLFLSLFSFLIVAGATTLFCLLHFGVIG

PQREEFPRDLSLISPLAQAVRSSSRTPSDKPVAHVVANPQAEGQLQWLNRRANALLA

NGVELRDNQLVVPSEGLYLIYSQVLFKGQGCPSTHVLLTHTISRIAVSYQTKVNLLS

```
AIKSPCQRETPEGAEAKPWYEPIYLGGVFQLEKGDRLSAEINRPDYLDFAESGQVYF

GIIAL
```

All publications and patent documents disclosed or referred to herein are incorporated by reference in their entirety. The foregoing description has been presented only for purposes of illustration and description. This description is not intended to limit the invention to the precise form disclosed. It is intended that the scope of the invention be defined by the claims appended hereto.

What is claimed:

1. A carrier-drug conjugate, comprising a targeting group comprising vitamin D that is not hydroxylated at the Carbon 1 position stably linked to a therapeutic peptide.

2. The carrier-drug conjugate of claim 1, wherein said targeting group is linked to said therapeutic peptide via a scaffold that is poly(ethylene glycol).

3. The carrier drug conjugate of claim 2, wherein said scaffold is between about 100 Da and 200,000 Da.

4. A pharmaceutical composition comprising a carrier-drug conjugate comprising a targeting group that is vitamin D that is not hydroxylated at the Carbon 1 position linked to a therapeutic peptide via a scaffold that is between 300 Da and 60,000 Da.

5. The pharmaceutical composition of claim 4, wherein said carrier increases the absorption, bioavailability, or half-life of said therapeutic peptide in circulation.

6. The pharmaceutical composition of claim 5 wherein said scaffold is poly(ethylene glycol).

7. The carrier-drug conjugate of claim 1, wherein said therapeutic peptide has FGF21 activity and comprises an amino acid sequence with at least a 90% sequence identity to SEQ ID NO:2.

8. The carrier-drug conjugate of claim 7, further comprising a scaffold.

9. The carrier-drug conjugate of claim 8, wherein said scaffold is poly(ethylene glycol).

10. A method of treating a patient in need of a therapeutic peptide, comprising administering an effective amount of the pharmaceutical composition of claim 5.

11. The method of claim 10, wherein said therapeutic peptide has FGF21 activity and comprises an amino acid sequence with at least a 90% sequence identity to SEQ ID NO:2.

12. The method of claim 10, wherein said scaffold is poly(ethylene glycol).

13. The method of claim 10, wherein said pharmaceutical composition is in a pharmaceutically acceptable formulation.

14. The method of claim 10, wherein said pharmaceutical composition is delivered to said patient by a transdermal, oral, parenteral, subcutaneous, intracutaneous, intravenous, intramuscular, intraarticular, intrasynovial, intrasternal, intrathecal, intralesional, intracranial injection, infusion, inhalation, ocular, topical, rectal, nasal, buccal, sublingual, vaginal, or implanted reservoir mode.

15. A method of manufacturing the pharmaceutical composition of claim 5, comprising conjugating said targeting group and said therapeutic peptide, wherein said conjugating step utilizes a coupling group.

16. The method according to claim 15, wherein said coupling group is a maleimide group.

17. The pharmaceutical composition resulting from the method of claim 15, wherein said composition comprises a carrier-drug conjugate containing a thiol linkage.

18. The method according to claim 15, wherein said conjugating step is accomplished by cycloaddition reactions.

19. The method of claim 15, wherein said scaffold is poly (ethylene glycol).

20. A pharmaceutical composition comprising:
    (a) a therapeutic peptide
    (b) a stably attached scaffold,
    (c) a targeting group that is Vitamin D that is not hydroxylated at the Carbon 1 position,
wherein after administration to a first subject, said therapeutic peptide has a half life measured by a functional assay of blood samples taken at a plurality of time points that is greater than a half life of said therapeutic peptide administered to a second subject without said attached scaffold and targeting group as measured by said functional assay of blood samples taken at said plurality of time points.

21. The pharmaceutical composition of claim 20, wherein said administration to said first and second subjects is accomplished by subcutaneous injection.

22. The pharmaceutical composition of claim 20, wherein said therapeutic peptide stably attached to said scaffold and targeting group retains about the same activity as said therapeutic peptide not attached to said scaffold and targeting group as measured by said functional assay.

23. The pharmaceutical composition of claim 20, wherein said functional assay is an Enzyme Linked Immunosorbant Assay (ELISA) analysis.

24. A carrier-drug conjugate comprising a targeting group that is non-hormonal vitamin D stably linked to a therapeutic peptide.

25. The carrier-drug conjugate of claim 24, wherein said targeting group is linked to said therapeutic peptide via a scaffold that is poly(ethylene glycol).

* * * * *

```
                        SEQUENCE LISTING

<160> NUMBER OF SEQ ID NOS: 10

<210> SEQ ID NO 1
<211> LENGTH: 209
<212> TYPE: PRT
<213> ORGANISM: Homo sapiens

<400> SEQUENCE: 1

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 2
<211> LENGTH: 181
<212> TYPE: PRT
<213> ORGANISM: Homo sapiens

<400> SEQUENCE: 2

His Pro Ile Pro Asp Ser Ser Pro Leu Leu Gln Phe Gly Gly Gln Val
1               5                   10                  15

Arg Gln Arg Tyr Leu Tyr Thr Asp Ala Gln Gln Thr Glu Ala His
            20                  25                  30

Leu Glu Ile Arg Glu Asp Gly Thr Val Gly Gly Ala Ala Asp Gln Ser
```

```
                  35                  40                  45
Pro Glu Ser Leu Leu Gln Leu Lys Ala Leu Lys Pro Gly Val Ile Gln
             50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 3
<211> LENGTH: 201
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Modified mature human FGF21:  N-terminal 6-his
      tag, tev cleavage site, additional 182P, and modified I3C
      and G170E using mature FGF21 numbering

<400> SEQUENCE: 3

Met Gly Ser His His His His His His Ser Ser Gly Glu Asn Leu Tyr
 1               5                  10                  15

Phe Gln Gly His Pro Cys Pro Asp Ser Ser Pro Leu Leu Gln Phe Gly
             20                  25                  30

Gly Gln Val Arg Gln Arg Tyr Leu Tyr Thr Asp Asp Ala Gln Gln Thr
         35                  40                  45

Glu Ala His Leu Glu Ile Arg Glu Asp Gly Thr Val Gly Gly Ala Ala
     50                  55                  60

Asp Gln Ser Pro Glu Ser Leu Leu Gln Leu Lys Ala Leu Lys Pro Gly
 65                  70                  75                  80

Val Ile Gln Ile Leu Gly Val Lys Thr Ser Arg Phe Leu Cys Gln Arg
                 85                  90                  95

Pro Asp Gly Ala Leu Tyr Gly Ser Leu His Phe Asp Pro Glu Ala Cys
            100                 105                 110

Ser Phe Arg Glu Leu Leu Leu Glu Asp Gly Tyr Asn Val Tyr Gln Ser
        115                 120                 125

Glu Ala His Gly Leu Pro Leu His Leu Pro Gly Asn Lys Ser Pro His
    130                 135                 140

Arg Asp Pro Ala Pro Arg Gly Pro Ala Arg Phe Leu Pro Leu Pro Gly
145                 150                 155                 160

Leu Pro Pro Ala Leu Pro Glu Pro Pro Gly Ile Leu Ala Pro Gln Pro
                165                 170                 175

Pro Asp Val Gly Ser Ser Asp Pro Leu Ser Met Val Glu Pro Ser Gln
            180                 185                 190
```

Gly Arg Ser Pro Ser Tyr Ala Ser Pro
        195                 200

<210> SEQ ID NO 4
<211> LENGTH: 606
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Optimized FGF21 nucleotide sequence for E. coli
      expression

<400> SEQUENCE: 4
atgggctcac atcatcacca ccatcatagc agcggagaga acttgtattt tcagggacat      60
ccgtgccctg acagcagccc gctgctgcag ttcggtggtc aagtccgtca gcgttacctg     120
tacactgacg acgcgcaaca gaccgaggcg cacctggaaa ttcgcgaaga tggtacggtg     180
ggtggcgcag cggaccaaag cccggagtcc ctgttgcagc tgaaggccct gaagccgggt     240
gtcatccaaa tcctgggcgt taaaaccagc cgttttctgt gccaacgtcc ggatggtgcg     300
ctgtacggtt ccctgcactt cgacccagag gcatgtagct tcgtgaact gctgctggaa     360 gatggctata atgtgtacca gtctgaggcg cacggtctgc cgttgcactt gccgggtaac     420
aaaagcccgc accgcgaccc agcaccgcgt ggtccggctc gcttcctgcc gctgccgggt     480
ctgcctccgg cgctgccgga gccgccaggc attctggctc gcaaccgcc ggatgttggc     540 agcagcgatc cgctgagcat ggttgaaccg tcgcagggcc gcagcccgtc ttatgccagc     600
ccgtaa                                                                606

<210> SEQ ID NO 5
<211> LENGTH: 28
<212> TYPE: PRT
<213> ORGANISM: Homo sapiens

<400> SEQUENCE: 5

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Rat Ghrelin with added C-term cysteine, serine
      at position 3 is (n-octanoyl-S)

<400> SEQUENCE: 6

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg Cys
            20                  25

<210> SEQ ID NO 7
<211> LENGTH: 474
<212> TYPE: PRT
<213> ORGANISM: Homo sapiens

<400> SEQUENCE: 7

Met Lys Arg Val Leu Val Leu Leu Ala Val Ala Phe Gly His Ala
1               5                   10                  15

Leu Glu Arg Gly Arg Asp Tyr Glu Lys Asn Lys Val Cys Lys Glu Phe
            20                  25                  30

Ser His Leu Gly Lys Glu Asp Phe Thr Ser Leu Ser Leu Val Leu Tyr
        35                  40                  45

Ser Arg Lys Phe Pro Ser Gly Thr Phe Glu Gln Val Ser Gln Leu Val
    50                  55                  60

Lys Glu Val Val Ser Leu Thr Glu Ala Cys Cys Ala Glu Gly Ala Asp
65                  70                  75                  80

Pro Asp Cys Tyr Asp Thr Arg Thr Ser Ala Leu Ser Ala Lys Ser Cys
                85                  90                  95

Glu Ser Asn Ser Pro Phe Pro Val His Pro Gly Thr Ala Glu Cys Cys
            100                 105                 110

Thr Lys Glu Gly Leu Glu Arg Lys Leu Cys Met Ala Ala Leu Lys His
        115                 120                 125

Gln Pro Gln Glu Phe Pro Thr Tyr Val Glu Pro Thr Asn Asp Glu Ile
    130                 135                 140

Cys Glu Ala Phe Arg Lys Asp Pro Lys Glu Tyr Ala Asn Gln Phe Met
145                 150                 155                 160

Trp Glu Tyr Ser Thr Asn Tyr Gly Gln Ala Pro Leu Ser Leu Leu Val
                165                 170                 175

Ser Tyr Thr Lys Ser Tyr Leu Ser Met Val Gly Ser Cys Cys Thr Ser
            180                 185                 190

Ala Ser Pro Thr Val Cys Phe Leu Lys Glu Arg Leu Gln Leu Lys His
        195                 200                 205

Leu Ser Leu Leu Thr Thr Leu Ser Asn Arg Val Cys Ser Gln Tyr Ala
    210                 215                 220

Ala Tyr Gly Glu Lys Lys Ser Arg Leu Ser Asn Leu Ile Lys Leu Ala
225                 230                 235                 240

Gln Lys Val Pro Thr Ala Asp Leu Glu Asp Val Leu Pro Leu Ala Glu
                245                 250                 255

Asp Ile Thr Asn Ile Leu Ser Lys Cys Cys Glu Ser Ala Ser Glu Asp
            260                 265                 270

Cys Met Ala Lys Glu Leu Pro Glu His Thr Val Lys Leu Cys Asp Asn
        275                 280                 285

Leu Ser Thr Lys Asn Ser Lys Phe Glu Asp Cys Cys Gln Glu Lys Thr
    290                 295                 300

Ala Met Asp Val Phe Val Cys Thr Tyr Phe Met Pro Ala Ala Gln Leu
305                 310                 315                 320

Pro Glu Leu Pro Asp Val Glu Leu Pro Thr Asn Lys Asp Val Cys Asp
                325                 330                 335

Pro Gly Asn Thr Lys Val Met Asp Lys Tyr Thr Phe Glu Leu Ser Arg
            340                 345                 350

Arg Thr His Leu Pro Glu Val Phe Leu Ser Lys Val Leu Glu Pro Thr
        355                 360                 365

Leu Lys Ser Leu Gly Glu Cys Cys Asp Val Glu Asp Ser Thr Thr Cys
    370                 375                 380

Phe Asn Ala Lys Gly Pro Leu Leu Lys Lys Glu Leu Ser Ser Phe Ile
385                 390                 395                 400

Asp Lys Gly Gln Glu Leu Cys Ala Asp Tyr Ser Glu Asn Thr Phe Thr

```
                    405                 410                 415
Glu Tyr Lys Lys Lys Leu Ala Glu Arg Leu Lys Ala Lys Leu Pro Asp
                420                 425                 430

Ala Thr Pro Thr Glu Leu Ala Lys Leu Val Asn Lys His Ser Asp Phe
            435                 440                 445

Ala Ser Asn Cys Cys Ser Ile Asn Ser Pro Pro Leu Tyr Cys Asp Ser
        450                 455                 460

Glu Ile Asp Ala Glu Leu Lys Asn Ile Leu
465                 470

<210> SEQ ID NO 8
<211> LENGTH: 1800
<212> TYPE: DNA
<213> ORGANISM: Homo sapiens

<400> SEQUENCE: 8
```

| | | | | | |
|---|---|---|---|---|---|
| tttaataata | attctgtgtt | gcttctgaga | ttaataattg | attaattcat | agtcaggaat | 60 |
| ctttgtaaaa | aggaaaccaa | ttacttttgg | ctaccacttt | tacatggtca | cctacaggag | 120 |
| agaggaggtg | ctgcaagact | ctctggtaga | aaaatgaaga | gggtcctggt | actactgctt | 180 |
| gctgtggcat | ttggacatgc | tttagagaga | ggccggagatt | atgaaaagaa | taaagtctgc | 240 |
| aaggaattct | cccatctggg | aaaggaggac | ttcacatctc | tgtcactagt | cctgtacagt | 300 |
| agaaaatttc | ccagtggcac | gtttgaacag | gtcagccaac | ttgtgaagga | agttgtctcc | 360 |
| ttgaccgaag | cctgctgtgc | ggaaggggct | gaccctgact | gctatgacac | caggacctca | 420 |
| gcactgtctg | ccaagtcctg | tgaaagtaat | tctccattcc | ccgttcaccc | aggcactgct | 480 |
| gagtgctgca | ccaaagaggg | cctggaacga | agctctgca | tggctgctct | gaaacaccag | 540 |
| ccacaggaat | tccctaccta | cgtggaaccc | acaaatgatg | aaatctgtga | ggcgttcagg | 600 |
| aaagatccaa | aggaatatgc | taatcaattt | atgtgggaat | attccactaa | ttacggacaa | 660 |
| gctcctctgt | cactttttagt | cagttacacc | aagagttatc | tttctatggt | agggtcctgc | 720 |
| tgtacctctg | caagcccaac | tgtatgcttt | ttgaaagaga | gactccagct | aaacattta | 780 |
| tcacttctca | ccactctgtc | aaatagagtc | tgctcacaat | atgctgctta | tggggagaag | 840 |
| aaatcaaggc | tcagcaatct | cataaagtta | gcccaaaaag | tgcctactgc | tgatctggag | 900 |
| gatgttttgc | cactagctga | agatattact | aacatcctct | ccaaatgctg | tgagtctgcc | 960 |
| tctgaagatt | gcatggccaa | agagctgcct | gaacacacag | taaaactctg | tgacaattta | 1020 |
| tccacaaaga | attctaagtt | tgaagactgt | tgtcaagaaa | aaacagccat | ggacgttttt | 1080 |
| gtgtgcactt | acttcatgcc | agctgcccaa | ctccccgagc | ttccagatgt | agagttgccc | 1140 |
| acaaacaaag | atgtgtgtga | tccaggaaac | accaaagtca | tggataagta | tacatttgaa | 1200 |
| ctaagcagaa | ggactcatct | tccggaagta | ttcctcagta | ggtacttgag | ccaaccctaa | 1260 |
| aaagccttgg | tgaatgctgt | gatgttgaag | actcaactac | ctgttttaat | gctaagggcc | 1320 |
| ctctactaaa | gaaggaacta | tcttctttca | ttgacaaggg | acaagaacta | tgtgcagatt | 1380 |
| attcagaaaa | tacatttact | gagtacaaga | aaaaactggc | agagcgacta | aaagcaaaat | 1440 |
| tgcctgatgc | cacacccacg | gaactggcaa | agctggttaa | caagcactca | gactttgcct | 1500 |
| ccaactgctg | ttccataaac | tcacctcctc | tttactgtga | ttcagagatt | gatgctgaat | 1560 |
| tgaagaatat | cctgtagtcc | tgaagcatgt | ttattaactt | tgaccagagt | tggagccacc | 1620 |
| caggggaatg | atctctgatg | acctaaccta | agcaaaacca | ctgagcttct | gggaagacaa | 1680 |
| ctaggatact | ttctactttt | tctagctaca | atatcttcat | acaatgacaa | gtatgatgat | 1740 | ttgctatcaa aataaattga aatataatgc aaaccataaa aaaaaaaaaa aaaaaaaaaa    1800

<210> SEQ ID NO 9
<211> LENGTH: 702
<212> TYPE: DNA
<213> ORGANISM: Homo sapiens

<400> SEQUENCE: 9
atgagcactg aaagcatgat ccgggacgtg gagctggccg aggaggcgct ccccaagaag      60 acagggggc cccagggctc caggcggtgc ttgttcctca gcctcttctc cttcctgatc     120
gtggcaggcg ccaccacgct cttctgcctg ctgcactttg gggtgatcgg ccccagagg     180 gaagagttcc ccagggacct ctctctaatc agccctctgg cccaggcagt cagatcatct     240
tctcgaaccc cgagtgacaa gcctgtagcc atgttgtag caaaccctca agctgagggg     300
cagctccagt ggctgaaccg ccgggccaat gccctcctgg ccaatggcgt ggagctgaga     360
gataaccagt tggtggtgcc atcagagggc ctgtacctca tctactccca ggtcctcttc     420
aagggccaag gctgccctc cacccatgtg ctcctcaccc acaccatcag ccgcatcgcc     480
gtctcctacc agaccaaggt caacctcctc tctgccatca gagcccctg ccagagggag     540 acccagagg gggctgaggc caagccctgg tatgagccca tctatctggg aggggtcttc     600
cagctggaga agggtgaccg actcagcgct gagatcaatc ggcccgacta tctcgacttt     660
gccgagtctg ggcaggtcta ctttgggatc attgccctgt ga                        702

<210> SEQ ID NO 10
<211> LENGTH: 233
<212> TYPE: PRT
<213> ORGANISM: Homo sapiens

<400> SEQUENCE: 10

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

```
Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225             230
```